US 9,109,199 B2

(12) United States Patent
Kortekaas et al.

(10) Patent No.: US 9,109,199 B2
(45) Date of Patent: Aug. 18, 2015

(54) METHODS TO PRODUCE BUNYAVIRUS REPLICON PARTICLES

(75) Inventors: Jeroen Alexander Kortekaas, Zwolle (NL); Robertus Jacobus Maria Moormann, Dronten (NL)

(73) Assignee: STICHTING DIENST LANDBOUWKUNDIG ONDERZOEK, Wageningen (NL)

( * ) Notice: Subject to any disclaimer, the term of this patent is extended or adjusted under 35 U.S.C. 154(b) by 0 days.

(21) Appl. No.: 13/822,794

(22) PCT Filed: Sep. 20, 2011

(86) PCT No.: PCT/NL2011/050631
§ 371 (c)(1),
(2), (4) Date: May 28, 2013

(87) PCT Pub. No.: WO2012/039607
PCT Pub. Date: Mar. 29, 2012

(65) Prior Publication Data
US 2013/0236493 A1      Sep. 12, 2013

Related U.S. Application Data

(60) Provisional application No. 61/468,597, filed on Mar. 29, 2011.

(30) Foreign Application Priority Data

Sep. 20, 2010  (EP) .................................. 10177709

(51) Int. Cl.
*C12N 7/00*        (2006.01)
*A61K 39/12*       (2006.01)
*C07K 14/005*      (2006.01)

(52) U.S. Cl.
CPC . *C12N 7/00* (2013.01); *A61K 39/12* (2013.01); *C07K 14/005* (2013.01); *C12N 2510/02* (2013.01); *C12N 2760/12022* (2013.01); *C12N 2760/12034* (2013.01); *C12N 2760/12043* (2013.01); *C12N 2760/12051* (2013.01); *C12N 2760/12234* (2013.01)

(58) Field of Classification Search
CPC ........ A61K 39/12; C07K 14/005; C12N 7/00; C12N 2760/12051; C12N 2760/12022; C12N 2760/12034; C12N 2760/12043; C12N 2510/02
See application file for complete search history.

(56) References Cited

U.S. PATENT DOCUMENTS

| | | | |
|---|---|---|---|
| 6,673,572 B2 * | 1/2004 | Parks et al. | 435/69.1 |
| 7,384,774 B2 * | 6/2008 | Palese et al. | 435/235.1 |
| 2010/0047277 A1 * | 2/2010 | Compans et al. | 424/208.1 |
| 2011/0110976 A1 * | 5/2011 | Weber et al. | 424/204.1 |

FOREIGN PATENT DOCUMENTS

WO    WO 2009150146 A1 * 12/2009

OTHER PUBLICATIONS

Wichgers Schreur PJ, Oreshkova N, Moormann RJ, Kortekaas J. Creation of rift valley Fever viruses with four-segmented genomes reveals flexibility in bunyavirus genome packaging. J Virol. Sep. 15, 2014;88(18):10883-93. Epub Jul. 9, 2014.*
Britton P, Green P, Kottier S, Mawditt KL, Penzes Z, Cavanagh D, Skinner MA. Expression of bacteriophage T7 RNA polymerase in avian and mammalian cells by a recombinant fowlpox virus. J Gen Virol. May 1996;77 ( Pt 5):963-7.*
Shi X, Goli J, Clark G, Brauburger K, Elliott RM. Functional analysis of the Bunyamwera orthobunyavirus Gc glycoprotein. J Gen Virol. Oct. 2009;90(Pt 10):2483-92. Epub Jul. 1, 2009.*
Habjan M, Penski N, Wagner V, Spiegel M, Overby AK, Kochs G, Huiskonen JT, Weber F. Efficient production of Rift Valley fever virus-like particles: The antiviral protein MxA can inhibit primary transcription of bunyaviruses. Virology. Mar. 15, 2009;385(2):400-8. Epub Jan. 19, 2009.*
Ikegami T, Peters CJ, Makino S. Rift valley fever virus nonstructural protein NSs promotes viral RNA replication and transcription in a minigenome system. J Virol. May 2005;79(9):5606-15.*
Wichgers Schreur PJ, Oreshkova N, Moormann RJ, Kortekaas J. Creation of Rift Valley fever viruses with four-segmented genomes reveals flexibility in bunyavirus genome packaging. J Virol. Sep. 2014;88(18):10883-93. Epub Jul. 9, 2014.*
Overby, et al., "Generation and Analysis of Infectious Virus-Like Particles of Uukuniemi Virus (Bunyaviridae): a Useful System for Studying Bunyaviral Packaging and Budding", J. Virol. 2006, 80(21):10428-10435.
Ikegami et al., "Rescue of Infectious Rift Valley Fever Virus Entirely from cDNA, Analysis of Virus Lacking the NSs Gene, and Expression of a Foreign Gene," Journal of Virology, 80(6): 2933-2940 (2006).
Bouloy et al., "Reverse Genetics Technology for Rift Valley Fever Virus: Current and Future Applications for the Development of Therapeutics and Vaccines," Antiviral Research, 84:101-118 (2009).
Habjan et al., "T7 RNA Polymerase-Dependent and -Independent Systems for cDNA-Based Rescue of Rift Valley Fever Virus," Journal of General Virology, 89:2157-2166 (2008).
Billecocq et al., "RNA Polymerase I-Mediated Expression of Viral RNA for the Rescue of Infectious Virulent and Avirulent Rift Valley Fever Viruses," Virology, 378:377-384 (2008).
Kortekaas et al., "Rift Valley Fever Virus Immunity Provided by a Paramyxovirus Vaccine Vector," Vaccine, 28:4394-4401 (2010).

* cited by examiner

*Primary Examiner* — Benjamin P Blumel
*Assistant Examiner* — Rachel Gill
(74) *Attorney, Agent, or Firm* — McDermott Will & Emery LLP

(57) ABSTRACT

The invention relates to methods of producing infectious bunyavirus replicon particles. These bunyavirus replicon particles are safe and can be used outside a biosafety containment. The invention further relates to recombinant bunyavirus replicon particles and uses of these recombinant bunyavirus replicon particles.

16 Claims, 28 Drawing Sheets

Figure 2:
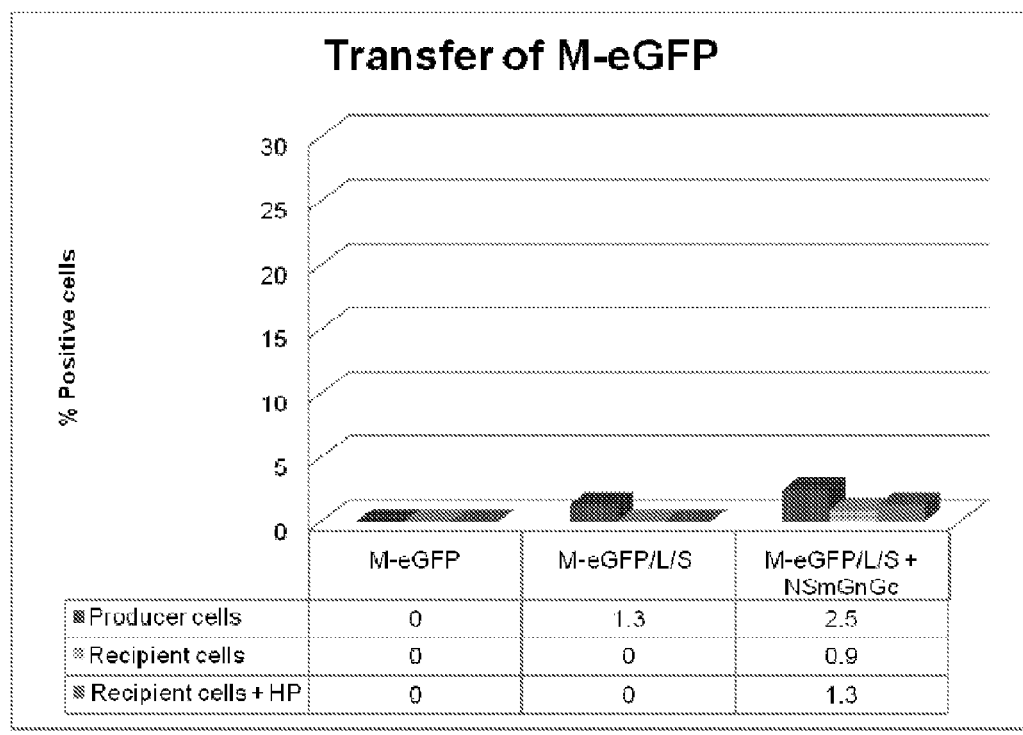

Figure 1
A
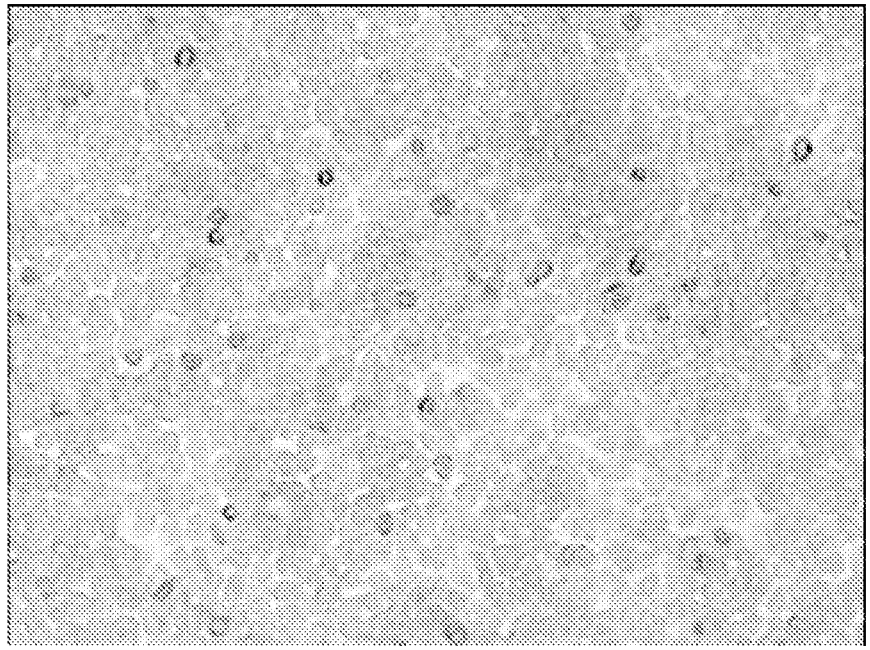
B
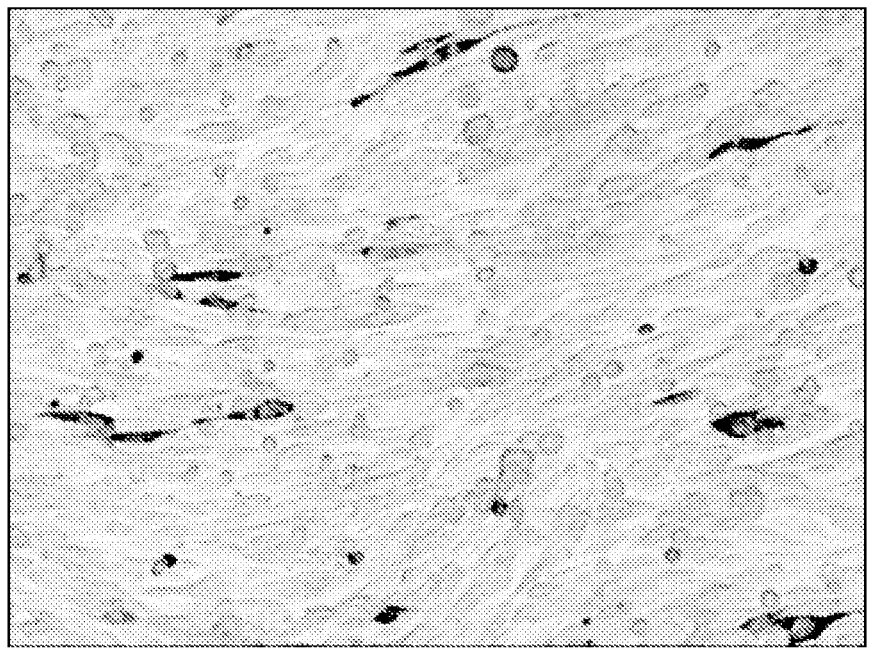

C

Figure 5

| | -8 | 16 | 24 | 40 | 48 | 64 | 72 | 88 |
|---|---|---|---|---|---|---|---|---|
| pCAGGS-GnGc | 0 | 5.39 | 5.19 | 6.16 | 6.16 | 5.78 | 6.36 | 5.58 |
| pCAGGS-NSmGnGc | 0 | 6.75 | 6.16 | 5.78 | 5.78 | 5.58 | 5 | 4.61 |
| Mock | 0 | 0 | 0 h.p.i. | 0 | 0 | 0 | 0 | 0 |

Figure 7

A

```
TTCGAGCTCGGTACCAGCGGAAGAGCGCCCAATACGCAAACCGCCTCTCCCCGCGCGTTGGCCGATTCATTAATGCAGGGGGATCT
CGATCCCGCGAAATTAATACGACTCACTATAGACACAAAGGCGCCCAATCATGGATTCTATATTATCAAAACAGCTGGTTGACAAG
ACTGGTTTTGTTAGAGTGCCAATCAAGCATTATGACTGTACAATGCTAACTCTGGCACTCCCAACATTTGATGTCTCCAAGATGGT
AGATAGAATTACCATAGACTTCAATTTAGACGACATACAAGGAGCATCTGAAATAGGCTCAACTTTGCTACCCTCTATGTCGATAG
ATGTGGAAGATATGGCCAATTTTGTTCACGATTTCACCTTTGGCCACTTAGCTGACAAGACTGACAGACTCTTAATGCGTGAGTTT
CCCATGATGAATGACGGGTTTGATCATCTGAGCCCTGACATGATTATCAAAACTACATCTGGCATGTATAACATCGTTGAGTTCAC
CACCTTTAGGGGGGATGAAAGAGGTGCATTCCAGGCTGCCATGACTAAACTCGCTAAGTATGAGGTTCCTTGTGAGAACAGATCTC
AGGGCAGGACTGTTGTTCTTTATGTTGTTAGCGCCTACCGGCATGGTGTTTGGTCTAATTTGGAGCTAGAGGACTCTGAAGCAGAG
GAGATGGTATATAGGTACAGACTTGCCCTTAGTGTGATGGATGAGCTAAGGACCTTGTTCCCAGAACTGTCATCCACAGATGAGGA
ACTAGGAAAGACTGAGAGAGAGTTGCTAGCCATGGTCTCCTCCATCCAAATAAATTGGTCAGTCACAGAATCTGTGTTTCCTCCCT
TTAGCAGAGAAATGTTTGACAGGTTCAGATCTTCTCCTCCCGATTCAGGTACATCACGAGGATAGTGAGCAGATGCCTCATAAAT
TCTCAAGAGAAACTCATCAATAATTCCTTCTTTGCTGAAGGGAATGATAAAGTTTTGAGATTTTCAAAAAACGCTGAGGAGTGTTC
CTTGGCAATAGAGAGAGCTTTAAATCAGTATAGGGCAGAAGACAACCTTAGGGACCTAAATGACCACAAGTCTACTATTCAGCTGC
CTCCCTGGCTGTCCTATCACGATGCCGATGGCAAAGATCTGTGCCCTCTTCAGGGATTAGATGTGAGAGGAGACCATCCCATGTGC
AACCTGTGGAGAGAAGTGGTTACCTCTGCAAATCTAGAGGAGATTGAGAGGATGCACGATGATGCAGCGGCAGAACTTGAGTTTGC
CCTTTCAGGGGTGAAGGACAGGCCAGATGAAAGAAACAGATACCATAGAGTCCATCTGAATATGGACTCAGATGATAGTGTCTACA
TAGCTGCTTTAGGGGTTAATGGAAAGAAGCATAAAGCAGACACATTAGTGCAACAAATGAGAGACAGGAGCAAACAGCCCTTCTCT
CCAGATCATGATGTGGATCACATATCTGAATTTCTCTCTGCATGCTCTAGTGACTTGTGGGCAACAGATGAGGACCTATACAACCC
TCTCTCTTGTGATAAAGAGCTTAGATTGGCAGCTCAGAGAATTCATCAGCCATCCTTATCAGAAAGGGGCTTCAATGAGATTATAA
CAGAGCACTACAGATTTATGGGAAGTAGGATAGGATCATGGTGCCAAATGGTCAGTTTAATAGGAGCTGAGCTATCAGCTTCTGTA
AAGCAACATGTTAAGCCTAACTATTTTGTGATTAAACGACTACTAGGTTCTGGGATTTTCTTGCTGATCAAGCCTACTTCCAGCAA
AAGCCATATATTCGTGTCTTTTGCAATTAAGCGCTCTTGCTGGGCCTTTGATCTCTCCACTTCCAGGGTTTTCAAACCCTACATAG
ATGCCGGGGATCTGTTAGTTACTGACTTTGTTTCTTACAAACTAAGTAAGCTTACCAACCTCTGCAAGTGCGTTTCGTTAATGGAA
TCCTCCTTCTCATTTTGGGCAGAGGCATTTGGGATTCCAAGCTGGAACTTTGTTAGTGACTTGTTCAGGTCTTCAGACTCTGCAGC
AATGGATGCCTCATACATGGGCAAACTCTCTTTATTAACCCTTTTGGAAGACAAAGCAACAACTGAAGAGTTACAGACTATTGCAA
GATATATAATCATGGAGGGCTTTGTCTCGCCCCCAGAAATCCCAAAACCTCACAAGATGACCTCTAAGTTTCCCAAGGTTCTCAGG
TCAGAGCTGCAGGTTTACTTATTAAACTGCTTATGCAGAACTATCCAGAAGATAGCAGGTGAGCCCTTTATTCTTAAGAAGAAGGA
TGGGTCTATATCCTGGGGTGGCATGTTTAATCCTTTTTCAGGGCGTCCACTGCTTGATATGCAACCACTCATCAGCTGTTGTTACA
ATGGTTACTTTAAAAACAAAGAAGAAGAGACTGAGCCTTCCTCCCTTTCTGGGATGTATAAGAAAATTATAGAACTTGAGCACCTT
AGACCACAGTCAGATGCCTTCTTGGGTTATAAAGATCCAGAACTACCTAGAATGCATGAGTTCAGTGTTTCTCACTTGAAGGAGGC
TTGCAATCATGCTAAGCTGGTCTTAAGGAGTCTCTATGGACAGAATTTCATGGAGCAAATAGACAACCAAATTATTCGAGAGCTCA
GTGGGTTGACTCTAGAAAGATTAGCCACACTTAAGGCCACAAGCAACTTTAATGAGAATTGGTATGTCTATAAGGATGTGGCAGAC
AAGAACTACACAAGGGATAAATTATTAGTGAAGATGTCAAAATATGCTTCTGAGGGAAAGAGCCTAGCTATCCAGAAGTTTGAGGA
TTGCATGAGGCAGATAGAGTCACAAGGATGTATGCACATTTGTTTGTTAAGAAACAACAGCATGGAGGTCTGAGAGAGATCTATG
TGATGGGTGCAGAGGAAAGAATTGTTCAATCGGTGGTGGAGACAATAGCCAGGTCTATAGGGAAGTTCTTTGCTTCTGATACCCTC
TGTAACCCCCCCAATAAGGTGAAAATTCCTGAGACACATGGCATTAGGGCTCGGAAGCAATGTAAGGGGCCTGTGTGGACTTGTGC
AACATCAGATGATGCAAGGAAGTGGAACCAAGGCCATTTTGTTACAAAGTTTGCCCTCATGCTATGTGAGTTCACCTCTCCTAAGT
GGTGGCCATTGATCATTAGGGGATGTTCAATGTTTACCAGGAAAAGGATGATGATGAATTTGAATTATCTTAAGATCCTGGATGGT
CATCGAGAGCTTGATATTAGAGATGACTTTGTGATGGATCTCTTCAAAAGCTTATCATGGTGAGGCAGAAGTTCCATGGGCTTTTAA
GGGTAAAACATATCTGGAAACCACGACAGGGATGATGCAGGGGATATTGCATTATACTTCCTCATTATTACACACCATTCATCAAG
AATACATCCGGTCCTTGTCCTTTAAAATATTCAACCTGAAGGTTGCTCTGAGATGAGCAAAAGCCTGGTTTGTGACATGATGCAA
GGATCAGATGATAGTAGCATGCTAATCAGCTTCCCAGCTGATGACGAGAAGGTTCTCACCAGATGCAAAGTGGCCGCAGCCATATG
CTTCCGAATGAAGAAGGAGCTGGGAGTGTACCTTGCCATCTACCCCTCAGAGAAGTCCACAGCAAACACAGATTTTGTGATGGAGT
ACAATTCTGAATTTTATTTCCACACCCAGCATGTTAGACCGACGATCAGGTGGATTGCAGCATGTTGCAGCCTGCCAGAAGTGGAA
ACACTAGTAGCCCGCCAGGAAGAGGCCTCTAATCTAATGACTTCAGTTACTGAGGGGGGTGGGTCATTCTCCTTAGCTGCAATGAT
TCAGCAAGCTCAGTGCACTCTCCATTACATGCTAATGGGCATGGGAGTGTCTGAGCTATTCTTAGATAAGAAGGCAGTGCTGA
AGTGGAATGACCCTGGTCTGGGTTTCTTCCTGCTTGACAATCCTTATGCGTGCGGGTTGGGAGGTTTTAGATTTAATCTCTTCAAA
GCCATCACCAGAACTGATTTGCAGAAGCTATATGCTTTCTTCATGAAGAAGGTTAAGGGCTCAGCTGCTAGGGACTGGGCAGATGA
GGATGTTACCATCCCAGAAACGTGTAGCGTGAGCCCAGGTGGCGCTCTAATTCTTAGCTCCTCTCTAAAGTGGGGATCTAGGAAGA
AGTTTCAGAAACTGAGAGACCGTTTGAACATACCAGAGAACTTGGATTGAGCTAATAAATGAGAATCCAGAGGTGCTCTATCGAGCT
CCCAGAACAGGCCCAGAAATATTGTTGCGCATTGCAGAGAAAGTCCATAGCCCTGGTGTTGTGTCATCATTGTCTTCTGGCAATGC
AGTCTGTAAAGTCATGGCCTCAGCTGTATACTTCTTATCAGCAACAATTTTTGAAGACACTGGACGCCCTGAGTTCAACTTCTTAG
AGGATTCCAAGTACAGCTTGCTACAAAAGATGGCCGCATATTCTGGCTTTTCATGGTTTCAATGATATGGAGCCAGAAGATATATTA
TTCCTATTCCCGAACATTGAGGAATTAGAATCACTGGATTCTATAGTTTACAACAAGGGAGAAATAGACATCATCCCAAGAGTTAA
TATCAGGGATGCAACCCAAACCAGGGTCACTATCTTTAATGAGCAGAAGACCCTCCGAACATCTCCAGAGAAGTTGGTGTCAGACA
AGTGGTTCGGGACTCAGAAGAGTAGGATAGGCAAAACAACTTTCCTGGCTGAATGGGAGAAGCTAAAGAAAATTGTGAAGTGGTTG
GAAGACACTCCAGAAGCAACTCTAGCTCACACTCCACTGAATAACCATATTCAGGTTAGGAATTTCTTTGCTAGAATGGAAAGCAA
GCCTAGAACGGTTAGAATAACAGGAGCTCCTGTAAAGAAGAGGTCAGGGGTTAGCAAGATAGCTATGGTTATCCGTGACAATTTCT
CCCGGATGGGCCATCTTAGAGGTGTAGAAGACCTCGCTGGCTTCACTCGTAGTGTGTCAGCTGAAATCCTCAAGCACTTTCTGTTC
TGCATACTACAGGGTCCATACAGTGAGAGCTATAAGCTACAGCTAATCTACAGAGTCCAGTGTCAAACGTTGAGATAAA
GGAATCGGATGGTAAGACAAAAACCAATTTGATTGGGATCCTTCAGAGATTTCTAGATGGTGATCACGTTGTCCCTATAATTGAAG
AGATGGGAGCCGGAACAGTGGGTGGATTCATCAAGAGACAACAGTCTAAGGTTGTGCAAAATAAAGTGGTCTATTATGGAGTTGGG
ATCTGGAGAGGCTTCATGGATGGATATCAGGTCCATCTTGAGATAGAAAATGACATAGGACAGCCCCCCAAGGCTTAGGAATGTCAC
AACTAACTGTCAGAGCAGCCCATGGGATCTGAGTGTCCCAATAAGGCAGTGGGCAGAAGACATGGGGGTCACAAACAACCAGGATT
ATTCCTCTAAATCTAGCAGAGGAGCTAGATATTGGATGCATTCATTTAGGATGCAAGGACCCAGCAAGCCATTTGGATGCCCAGTT
TATATTATTAAGGGTGACATGTCAGATGTTATCAGACTGAGAAAAGAGGAGGTGGAGATGAAAGTACGGGGCTCTACTCTCAACTT
GTACACTAAGCACCATTCTCATCAAGACTTACACATTTTATCTTACACTGCATCAGACAATGATCTCAGTCAGGCATTTTCAAGT
CAATATCAGATGAGGGAGTAGCTCAAGCCCTGCAGTTATTTGAGAGGGAGCCAAGCAACTGCTGGGTGAGATGTGAGTCTGTAGCT
CCAAAATTCATATCAGCCATCCTTGAGATATGTGAGGGGAAGAGACAGATAAAAGGAATCAACAGAACCAGACTCTCAGAGATTGT
GAGAATTTGTTCTGAATCTTCCCTAAGATCAAAGGTCGGATCTATGTTCTCATTTGTCGCCAATGTTGAGGAGGCCCATGATGTTG
ATTATGATGCGTTAATGGATGCTAATGATAGAAGATGCTAAGAACAATGCATTCAGTCATGTTGTCGATTGCATAGAGTTGGATGTT
AATGGTCCTTACGAGATGGAGTCTTTTGATCATCTGATGTCAACCTCTTTGGGCCAGCCCATTACAAGGACATCAGTTCATTATC
TATGATTGCTCATCCCTTAATGGATAAGTTTGTTGATTATGCCATTTCCAAGATGGGAGAGCCTCAGTTAGAAAAGTTCTAGAGA
CAGGTCGGTGCTCTAGCAAAGACTATGATTTATCAAAGGTTCTTCTTCAGAACTCTACAGAGACCAGAAGAGAGCATTAGGATAGAT
GATCTGGAGTTATATGAGGAGACAGATGTGGCGGATGACATGCTAGGCTAAGACCAATAAGCAAAGTCAGGCTTAGATTTAGGGAT
ACTACGCTAGTATTGGAATCCATGTGGGTTCTGATACTAGCATAGTGCTACAATATTGGGCGGTCTTTGTGTGGTCGGCATGGCA
TCTCCACCTCCTCGCGGTCCGACCTGGGCATCCGAAGGAGGACGTCGTCCACTCGGATGGCTAAGGGAGAGCTCGGATCCGGCTGC
TAACAAAGCCCGAAAGGAAGCTGAGTTGGCTGCTGCCACCGCTGAGCAATAACTAGCATAACCCCTTGGGGCCTCTAAACGGGTCT
TGAGGGGTTTTTTGCTGAAAGGAGGAACTATATCCGGATCGAGATCCTCTAGCCAGATCCTCTACGCCGGACGCATCGTGGCCGGC
GTCGACAAGCTTGGCGTAAT
```

Figure 7
B

```
GAATTCAGCGGAAGAGCGCCCAATACGCAAACCGCCTCTCCCCGCGCGTTGGCCGATTCATTAATGCAGGGGGATCTCGATCCCGC
GAAATTAATACGACTCACTATAGACACAAAGACGGTGCATTAAATGTATGTTTTACTAACAATTCTGATCACGGTTCTGGTGTGTG
AGGCGGTTATTAGAGTGTCTCTAAGTTCCACAAGAGAAGAGACCTGCTTTGGTGACTACACCAACCCAGAGATGATTGAAGGAGCT
TGGGATTCACTCAGAGAGGAGGAGATGCCAGAGGAGCTCTCCTGTTCCATATCAGGCATAAGGGAGGTCAAAACCTCAAGCCAGGA
ATTGTATAGGGCATTAAAAGCCATCATTGCTGCTGATGGCTTGAACAACATCACCTGCCATGGTAAGGATCCTGAGGATAAGATTT
CTCTCGTAAAGGGTCCTCCTCACAAAAAGCGGGTGGGGATAGTTCGGTGTGAGAGACGAAGAGACGCTAAGCAAATAGGAAGAGAA
ACCATGGCAGGGATTGCAATGACAGTCCTTCCAGCCTTAGCAGTTTTTGCTTTGGCACCTGTTGTTTTTGCTGAAGACCCTCATCT
CAGAAACAGACCAGGGAAGGGGCACAACTACATTGACGGGATGACTCAGGAGGACGCCACATGCAAACCTGTGACATATGCTGGGG
CTTGTAGCAGTTTTGATGTCTTGCTCGAAAAGGGAAAATTCCCCCTCTTCCAGTCGTATGCCCATCACAGAACCCTACTAGAAGCA
GTTCACGACACCATCATTGCAAAGGCTGATCCACCTAGCTGTGACCTTCAGAGTGCTCATGGGAATCCCTGCATGAAGGAGAAACT
CGTGATGAAGCACACTGTCCAAATGACTACCAGTCAGCTCATTACCTCAACAATGACGGGAAAATGGCTTCAGTCAAGTGCCCTC
CTAAATATGAGCTCACTGAGGACTGCAATTTTTGCAGGCAGATGACAGGTGCTAGCTTGAAGAAGGGGTCTTATCCTCTTCAGGAC
TTATTTTGTCAGTCAAGTGAGGATGATGGATCAAAATTAAAAACAAAAATGAAAGGGGTCTGCGAAGTGGGGGTTCAAGCACTCAA
AAAGTGTGATGGCCAACTCAGCACTGCACATGAGGTTGTGCCCTTTGCAGTATTTAAGAACTCAAAGAAGGTTTATCTTGATAAGC
TTGACCTCAAGACTGAGGAAAATCTGTTGCCAGACTCATTTGTCTGCTTCGAGCATAAGGGACAGTATAAAGGAACAATGGACTCT
GGTCAGACCAAGAGGGAGCTCAAAAGCTTTGATATCTCTCAGTGCCCCAAGATTGGAGGACATGGTAGCAAGAAGTGCACTGGGGA
CGCAGCTTTTTGCTCTGCTTATGAGTGCACTGCTCAATACGCCAATGCTTATTGTTCACATGCTAATGGGTCAGGAGTTGTACAGA
TACAAGTATCCGGGGTCTGGAAGAAGCCTTTGTGTGTCGGGTATGAGAGGGTGGTTGTGAAGAGAGAACTCTCTGCTAAGCCCATC
CAGAGAGTTGAGCCTTGCACAACTTGTATAACCAAATGTGAGCCTCACGGATTGGTTGTCCGATCAACAGGTTTCAAGATATCATC
TGCAGTTGCTTGTGCTAGCGGAGTTTGCGTTACAGGATCGCAGAGCCCTTCTACCGAGATTACACTCAAGTATCCAGGGATATCCC
AGTCCTCTGGGGGGACATAGGGGTTCACATGGCACATGATGATCAGTCAGTTAGCTCCAAAATAGTAGCTCACTGCCCTCCCCAG
GATCCATGCCTAGTGCATGGCTGCATAGTGTGTGCTCATGGCCTGATAAATTACCAGTGTCACACTGCTCTCAGTGCCTTTGTTGT
TGTGTTCGTATTTAGCTCTGTCGCAATAATTTGTTTGGCCATTCTTTATAAAGTTCTCAAGTGCCTAAAGATTGCCCCAAGGAAAG
TTCTGGATCCACTAATGTGGATTACTGTTTTCATCAGATGGGTGTATAAGAAGATGGTTGCCAGAGTAGCAGACAATATCAATCAG
GTGAACAGGGAAATAGGATGGATGGAAGGAGGCCAGCTGGCTCTAGGGAACCCTGCCCCTATTCCTCGTCATGCTCCAATTCCACG
TTATAGCACATACCTAATGCTACTATTGATTGTCTCATATGCATCAGCATGTTCAGAACTGATTCAGGCAAGCTCCAGAATCACCA
CTTGCTCCACAGAAGGTGTCAACACCAAGTGTAGGCTGTCTGGCACAGCATTAATCAGGGCAGGGTCAGTTGGGGCAGAGGCTTGT
TTGATGTTAAAGGGGGTCAAGGAAGACCAAACCAAGTTTTTGAAGATAAAAACTGTCTCAAGTGAGCTATCGTGCAGGGAGGGCCA
GAGCTATTGGACTGGGTCCTTTAGCCCTAAATGTCTGAGCTCAAGGAGATGCCATCTTGTCGGGGAATGTCATGTGAATAGGTGTC
TGTCTTGGAGAGACAATGAAACCTCAGCAGAATTTTCATTTGTTGGGGAAAGCACGACCATGCGGGAGAACAAGTGTTTTGAGCAG
TGTGGAGGATGGGGATGTGGGTGTTTCAATGTGAACCCATCTTGCTTATTTGTGCACACGTATCTGCAGTCAGTCAGAAAAGAGGC
CCTTAGAGTTTTCAACTGTATCGATTGGGTGCATAAACTCACTCTAGAGATTACTGACTTTGATGGCTCTGTTTCAACAATAGACC
TGGGAGCATCATCTAGCCGTTTCACAAACTGGGGTTCAGTTAGCCTCTCACTGGACGCAGAGGGCATTTCAGGCTCAAACAGCTTT
TCCTTCATTGAGAGCCCAGGCAAAGGGTATGCAATTGTTGATGAGCCATTCTCAGAAATTCCTCGGCAAGGGTTCTTGGGGAGAT
CAGGTGCAATTCAGAATCTTCAGTCCTGAGTGCTCATGAATCATGCCTTAGGGCACCAAATCTTATTTCATACAAGCCCATGATAG
ATCAGTTGGAGTGCACAACAAATCTGATTGATCCCTTTGTTGTCTTTGAGAGGGGCTCTCTGCCACAGACAAGGAATGACAAAACC
TTTGCAGCTTCAAAAGGAAATAGGGGTGTTCAAGCTTTCTCTAAGGGCTCTGTACAGGCTGATCTAACACTGATGTTTGACAATTT
TGAGGTGGACTTTGTGGGAGCAGCCGTGTCTTGTGATGCCGCCTTCTTAAATTTGACAGGTTGCTATTCCTGCAATGCAGGGGCCA
GAGTCTGCCTGTCTATCACATCCACAGGAACTGGAACTCTCTCTGCCCACAATAAAGATGGATCTCTGCATATAGTTCTTCCATCA
GAGAATGGAACAAAAGATCAGTGTCAGATACTACACTTCACTGTACCTGAGGTAGAGGAGGAGTTTATGTACTCTTGTGATGGAGA
TGAGCGGCCTCTGTTGGTGAAGGGAACCCTGATAGCTATTGATCCCATTTGATGATAGGCGAGAAGCAGGGGGGGAATCAACAGTTG
TGAATCCAAAATCTGGATCTTGGAATTTCTTTGACTGGTTTTCTGGACTCATGAGTTGGTTTGGAGGGCCTCTTAAGACTATACTC
CTCATTTGCCTGTATGTAGCATTATCAATTGGGCTCTTTTTCCTTCTTTATATATCTTGGAAGAACAGGCCTCTCTAAAATGTGGCT
TGCTGCCACCAAGAAAGCCTCATAGATCAGTACGTGTAGAAGCAATATATAGAAATAAGTAAACATAAGCAAATCTAATTATGTAA
ATATTGTACAGATGGGTCAAACTATTGGGATATCCAAGTTTAGAATCTTGTACAATAGTACTTTAGATGTAAGCTTAGTTGTAATT
TGGGGTGGTGGGGTGAGGCAGCAGTAGTCTCAAGTACATGTGGATATTCTAGTTAATGTGAATGTCTTTTGCCAGATTAGCTGGGA
ATTAAACTAACTCTTTGAAGTTGCACCGGTCTTTGTGTGGGTCGGCATGGCATCTCCACCTCCTCGCGGTCCGACCTGGGCATCCG
AAGGAGGACGTCGTCCACTCGGATGGCTAAGGGAGAGCTCGGATCCGGCTGCTAACAAAGCCCGAAAGGAAGCTGAGTTGGCTGCT
GCCACCGCTGAGCAATAACTAGCATAACCCCTTGGGGCCTCTAAACGGGTCTTGAGGGGTTTTTTGCTGAAAGGAGGAACTATATC
CGGATCGAGATCCTCTAGCCAGATCCTCTACGCCGGACGCATCGTGGCCGGCGTCGACTGCAGAGGC
```

Figure 7
C

GGATCCGATCCAATAGCGGAAGAGCGCCCAATACGCAAACCGCCTCTCCCCGCGCGTTGGCCGATTCATTAATGCAGGGGGATCTC
GATCCCGCGAAAT<u>TAATACGACTCACTATAG</u>A*CACAAAGACCCCCTAGTGCTTATCAAGTATATC*ATGGATTACTTTCCTGTGATA
TCTGTTGATTTGCAGAGTGGTCGTCGTGTTGTGTCAGTGGAGTACATTAGAGGTGATGGTCCTCCCAGGATACCTTATTCTATGGT
TGGGCCCTGTTGTGTCTTTCTCATGCACCATCGTCCTAGTCACGAGGTTCGCTTGCGATTCTCTGATTTCTACAATGTCGGAGAAT
TCCCATACCGAGTCGGACTTGGAGACTTTGTATCAAACGTTGCACCTCCACCAGCAAAGCCTTTTCAGAGACTTATTGATCTAATA
GGCCATATGACTCTTAGTGATTTCACAAGGTTCCCCAATCTGAAAGAAGCCATATCCTGGCCTCTTGGAGAACCCTCCCTGGCTTT
CTTTGACCTAAGCTCCACCAGAGTGCATAGGTCTGATGATATTAGAAGGGACCAGATTGCTACTCTAGCAATGAGGAGCTGCAAGA
TTACCAATGATCTGGAGGACTCCTTTGTTGGCTTACACAGGATGATAGTGACCGAGGCTATCCTCAGAGGGATTGACTTGTGCCTG
TTGCCAGGCTTTGATCTCATGTATGAGGTTGCTCATGTTCAGTGTGTTCGGCTCCTGCAGGCAGCAAGAGAGGATATTTCTAATGC
TGTAGTTCCAAACTCAGCTCTCATTGCTCTTATGGAGGAGAGCTTGATGCTGCGCTCATCACTCCCTAGCATGATGGGGAGAAACA
ACTGGGTTCCAGTTGTTCCTCCAATCCCAGATGTTGAGATAGAATCAGAGGAAGAGAGTGATGACGATGGATTTGTTGAGGTTGAT
TAG*AGATTAAGGCTGCCCCACCCCCCACCCCCAATCCCGACCGTAACCCAACCACCCCCTTTTCCCCAAACCCCTGGGCAGCCAC
TTAGGCTGCTGTCTTGTACGCCTGAGCAGCTGCCATGACAGCTGCTGACGGCTTCCCATTGGAATCCACAAGCCCAAAAGCTTTCA
AGAATTCTCTCCTCTTCTCATGGCTTATAAAGTTGCTATTCACTGCTGCATTCATTGGCTGCGTGAACGTTGCGGCAACCTCCTCC
TTTGTTCTACCTCGGAGGTTTGGGTTGATGACCCGGGAAGAACTGCAGCAGATACAGAGAGTGAGCATCCAATATTGCCCTTAGATA
GTCTTCTGGTAGAGAAGGGTCCACCATGCCAGCAAAGCTGGGGTGCATCATATGCCTTGGGTATGCAGGGGATAGGCCATCCATGG
TGGTCCCAGTGACAGGAAGCCACTCACTCAAGACGACCAAAGCCTGGCAAGTCCAGCCAGCCAGGGCAGCAGCAACTCGTGATAGA
GTCAACTCATCCCGGGAAGGATTCCCCTCCTTTAGCTTATACTTGTTGATGAGAGCCTCCACAGTTGCTTTGCCTTCTTTCGACAT
TTTCATCATCATCCTCCGGGGCTTGTTGCCACGAGTCAGAGCCAGAACAATCATTTTCTTGGCATCCTTCTCCCAGTCAGCCCCAC
CATACTGCTTTAAGAGTTCGATAACCCTACGGGCATCAAATCCTTGATAAGCAAACTCTCGGACCCACTGTTCAATCTCATTGCGG
TCCACTGCTTGAGCAGCAAACTGGATCGCAAGCTCTTGATAGTTGTCCAT*TATTGTAATAGTGTTTGTATCTCTAGGGAGCTTTGT
GT*<u>GGGTCGGCATGGCATCTCC</u>ACCTCCTCGCGGTCCGACCTGGGCATCCGAAGGAGGACGTCGTCCACTCGGATGGCTAAGGGAGA
GCTCGGATCCGGCTGCTAACAAAGCCCGAAAGGAAGCTGAGTTGGCTGCTGCCACCGCTGAGCAATAAC<u>TAGCATAACCCCTTGGG</u>
<u>GCCTCTAAACGGGTCTTGAGGGGTTTTTT</u>GCTGAAAGGAGGAACTATATCCGGATCGAGATCCTCTAGCCAGATCCTCTACGCCGG
ACGCATCGTGGCCGGCCCAATATCTAGA

Figure 7

D

TCTAGAGAAATTAATACGACTCACTATAGACACAAAGCTCCCTAGAGATACAAACACTATTACAATAATGGACAACTATCAAGAGC
TTGCGATCCAGTTTGCTGCTCAAGCAGTGGACCGCAATGAGATTGAACAGTGGGTCCGAGAGTTTGCTTATCAAGGATTTGATGCC
CGTAGGGTTATCGAACTCTTAAAGCAGTATGGTGGGGCTGACTGGGAGAAGGATGCCAAGAAAATGATTGTTCTGGCTCTGACTCG
TGGCAACAAGCCCCGGAGGATGATGATGAAAATGTCGAAAGAAGGCAAAGCAACTGTGGAGGCTCTCATCAACAAGTATAAGCTAA
AGGAGGGGAATCCTTCCCGGGATGAGTTGACTCTATCACGAGTTGCTGCTGCCCTGGCTGGCTGGACTTGCCAGGCTTTGGTCGTC
TTGAGTGAGTGGCTTCCTGTCACTGGGACCACCATGGATGGCCTATCCCCTGCATACCCAAGGCATATGATGCACCCCAGCTTTGC
TGGCATGGTGGACCCTTCTCTACCAGAAGACTATCTAAGGGCAATATTGGATGCTCACTCTCTGTATCTGCTGCAGTTCTCCCGGG
TCATCAACCCAAACCTCCGAGGTAGAACAAAGGAGGAGGTTGCCGCAACGTTCACGCAGCCAATGAATGCAGCAGTGAATAGCAAC
TTTATAAGCCATGAGAAGAGGAGAGAATTCTTGAAAGCTTTTGGGCTTGTGGATTCCAATGGGAAGCCGTCAGCAGCTGTCATGGC
AGCTGCTCAGGCGTACAAGACAGCAGCCTAA*GTGGCTGCCCAGGGGTTTGGGGAAAAGGGGGTGGTTGGGGTTACGGTCGGGATTG
GGGGTGGGGGGTGGGGCAGCCTTAATCTT*CAACAGATATCACAGGAAAGTAATCCAT*GATATACTTGATAAGCACTAGGGGGTCTT
TGTGT*GGGTCGGCATGGCATCTCCACCTCCTCGCGGTCCGACCTGGGCATCCGAAGGAGGACGTCGTCCACTCGGATGGCTAAGGG
AGAGCTCGGATCCGGCTGCTAACAAAGCCCGAAAGGAAGCTGAGTTGGCTGCTGCCACCGCTGAGCAATAACTAGCATAACCCCTT
GGGGCCTCTAAACGGGTCTTGAGGGGTTTTTTGCTGAAAGGAGGAACTATATCCGGATCGAGATCCTCTAGCCAGATCCTCTACGC
CGGACGCATCGTGGCCGGCGGGCCC

Figure 7

E

TAATACGACTCACTATAGACACAAAGCTCCCTAGAGATACAAACACTATTACAATAATGGACAACTATCAAGAGCTTGCGATCCAG
TTTGCTGCTCAAGCAGTGGACCGCAATGAGATTGAACAGTGGGTCCGAGAGTTTGCTTATCAAGGATTTGATGCCCGTAGGGTTAT
CGAACTCTTAAAGCAGTATGGTGGGGCTGACTGGGAGAAGGATGCCAAGAAAATGATTGTTCTGGCTCTGACTCGTGGCAACAAGC
CCCGGAGGATGATGATGAAAATGTCGAAAGAAGGCAAAGCAACTGTGGAGGCTCTCATCAACAAGTATAAGCTAAAGGAGGGGAAT
CCTTCCCGGGATGAGTTGACTCTATCACGAGTTGCTGCTGCCCTGGCTGGCTGGACTTGCCAGGCTTTGGTCGTCTTGAGTGAGTG
GCTTCCTGTCACTGGGACCACCATGGATGGCCTATCCCCTGCATACCCAAGGCATATGATGCACCCCAGCTTTGCTGGCATGGTGG
ACCCTTCTCTACCAGAAGACTATCTAAGGGCAATATTGGATGCTCACTCTCTGTATCTGCTGCAGTTCTCCCGGGTCATCAACCCA
AACCTCCGAGGTAGAACAAAGGAGGAGGTTGCCGCAACGTTCACGCAGCCAATGAATGCAGCAGTGAATAGCAACTTTATAAGCCA
TGAGAAGAGGAGAGAATTCTTGAAAGCTTTTGGGCTTGTGGATTCCAATGGGAAGCCGTCAGCAGCTGTCATGGCAGCTGCTCAGG
CGTACAAGACAGCAGCCTAA*GTGGCTGCCCAGGGGTTTGGGAAAAGGGGGTGGTTGGGGTTACGGTCGGATTGGGGTGGGGGG
TGGGGCAGCCTTAATCT*CTAATCAACCTCAACAAATCCATCGTCATCACTCTCTTCCTCTGATTCTATCTCAACATCTGGGATTGG
AGGAACAACTGGAACCCAGTTGTTTCTCCCCATCATGCTAGGGAGTGATGAGCGCAGCATCAAGCTCTCCTCCATAAGAGCAATGA
GAGCTGAGTTTGGAACTACAGCATTAGAAATATCCTCTCTTGCTGCCTGCAGGAGCCGAACACACTGAACATGAGCAACCTCATAC
ATGAGATCAAAGCCTGGCAACAGGCACAAGTCAATCCCTCTGAGGATAGCCTCGGTCACTATCATCCTGTGTAAGCCAACAAAGGA
GTCCTCCAGATCATTGGTAATCTTGCAGCTCCTCATTGCTAGAGTAGCAATCTGGTCCCTTCTAATATCATCAGACCTATGCACTC
TGGTGGAGCTTAGGTCAAAGAAAGCCAGGGAGGGTTCTCCAAGAGGCCAGGATATGGCTTCTTTCAGATTGGGGAACCTTGTGAAA
TCACTAAGAGTCATATGGCCTATTAGATCAATAAGTCTCTGAAAAGGCTTTGCTGGTGGAGGTGCAACGTTTGATACAAAGTCTCC
AAGTCCGACTCGGTATGGGAATTCTCCGACATTGTAGAAATCAGAGAATCGCAAGCGAACCTCGTGACTAGGACGATGGTGCATGA
GAAAGACACAACAGGGCCCAACCATAGAATAAGGTATCCTGGGAGGACCATCACCTCTAATGTACTCCACTGACACAACACGACGA
CCACTCTGCAAATCAACAGATATCACAGGAAAGTAATCCAT*GATATACTTGATAAGCACTAGGGGGTCTTTGTGGGTCGGCATG
GCATCTCCACCTCCTCGCGGTCCGACCTGGGCATCCGAAGGAGGACGTCGTCCACTCGGATGGCTAAGGGAGAGCTCGGATCCGGC
TGCTAACAAAGCCCGAAAGGAAGCTGAGTTGGCTGCTGCCACCGCTGAGCAATAACTAGCATAACCCCTTGGGGCCTCTAAACGGG
TCTTGAGGGGTTTTTG

Figure 7
F

```
GGTACCTCGCGAATGCATTAGAGAAATTAATACGACTCACTATAGACACAAAGCTCCCTAGAGATACAAACACTATTACAATAATG
GACAACTATCAAGAGCTTGCGATCCAGTTTGCTGCTCAAGCAGTGGACCGCAATGAGATTGAACAGTGGGTCCGAGAGTTTGCTTA
TCAAGGATTTGATGCCCGTAGGGTTATCGAACTCTTAAAGCAGTATGGTGGGGCTGACTGGGAGAAGGATGCAAGAAAATGATTG
TTCTGGCTCTGACTCGTGGCAACAAGCCCCGGAGGATGATGATGAAAATGTCGAAAGAAGGCAAAGCAACTGTGGAGGCTCTCATC
AACAAGTATAAGCTAAAGGAGGGGAATCCTTCCCGGGATGAGTTGACTCTATCACGAGTTGCTGCTGCCCTGGCTGGCTGGACTTG
CCAGGCTTTGGTCGTCTTGAGTGAGTGGCTTCCTGTCACTGGGACCACTATGGATGGCCTATCCCCTGCATACCCAAGGCATATGA
TGCACCCCAGCTTTGCTGGCATGGTGGACCCTTCTCTACCAGAAGACTATCTAAGGGCAATATTGGATGCTCACTCTCTGTATCTG
CTGCAGTTCTCCCGGGTCATCAACCCAAACCTCCGAGGTAGAACAAAGGAGGAGGTTGCCGCAACGTTCACGCAGCCAATGAATGC
AGCAGTGAATAGCAACTTTATAAGCCATGAGAAGAGGAGAGAATTCTTGAAAGCTTTTGGGCTTGTGGATTCCAATGGGAAGCCGT
CAGCAGCTGTCATGGCAGCTGCTCAGGCGTACAAGACAGCAGCCTAAGTGGCTGCCCAGGGGTTTGGGGAAAAGGGGGTGGTTGGG
GTTACGGTCGGGATTGGGGGTGGGGGGTGGGGCAGCCTTAATCTTCTAGATTACTTGTACAGCTCGTCCATGCCGTGAGTGATCCC
GGCGGCGGTCACGAACTCCAGCAGGACCATGTGATCGCGCTTCTCGTTGGGGTCTTTGCTCAGGGCGGACTGGGTGCTCAGGTAGT
GGTTGTCGGGCAGCAGCACGGGGCCGTCGCCGATGGGGGTGTTCTGCTGGTAGTGGTCGGCGAGCTGCACGCTGCCGTCCTCGATG
TTTGTGGCGGATCTTGAAGTTCACCTTGATGCCGTTCTTCTGCTTGTCGGCCATGATATAGACGTTGTGGCTGTTGTAGTTGTACTC
CAGCTTGTGCCCCAGGATGTTGCCGTCCTCCTTGAAGTCGATGCCCTTCAGCTCGATGCGGTTCACCAGGGTGTCGCCCTCGAACT
TCACCTCGGCGCGGGTCTTGTAGTTGCCGTCGTCCTTGAAGAAGATGGTGCGCTCCTGGACGTAGCCTTCGGGCATGGCGGACTTG
AAGAAGTCGTGCTGCTTCATGTGGTCGGGGTAGCGGCTGAAGCACTGCACGCCGTAGGTCAGGGTGGTCACGAGGGTGGGCCAGGG
CACGGGCAGCTTGCCGGTGGTGCAGATGAACTTCAGGGTCAGCTTGCCGTAGGTGGCATCGCCCTCGCCCTCGCCGGACACGCTGA
ACTTGTGGCCGTTCACGTCGCCGTCCAGCTCGACCAGGATGGGCACCACCCCGGTGAACAGCTCCTCGCCCTTGCTCACCATGGGA
TATACTTGATAAGCACTAGGGGGTCTTTGTGTGGGTCGGCATGGCATCTCCACCTCCTCGCCGGTCCGACCTGGGCATCCGAAGGAG
GACGTCGTCCACTCGGATGGCTAAGGGAGAGCTCGGATCCGGCTGCTAACAAAGCCCGAAAGGAAGCTGAGTTGGCTGCTGCCACC
GCTGAGCAATAACTAGCATAACCCCTTGGGGCCTCTAAACGGGTCTTGAGGGGTTTTTTGCTGAAAGGTCGAC
```

Figure 7
G

```
GAATTCGAAATTAATACGACTCACTATAGACACAAAGACCGGTGCAACTTCAAAGAGTTAGTTTAATTCCCAGCTAATCTGGCAAA
AGACATTCACATTAACTAGAATATCCACATGTACTTGAGACTACTGCTGCCTCACCCCACCACCCCAAATTACAACTAAGCTTACA
TCTAAAGTACTATTGTACAAGATTCTAAACTTGGATATCCCAATAGTTTGACCCATCTGTACAATATTTACATAATTAGATTTGCT
TATGTTTACTTATTTCTATATATTGCTTCTACACGTACTGATTCTAGAGCCCGTGGCACGTGACTAGTAAGCTTGATATCTCGAGG
CGCGCCAGCTGCGGCCGCTGATTCGGTACCCGGGATCCTTGCTCACCATGGTTAATGCACCGTCTTTGTGGGTCGGCATGGCAT
CTCCACCTCCTCGCGGTCCGACCTGGGCATCCGAAGGAGGACGTCGTCCACTCGGATGGCTAAGGGAGAGCTCGGATCCGGCTGCT
AACAAAGCCCGAAAGGAAGCTGAGTTGGCTGCTGCCACCGCTGAGCAATAACTAGCATAACCCCTTGGGGCCTCTAAACGGGTCTT
GAGGGGTTTTTTGCTGAAAGGAGGAACTATATCCGGATCGAGATCCTCTAGCCAGATCCTCTACGCCGGACGCATCGTGGCCGGCG
TCGACTGCCTGCAG
```

Figure 7
H

```
TAATACGACTCACTATAGACACAAAGACCGGTGCAACTTCAAAGAGTTAGTTTAATTCCCAGCTAATCTGGCAAAAGACATTCACA
TTAACTAGAATATCCACATGTACTTGAGACTACTGCTGCCTCACCCCACCACCCCAAATTACAACTAAGCTTACATCTAAAGTACT
ATTGTACAAGATTCTAAACTTGGATATCCCAATAGTTTGACCCATCTGTACAATATTTACATAATTAGATTTGCTTATGTTTACTT
ATTTCTATATATTGCTTCTACACGTACTGATTCTAGATTACTTGTACAGCTCGTCCATGCCGTGAGTGATCCCGGCGGCGGTCACG
AACTCCAGCAGGACCATGTGATCGCGCTTCTCGTTGGGTCTTTGCTCAGGGCGGACTGGGTGCTCAGGTAGTGGTTGTCGGGCAG
CAGCACGGGCCGTCGCCGATGGGGTGTTCTGCTGGTAGTGGTCGGCGAGCTGCACGCTGCCGTCCTCGATGTTGTGGCGGATCT
TGAAGTTCACCTTGATGCCGTTCTTCTGCTTGTCGGCCATGATATAGACGTTGTGGCTGTTGTAGTTGTACTCCAGCTTGTGCCCC
AGGATGTTGCCGTCCTCCTTGAAGTCGATGCCCTTCAGCTCGATGCGGTTCACCAGGGTGTCGCCCTCGAACTTCACCTCGGCGCG
GGTCTTGTAGTTGCCGTCGTCCTTGAAGAAGATGGTGCGCTCCTGGACGTAGCCTTCGGGCATGGCGGACTTGAAGAAGTCGTGCT
GCTTCATGTGGTCGGGGTAGCGGCTGAAGCACTGCACGCCGTAGGTCAGGGTGGTCACGAGGGTGGGCCAGGGCACGGGCAGCTTG
CCGGTGGTGCAGATGAACTTCAGGGTCAGCTTGCCGTAGGTGGCATCGCCCTCGCCCTCGCCGGACACGCTGAACTTGTGGCCGTT
CACGTCGCCGTCCAGCTCGACCAGGATGGGCACCACCCCGGTGAACAGCTCCTCGCCCTTGCTCACCATGGTTAATGCACCGTCTT
TGTGTGGGTCGGCATGGCATCTCC
```

Figure 7

I

GAATTCGCTCTTCAAGCACCACCATGGCCGGAATCGCCATGACAGTGTTGCCTGCACTGGCCGTGTTTGCTTTGGCTCCCGTGGTG
TTTGCTGAAGACCCGCACCTGCGCAACCGTCCTGGCAAGGGCCACAACTATATTGACGGCATGACCCAGGAAGACGCTACATGTAA
GCCGGTGACATATGCTGGCGCCTGCTCTAGCTTCGACGTGCTCCTGGAAAAGGGAAAATTCCCACTGTTTCAGTCCTATGCTCATC
ACCGCACCCTGCTGGAGGCCGTCCACGACACAATTATCGCAAAGGCCGATCCCCCTAGCTGCGACCTGCAGAGCGCCATGGCAAC
CCGTGCATGAAAGAGAAACTGGTGATGAAAACACATTGCCCGAATGACTACCAGTCTGCACACTATCTCAACAATGACGGCAAGAT
GGCTTCCGTGAAATGCCCACCAAAGTACGAACTGACCGAGGATTGTAACTTTTGCCGCCAGATGACGGGCGCAAGTCTTAAGAAGG
GTAGTTACCCTCTGCAGGACCTGTTTTGTCAGTCCTCAGAGGACGACGGCAGCAAGCTCAAAACTAAAATGAAGGGCGTGTGCGAG
GTGGGTGTGCAAGCCCTTAAAAAGTGCGACGGCCAGCTCTCCACCGCCCACGAAGTGGTCCCTTTTGCTGTTTTTAAGAATAGCAA
GAAGGTGTACCTCGACAAACTGGATCTGAAAACTGAAGAAAACCTGCTTCCTGATAGTTTCGTGTGCTTCGAGCACAAAGGCCAGT
ACAAGGGTACCATGGACTCCGGTCAGACCAAACGCGAGCTGAAATCCTTCGACATTTCCCAGTGCCCCAAGATCGGAGGACACGGA
AGCAAGAAATGCACCGGCGACGCCGCCTTCTGTAGCGCCTACGAATGCACTGCCCAATATGCCAACGCTTATTGCTCTCACGCCAA
CGGTTCTGGCGTGGTGCAGATTCAGGTGTCCGGCGTCTGGAAGAAGCCGTTGTGTGTGGGCTATGAACGCGTGGTGGTGAAGCGGG
AGTTGAGCGCTAAGCCCATCCAGCGTGTGGAGCCATGCACCACCTGCATCACAAAGTGTGAACCACACGGTCTGGTGGTGAGGTCT
ACCGGATTTAAGATTAGCTCTGCAGTCGCCTGTGCAAGTGGCGTGTGTGTCACTGGCTCACAGAGTCCCTCAACGGAAATCACTTT
GAAGTATCCCGGCATCAGCCAAAGCTCTGGAGGCGATATCGGCGTCCATATGGCCCACGACGACCAGAGCGTGAGCTCAAAGATTG
TTGCCCACTGCCCCCCGCAGGACCCTTGCCTTGTGCACGGCTGCATTGTGTGCGCCCACGGATTGATTAACTACCAATGCCACACC
GCACTCAGCGCCTTTGTCGTGGTTTTTGTGTTTTCTTCCGTTGCAATCATTTGCCTGGCCATCCTGTACAAAGTCCTCAAATGCCT
GAAAATTGCCCCTAGGAAGGTCCTCGACCCGTTGATGTGGATTACGGTGTTCATCCGATGGGTGTATAAGAAGATGGTGGCAAGGG
TGGCAGATAACATTAACCAGGTGAACAGAGAGATAGGATGGATGGAAGGTGGCCAGTTGGCACTTGGTAACCCTGCCCCCATCCCT
CGACACGCCCCCATTCCGAGATATAGCACCTACCTCATGCTGCTTCTGATCGTGAGCTACGCATCCGCCTGCAGCGAGCTGATTCA
GGCCAGCAGTAGAATCACGACGTGCAGTACAGAAGGAGTGAACACCAAATGCCGCCTGTCCGGAACCGCCCTGATTCGCGCCGGCT
CCGTCGGCGCCGAGGCCTGTCTCATGCTCAAGGGCGTGAAGGAGGACCAGACCAAATTCCTGAAGATCAAGACTGTTTCATCTGAA
CTCTCATGTCGGGAGGGACAGTCCTACTGGACAGGTAGCTTCAGTCCAAAGTGTCTTTCCTCCCGTCGCTGTCACCTGGTCGGGGA
ATGTCATGTGAATAGGTGTCTGTCATGGCGCGACAACGAGACTTCCGCCGAATTTTCTTTCGTGGGTGAATCCACCACCATGCGGG
AAAATAAATGTTTCGAACAGTGCGGCGGCTGGGGTTGTGGCTGCTTCAACGTGAACCCGTCTTGCCTCTTTGTTCATACCTATCTG
CAATCTGTGCGCAAGGAAGCTCTGCGCGTTTTTAATTGTATCGACTGGGTGCATAAGCTCACATTGGAAATCACAGATTTTGACGG
CTCCGTCAGCACCATCGACCTGGGAGCTTCTTCATCACGATTTACAAACTGGGGTAGCGTGAGTCTCTCCCTGGATGCCGAAGGTA
TTTCAGGCAGCAACAGTTTTAGTTTCATCGAATCCCCTGGCAAGGGTTATGCCATCGTGGACGAACCTTTCTCCGAGATCCCAAGG
CAGGGCTTCCTTGGAGAGATCAGGTGCAACTCAGAAAGCTCCGTGTTGAGTGCTCATGAGAGTTGTCTGAGGGCCCCGAACCTGAT
CTCCTATAAGCCCATGATTGACCAGCTTGAGTGCACAACAAATCTTATAGATCCCTTCGTCGTGTTTGAAAGAGGCTCCCTCCCCC
AGACCCGCAACGACAAGACGTTCGCAGCTTCTAAGGGCAACCGTGGAGTCCAGGCCTTTAGCAAGGGTTCCGTGCAGGCCGACCTG
ACATTGATGTTCGATAACTTCGAGGTGGATTTCGTCGGAGCCGCTGTCTCCTGCGATGCAGCATTTCTGAATCTGACTGGCTGCTA
TAGTTGCAATGCTGGAGCACGCGTGTGCCTGAGCATTACCTCCACTGGTACAGGTACCCTGTCCGCCCACAATAAAGATGGAAGTC
TTCACATCGTGCTGCCTAGCAGAACAGGCACAAAGGACCAATGTCAGATTCTGCACTTTACCGTGCCCGAGGTGGAGGAAGAGTTC
ATGTACTCCTGTGATGGCGATGAGAGGCCTCTGCTGGTCAAGGGCACTCTCATCGCCATTGACCCTTTTGATGACAGACGCGAGGC
TGGCGGAGAGAGCACTGTCGTTAACCCAAAGAGCGGCTCTTGGAATTTCTTTGACTGGTTCAGCGGACTCATGTCCTGGTTTGGAG
GCCCACTCAAGACGATTCTCCTGATCTGCCTGTACGTGGCTCTGAGTATCGGACTCTTCTTCCTCCTGATCTATCTCGGAAGAACC
GGCTTGTCAAAAATGTGGCTGGCCGCTACAAAGAAAGCCAGTTAAGCTCTTCCTCAGCGGCCGC

Figure 7
J

GAATTCACCATGTATGTTTTACTAACAATTCTGATCACGGTTCTGGTGTGTGAGGCGGTTATTAGAGTGTCTCTAAGTTCCACAAG
AGAAGAGACCTGCTTTGGTGACTACACCAACCCAGAGATGATTGAAGGAGCTTGGGATTCACTCAGAGAGGAGGAGATGCCAGAGG
AGCTCTCCTGTTCCATATCAGGCATAAGGGAGGTCAAAACCTCAAGCCAGGAATTGTATAGGGCATTAAAAGCCATCATTGCTGCT
GATGGCTTGAACAACATCACCTGCCATGGTAAGGATCCTGAGGATAAGATTTCTCTCGTAAAGGGTCCTCCTCACAAAAAGCGGGT
GGGGATAGTTCGGTGTGAGAGACGAAGAGACGCTAAGCAAATAGGAAGAGAAACCATGGCAGGGATTGCAATGACAGTCCTTCCAG
CCTTAGCAGTTTTTGCTTTGGCACCTGTTGTTTTTGCTGAAGACCCTCATCTCAGAAACAGACCAGGGAAGGGGCACAACTACATT
GACGGGATGACTCAGGAGGACGCCACATGCAAACCTGTGACATATGCTGGGGCTTGTAGCAGTTTTGATGTCTTGCTCGAAAAGGG
AAAATTCCCCCTCTTCCAGTCGTATGCCCATCACAGAACCCTACTAGAAGCAGTTCACGACACCATCATTGCAAAGGCTGATCCAC
CTAGCTGTGACCTTCAGAGTGCTCATGGGAATCCCTGCATGAAGGAGAAACTCGTGATGAAGACACACTGTCCAAATGACTACCAG
TCAGCTCATTACCTCAACAATGACGGGAAAATGGCTTCAGTCAAGTGCCCTCCTAAATATGAGCTCACTGAGGACTGCAATTTTTG
CAGGCAGATGACAGGTGCTAGCTTGAAGAAGGGGTCTTATCCTCTTCAGGACTTATTTTGTCAGTCAAGTGAGGATGATGGATCAA
AATTAAAAACAAAAATGAAAGGGGTCTGCGAAGTGGGGGTTCAAGCACTCAAAAAGTGTGATGGCCAACTCAGCACTGCACATGAG
GTTGTGCCCTTTGCAGTATTTAAGAACTCAAAGAAGGTTTATCTTGATAAGCTTGACCTCAAGACTGAGGAAAATCTGTTGCCAGA
CTCATTTGTCTGCTTCGAGCATAAGGGACAGTATAAAGGAACAATGGACTCTGGTCAGACCAAGAGGGAGCTCAAAAGCTTTGATA
TCTCTCAGTGCCCCAAGATTGGAGGACATGGTAGCAAGAAGTGCACTGGGGACGCAGCTTTTTGCTCTGCTTATGAGTGCACTGCT
CAATACGCCAATGCTTATTGTTCACATGCTAATGGGTCAGGAGTTGTACAGATACAAGTATCCGGGGTCTGGAAGAAGCCTTTGTG
TGTCGGGTATGAGAGGGTGGTTGTGAAGAGAGAACTCTCTGCTAAGCCCATCCAGAGAGTTGAGCCTTGCACAACTTGTATAACCA
AATGTGAGCCTCACGGATTGGTTGTCCGATCAACAGGTTTCAAGATATCATCTGCAGTTGCTTGTGCTAGCGGAGTTTGCGTTACA
GGATCGCAGAGCCCTTCTACCGAGATTACACTCAAGTATCCAGGGATATCCCAGTCCTCTGGGGGGGACATAGGGGTTCACATGGC
ACATGATGATCAGTCAGTTAGCTCCAAAATAGTAGCTCACTGCCCTCCCCAGGATCCATGCCTAGTGCATGGCTGCATAGTGTGTG
CTCATGGCCTGATAAATTACCAGTGTCACACTGCTCTCAGTGCCTTTGTTGTTGTGTTCGTATTTAGCTCTGTCGCAATAATTTGT
TTGGCCATTCTTTATAAAGTTCTCAAGTGCCTAAAGATTGCCCCAAGGAAAGTTCTGGATCCACTAATGTGGATTACTGTTTTCAT
CAGATGGGTGTATAAGAAGATGGTTGCCAGAGTAGCAGACAATATCAATCAGGTGAACAGGGAAATAGGATGGATGGAAGGAGGCC
AGCTGGCTCTAGGGAACCCTGCCCCTATTCCTCGTCATGCTCCAATTCCACGTTATAGCACATACCTAATGCTACTATTGATTGTC
TCATATGCATCAGCATGTTCAGAACTGTTCAGGCAAGCTCCAGAATCACCACTTGCTCCACAGAAGGTGTCAACACCAAGTGTAG
GCTGTCTGGCACAGCATTAATCAGGGCAGGGTCAGTTGGGGCAGAGGCTTGTTTGATGTTAAAGGGGGTCAAGGAAGACCAAACCA
AGTTTTTGAAGATAAAAACTGTCTCAAGTGAGCTATCGTGCAGGGAGGGCCAGAGCTATTGGACTGGGTCCTTTAGCCCTAAATGT
CTGAGCTCAAGGAGATGCCATCTTGTCGGGGAATGTCATGTGAATAGGTGTCTGTCTTGGAGAGACAATGAAACCTCAGCAGAATT
TTCATTTGTTGGGGAAAGCACGACCATGCGGGAGAACAAGTGTTTTGAGCAGTGTGGAGGATGGGGATGTGGGTGTTTCAATGTGA
ACCCATCTTGCTTATTTGTGCACACGTATCTGCAGTCAGTCAGAAAAGAGGCCCTTAGAGTTTTCAACTGTATCGATTGGGTGCAT
AAACTCACTCTAGAGATTACTGACTTTGATGGCTCTGTTTCAACAATAGACCTGGGAGCATCATCTAGCCGTTTCACAAACTGGGG
TTCAGTTAGCCTCTCACTGGACGCAGAGGGCATTTCAGGCTCAAACAGCTTTTCCTTCATTGAGAGCCCAGGCAAAGGGTATGCAA
TTGTTGATGAGCCATTCTCAGAAATTCCTCGGCAAGGGTTCTTGGGGGAGATCAGGTGCAATTCAGAATCTTCAGTCCTGAGTGCT
CATGAATCATGCCTTAGGGCACCAAATCTTATTTCATACAAGCCCATGATAGATCAGTTGGAGTGCACAACAAATCTGATTGATCC
CTTTGTTGTCTTTGAGAGGGGCTCTCTGCCACAGACAAGGAATGACAAAACCTTTGCAGCTTCAAAAGGAAATAGGGGTGTTCAAG
CTTTCTCTAAGGGCTCTGTACAGGCTGATCTAACACTGATGTTTGACAATTTTGAGGTGGACTTTGTGGGAGCAGCCGTGTCTTGT
GATGCCGCCTTCTTAAATTTGCACAGGTTGCTATTCCTGCAATGCAGGGGCCAGAGTCTGCCTGTCTATCACATCCACAGGAACTGG
AACTCTCTCTGCCCACAATAAAGATGGATCTCTGCATATAGTTCTTCCATCAGAGAATGGAACAAAAGATCAGTGTCAGATACTAC
ACTTCACTGTACCTGAGGTAGAGGAGGAGTTTATGTACTCTTGTGATGGAGATGAGCGGCCTCTGTTGGTGAAGGGAACCCTGATA
GCTATTGATCCATTTGATGATAGGCGAGAAGCAGGGGGGGAATCAACAGTTGTGAATCCAAAATCTGGATCTTGGAATTTCTTTGA
CTGGTTTTCTGGACTCATGAGTTGGTTTGGAGGGCCTCTTAAGACTATACTCCTCATTTGCCTGTATGTAGCATTATCAATTGGGC
TCTTTTTCCTTCTTATATATCTTGGAAGAACAGGCCTCTCTAAAATGTGGCTTGCTGCCACCAAGAAAGCCTCATAGGCGGCCGC

Figure 7
K

GAATTCTCTAGACACCATGGATAACTATCAGGAGCTGGCCATCCAGTTTGCCGCCCAGGCCGTGGACAGAAACGAGATCGAACAGT
GGGTGCGTGAGTTCGCTTACCAGGGTTTCGACGCCCGCCGGGTGATTGAACTGCTGAAGCAGTATGGAGGTGCCGACTGGGAGAAA
GACGCCAAGAAAATGATCGTGCTGGCTCTGACTAGAGGCAACAAGCCCAGGAGAATGATGATGAAGATGAGCAAGGAAGGAAAGGC
TACTGTGGAAGCCCTGATCAACAAGTACAAACTTAAGGAAGGAAACCCCTCTCGCGATGAACTGACTCTCAGCAGAGTGGCCGCAG
CCCTTGCCGGATGGACATGTCAGGCCCTGGTCGTGCTTTCCGAGTGGTTGCCCGTGACAGGAACCACCATGGACGGCCTGTCCCCA
GCATATCCCAGACATATGATGCATCCCTCTTTCGCCGGCATGGTCGACCCAAGTCTGCCTGAGGATTACCTCAGAGCCATCCTGGA
TGCCCACAGTCTTTACTTGCTGCAGTTTTCTCGGGTGATTAACCCCAACCCTCCGCGGAAGAACAAAGGAGGAGGTTGCAGCCACCT
TTACACAGCCCATGAACGCAGCTGTGAATAGTAACTTCATTTCTCACGAAAAACGACGCGAGTTCCTCAAAGCCTTCGGCCTGGTG
GACAGCAACGGAAAGCCTTCTGCAGCCGTCATGGCCGCCGCCCAGGCATACAAGACTGCCGCTTAAAAGCTTGCGGCCGC

Figure 7

L

CTCGAGACCATGGATTCTATATTATCAAAACAGCTGGTTGACAAGACTGGTTTTGTTAGAGTGCCAATCAAGCATTATGACTGTAC
AATGCTAACTCTGGCACTCCCAACATTTGATGTCTCCAAGATGGTAGATAGAATTACCATAGACTTCAATTTAGACGACATACAAG
GAGCATCTGAAATAGGCTCAACTTTGCTACCCTCTATGTCGATAGATGTGGAAGATATGGCCAATTTTGTTCACGATTTCACCTTT
GGCCACTTAGCTGACAAGACTGACAGACTCTTAATGCGTGAGTTTCCCATGATGAATGACGGGTTTGATCATCTGAGCCCTGACAT
GATTATCAAAACTACATCTGGCATGTATAACATCGTTGAGTTCACCACCTTTAGGGGGGATGAAAGAGGTGCATTCCAGGCTGCCA
TGACTAAACTCGCTAAGTATGAGGTTCCTTGTGAGAACAGATCTCAGGGCAGGACTGTTGTTCTTTATGTTGTTAGCGCCTACCGG
CATGGTGTTTGGTCTAATTTGGAGCTAGAGGACTCTGAAGCAGAGGAGATGGTATATAGGTACAGACTTGCCCTTAGTGTGATGGA
TGAGCTAAGGACCTTGTTCCCAGAACTGTCATCCACAGATGAGGAACTAGGAAAGACTGAGAGAGAGTTGCTAGCCATGGTCTCCT
CCATCCAAATAAATTGGTCAGTCACAGAATCTGTGTTTCCTCCCTTTAGCAGAGAAATGTTTGACAGGTTCAGATCTTCTCCTCCC
GATTCAGAGTACATCACGAGGATAGTGAGCAGATGCCTCATAAATTCTCAAGAGAAACTCATCAATAATTCCTTCTTTGCTGAAGG
GAATGATAAAGTTTTGAGATTTTCAAAAAACGCTGAGGAGTGTTCCTTGGCAATAGAGAGAGCTTTAAATCAGTATAGGGCAGAAG
ACAACCTTAGGGACCTAAATGACCACAAGTCTACTATTCAGCTGCCTCCCTGGCTGTCCTATCACGATGCCGATGGCAAAGATCTG
TGCCCTCTTCAGGGATTAGATGTGAGAGGAGACCATCCCATGTGCAACCTGTGGAGAGAAGTGGTTACCTCTGCAAATCTAGAGGA
GATTGAGAGGATGCACGATGATGCAGCGGCAGAACTTGAGTTTGCCCTTTCAGGGGTGAAGGACAGGCCAGATGAAAGAAACAGAT
ACCATAGAGTCCATCTGAATATGGACTCAGATGATAGTGTCTACATAGCTGCTTTAGGGGTTAATGGAAAGAAGCATAAAGCAGAC
ACATTAGTGCAACAAATGAGAGACAGGAGCAAACAGCCCTTCTCTCCAGATCATGATGTGGATCACATATCTGAATTTCTCTCTGC
ATGCTCTAGTGACTTGTGGGCAACAGATGAGGACCTATACAACCCTCTCTCTTGTGATAAAGAGCTTAGATTGGCAGCTCAGAGAA
TTCATCAGCCATCCTTATCAGAAAGGGGCTTCAATGAGATTATAACAGAGCACTACAGATTTATGGGAAGTAGGATAGGATCATGG
TGCCAAATGGTCAGTTTAATAGGAGCTGAGCTATCAGCTTCTGTAAAGCAACATGTTAAGCCTAACTATTTTGTGATTAAACGACT
ACTAGGTTCTGGGATTTTCTTGCTGATCAAGCCTACTTCCAGCAAAAGCCATATATTCGTGTCTTTTGCAATTAAGCGCTCTTGCT
GGGCCTTTGATCTCTCCACTTCCAGGGTTTTCAAACCCTACATAGATGCCGGGGATCTGTTAGTTACTGACTTTGTTTCTTACAAA
CTAAGTAAGCTTACCAACCTCTGCAAGTGCGTTTCGTTAATGGAATCCTCCTTCTCATTTTGGGCAGAGGCATTTGGGATTCCAAG
CTGGAACTTTGTTAGTGACTTGTTCAGGTCTTCAGACTCTGCAATGGATGCCTCATACATGGGCAAACTCTCTTTATTAACCC
TTTTGGAAGACAAAGCAACAACTGAAGAGTTACAGACTATTGCAAGATATATAATCATGGAGGGCTTTGTCTCGCCCCCAGAAATC
CCAAAACCTCACAAGATGACCTCTAAGTTTCCCAAGGTTCTCAGGTCAGAGCTGCAGGTTTACTTATTAAACTGCTTATGCAGAAC
TATCCAGAGAATAGCAGGTGAGCCCTTTATTCTTAAGAAGAAGGATGGGTCTATATCCTGGGGTGGCATGTTTAATCCTTTTTCAG
GGCGTCCACTGCTTGATATGCAACCACTCATCAGCTGTTGTTACAATGGTTACTTTAAAAACAAAGAAGAAGAGACTGAGCCTTCC
TCCCTTTCTGGGATGTATAAGAAAATTATAGAACTTGAGCACCTTAGACCACAGTCAGATGCCTTCTTGGGTTATAAAGATCCAGA
ACTACCTAGAATGCATGAGTTCAGTGTTTCCTACTTGAAGGAGGCTTGCAATCATGCTAAGCTGGTCTTAAGGAGTCTCTATGGAC
AGAATTTCATGGAGCAAATAGACAACCAAATTATTCGAGAGCTCAGTGGGTTGACTCTAGAAAGATTAGCCACACTTAAGGCCACA
AGCAACTTTAATGAGAATTGGTATGTCTATAAGGATGTGGCAGACAAGAACTACACAAGGGATAAATTATTAGTGAAGATGTCAAA
ATATGCTTCTGAGGGAAAGAGCCTAGCTATCCAGAAGTTTGAGGATTGCATGAGGCAGATAGAGTCACAAGGATGTATGCACATTT
GTTTGTTTAAGAAACAACAGCATGGAGGTCTGAGAGGATCTGAGAGAAGAATTGTTCAATCGGTGGTGGAG
ACAATAGCCAGGTCTATAGGGAAGTTCTTTGCTTCTGATACCCTCTGTAACCCCCCCAATAAGGTGAAAATTCCTGAGACACATGG
CATTAGGGCTCGGAAGCAATGTAAGGGGCCTGTGTGGACTTGTGCAACATCAGATGATGCAAGGAAGTGGAACCAAGGCCATTTTG
TTACAAAGTTTGCCCTCATGCTATGTGAGTTCACCTCTCCTAAGTGGTGGCCATTGATCATTAGGGGATGTTCAATGTTTACCAGG
AAAAGGATGATGATGAATTTGAATTATCTTAAGATCCTGGATGGTCATCGAGAGCTTGATATTAGAGATGACTTTGTGATGGATCT
CTTCAAAGCTTATCATGGTGAGGCAGAAGTTCCATGGGCTTTTAAGGGTAAAACATATCTGGAAACCACGACAGGGATGATGCAGG
GGATATTGCATTATACTTCCTCATTATTACACACCATTCATCAAGAATACATCCGGTCCTTGTCCTTTAAAATATTCAACCTGAAG
GTTGCTCCTGAGATGAGCAAAAGCCTGGTTTGTGACATGATGCAAGGATCAGATGATAGTAGCATGCTAATCAGCTTCCCAGCTGA
TGACGAGAAGGTTCTCACCAGATGCAAAGTGGCCGCAGCCATATGCTTCCGAATGAAGAAGGAGCTGGGAGTGTACCTTGCCATCT
ACCCCTCAGAGAAGTCCACAGCAAACACAGATTTTGTGATGGAGTACAATTCTGAATTTTATTTCCACACCCAGCATGTTAGACCG
ACGATCAGGTGGATTGCAGCATGTTGCAGCCTGCCAGAAGTGGAAACACTAGTAGCCCGCCAGGAAGAGGCCTCTAATCTAATGAC
TTCAGTTACTGAGGGGGGTGGGTCATTCTCCTTAGCTGCAATGATTCAGCAAGCTCAGTGCACTCTCCATTACATGCTAATGGGCA
TGGGAGTGTCTGAGCTATTCTTAGAGTATAAGAAGGCAGTGCTGAAGTGGAATGAACCCTGGTCTGGGTTTCTTCCTGCTTGACAAT
CCTTATGCGTGCGGGTTGGGAGGTTTTAGATTTAATCTCTTCAAAGCCATCACCGAACTGATTTGCAGAAGCTATATGCTTTCTT
CATGAAGAAGGTTAAGGGCTCAGCTGCTAGGGACTGGGCAGATGAGGATGTTACCATCCCAGAAACGTGTAGCGTGAGCCCAGGTG
GCGCTCTAATTCTTAGCTCCTCTCTAAAGTGGGGATCTAGGAAGAAGTTTCAGAAACTGAGAGACCGTTTGAACATACCAGAGAAC
TGGATTGAGCTAATAAATGAGAATCCAGAGGTGCTCTATCGAGCTCCCAGAACAGGCCCCAGAAATATTGTTGCGCATTGCAGAGAA
AGTCCATAGCCCTGGTGTTGTGTCATCATTGTCTTCTGGCAATGCAGTCTGTAAAGTCATGGCCTCAGCTGTATACTTCTTATCAG
CAACAATTTTTGAAGACACTGGACGCCCTGAGTTCAACTTCTACAAAGTACAGCTTGCTACAAAAGATGGCCGCATAT
TCTGGCTTTCATGGTTTCAATGATATGGAGCCAGAAGTATATATTATTCCTATTCCCGAACATTGAGGAATTAGAATCACTGGATTC
TATAGTTTACAACAAGGGAGAAAATAGACATCATCCCAAGAGTTAATATCAGGGATGCAACCCAAACCAGGGTCACTATCTTTAATG
AGCAGAAGACCCTCCGAACATCTCCAGAGAAGTTGGTGTCAGACAAGTGGTTCGGGACTCAGAAGAGACAACTCTAGCTCACACTCCACTGAA
TTCCTGGCTGAATGGGAGAAGCTAAAGAAAATTGTGAAGTGGTTGGAAGACACTCCAGAAGCAACTCTAGCTCACACTCCACTGAA
TAACCATATTCAGGTTAGGAATTTCTTTGCTAGAATGGAAACAAGCCTAGAACGGTTAGAATAACAGGAGCTCCTGTAAAGAAGA
GGTCAGGGGTTAGCAAGATAGCTATGGTTATCCGTGACAATTTCTCCCGGATGGGCCATCTTAGAGGTGTAGAAGACCTCGCTGGC
TTCACTCGTAGTGTGTCAGCTGAAATCCTCAAGCACTTTCTGTTCTGCATACTACAGGGTCCATACAGTGAGAGCTATAAGCTACA
GCTAATCTACAGAGTCCTAAGCTCAGTGTCAAACGTTGAGATAAAGGAATCGGATGGTAAGACAAAAACCAATTTGATTGGGATCC
TTCAGAGATTTCTAGATGGTGATCACGTTGTCCCTATAATTGAAGAGATGGGAGCCGGAACAGTGGGTGGATTCATCAAGAGACAA
CAGTCTAAGGTTGTGCAAAATAAAGTGGTCTATTATGGAGTTGGGATCTGGAGAGGCTTCATGGATGGATATCAGGTCCATCTTGA
GATAGAAAATGACATAGGACAGCCCCCAAGGCTTAGGAATGTCACAACTAACTGTCAGAGCAGCCCATGGGATCTGAGTGTCCCAA
TAAGGCAGTGGGCAGAAGACATGGGGGTCACAAACAACCAGGATTATTCCTCTAAATCTAGCAGAGGAGCTAGATATTGGATGCAT
TCATTTAGGATGCAAGGACCCAGCAACCATTTGGATGCCCAGTTTATATTATTAAGGGTGACATGTCAGATGTTATCAGACTGAG
AAAAGAGGAGGTGGAGATGAAAGTACGGGGCTCTACTCTCAACTTGTACACTAAGCACCATTCTCATCAAGACTTACACATTTTAT
CTTACACTGCATCAGACAATGATCTCAGTCCAGGCATTTTCAAGTCAATATCAGATGAGGGAGTAGCTCAAGCCCTGCAGTTATTT
GAGAGGGAGCCAAGCAACTGCTGGGTGAGATGTGAGTCTGTAGCTCCAAAATTCATATCAGCCATCCTTAGCAGATATGTGAGGGAA
GAGACAGATAAAAGGAATCAACAGAACCAGACTCTCAGAGATTGTGAGAATTTGTTCTGAATCTTCCCTAAGATCAAAGGTCGGAT
CTATGTTCTCATTTGTCGCCAATGTTGAGGAGGCCCATGATGTTGATTATGATGCGTTAATGGATCTAATGACAGAAGATGCTAAG
AACAATGCATTCAGTCATGTTGTCGATTGCATAGAGTTGGATGTCCTTACGAGATGGAGTCTTTTGATCAGATCATCTGATGT
CAACCTCTTTGGGCCAGCCCATTACAAGGACATCAGTTCATTATCTATGATTGCTCATCCCTTAATGGATAAGTTTGTTGATTATG
CCATTTCCAAGATGGGGAGAGCCTCAGTTAGAAAAGTTCTAGAGACAGGTCGGTGCTCTAGCAAAGACTATGATTTATCAAAGGTT
CTCTTCAGAACTCTACAGAGACCAGAAGAGAGCATTAGGATAGATGATCTGGAGTTATATGAGGAGACAGATGTGGCGGATGACAT
GCTAGGCTAAGCGGCCGC

Figure 17

METHODS TO PRODUCE BUNYAVIRUS REPLICON PARTICLES

RELATED APPLICATIONS

This application is the U.S. National Stage of International Application No. PCT/NL2011/050631, filed Sep. 20, 2011, published in English, and claims the benefit of European Application Number 10177709.2, filed on Sep. 20, 2010 and U.S. Application No. 61/468,597, filed on Mar. 29, 2011, the entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 18, 2014, is named P92482US10seqlist_ST25 and is 75,177 bytes in size.

FIELD

The invention relates to the field of recombinant viruses. More specifically, the invention relates to methods for generating recombinant bunyavirus particles that are incapable of autonomous spread. The resulting bunyavirus particles can be used as a vaccine to protect a mammal against infectious disease mediated by bunyavirus, and can be used as vector for the transduction of a foreign gene.

The Bunyaviridae family is divided into five genera, of which four (*Orthobunyavirus, Nairovirus, Phlebovirus* and *Hantavirus*) include numerous virus species that are capable of causing severe disease in both animals and humans. Well known examples are hantaanvirus (HTNV, *Hantavirus* genus), Crimean-Congo hemorrhagic fever virus (CCHFV, *Nairovirus* genus) and Rift Valley fever virus (RVFV, *Phlebovirus* genus).

In the veterinary field, RVFV is one of the most feared bunyaviruses. Transmission of RVFV between ruminants occurs via the bite of infected mosquitoes, whereas infection of humans is believed to occur predominantly via aerosols released from contaminated animal products. Mortality rates in adult ruminants vary from 10 to 20%. Mortality rates in unborn and young animals can be more dramatic, approaching 100%. Although the human mortality rate is historically estimated at about 2%, considerably higher mortality rates were reported after recent outbreaks. Although the virus is currently confined to the African continent and the Arabian Peninsula, mosquitoes that transmit RVFV are not restricted to these areas. This explains the growing concern for RVFV incursions into other parts of the world, including Europe, Asia and the Americas.

Bunyavirus family members contain a three-segmented RNA genome, which is comprised of a large (L), a medium (M) and a small (S) segment. All family members produce the structural nucleocapsid (N) protein from the S genome segment, the viral polymerase protein from the L genome segment and the G1 and G2 structural glycoproteins from the M genome segment. Nonstructural proteins are encoded by the S (referred to as NSs) and M segments (referred to as NSm) of *phleboviruses* and *orthobunyaviruses*. Interestingly, the M segment of *nairoviruses* encodes several structural as well as non-structural proteins and glycoprotein synthesis and processing of these viruses is quite distinct from other members of the Bunyaviridae family. However, the skilled person is without any doubts able to apply the teachings of the present invention for the generation of *nairoviruses* replicon particles.

The RVFV M segment encodes the structural glycoproteins G2 (generally referred to as Gn) and G1 (generally referred to as Gc) and at least two non-structural proteins, which are collectively referred to as NSm. The M segment encodes a singly mRNA with multiple translation initiation sites. The translation products are Gn, Gc and the at least two NSm proteins. The viral genomic segments contain untranslated regions (UTRs) on both the 3' and the 5' ends that serve as promoters for replication of the segment and for transcription of the encoded reading frames.

The recent establishment of a reverse-genetics system for RVFV has provided important new insights into its biology. A few years after the first successful rescue of the complete RVFV from cloned cDNA, Habjan et al. described the packaging of a reporter minigenome into virus-like particles (VLPs) (Habjan et al. 2009. Virology 385, 400-408). The VLPs were produced by transient expression of the NSm, Gn, Gc, N and L proteins in the presence of a reporter minigenome. The N and L proteins induced expression of a reporter protein from the replicated minigenome and the structural glycoproteins subsequently packaged the minigenome into VLPs. These VLPs were shown to transport the reporter minigenome to receiving cells. Whereas primary transcription in these cells was observed, replication of the minigenome was dependent on the production of the N and L proteins from transfected plasmids. Cells that are only infected with the VLPs and which are not cotransfected with constructs expressing N and L proteins, show limited expression of viral protein. The viral genome is not replicated and there is no amplification of the genome in these cells. Therefore, only primary transcription of the viral genome occurs in these cells.

Although RVFV, HTNV and CCHFV cause severe disease with high case fatality in humans, no vaccines are available for the prevention of these diseases in humans, and no antiviral agents are registered for post-exposure treatment. The development of such control tools is severely complicated by the fact that these viruses must be handled under high biosafety containment. RVFV also causes severe disease with high case fatality in livestock. Effective, but not safe, vaccines are registered for use outside the African continent.

Therefore, there is an urgent need to develop methods and means for safe and efficient production of bunyavirus particles.

The present invention discloses non-spreading bunyavirus replicon particles that are capable of autonomous genome replication. Bunyavirus replicon particles (BRPs) were produced by trans-complementation of the structural glycoproteins G1 (G1 of RVFV is referred to as Gc) and G2 (G2 of RVFV is referred to as Gn) in both the presence and absence of the NSm coding-regions. BRPs were produced up to titers of 10E7 infectious particles/ml. The resultant particles can be used to study all aspects of the viral life cycle outside biosafety containment facilities both in vitro and in vivo. Furthermore, the particles can be used in virus-neutralization tests that can be performed outside biosafety containment facilities and the antigens produced can be used for ELISAs and other serological tests. Moreover, the methods described here will facilitate the development of therapeutics and vaccines that optimally combine the safety of inactivated vaccines with the efficacy of live-attenuated vaccines. The methods can also be applied for the establishment of novel gene-delivery systems.

In a first aspect, the invention provides a method for generating a recombinant non-spreading BRP, the method comprising: A) providing a eukaryotic cell with growth medium; B1) providing the eukaryotic cell with sufficient DNA-dependent RNA polymerase, for example T7 polymerase; B2) providing the eukaryotic cell with sufficient bunyavirus (NSm) GnGc protein; B3) providing the eukaryotic cell with a vector that comprises a copyDNA (cDNA) of a bunyavirus L genome segment which is flanked at the 5' end by a T7 promoter, and at the 3' end with cDNA encoding a ribozyme sequence; B4) providing the eukaryotic cell with a vector that comprises a cDNA of a Bunyavirus S genome segment or part of a Bunyavirus S genome segment at least comprising the N gene and the 3' and 5' UTRs, which are flanked at the 5' end by a T7 promoter and at the 3' end with cDNA encoding a ribozyme sequence; and, optionally, B5) providing the eukaryotic cell with a vector that comprises a cDNA of a Bunyavirus M genome segment from which the GnGc coding region has been functionally inactivated, the cDNA encoding the genome segment in between the 3' and 5' UTRs is flanked at the 5' end by a T7 promoter and at the 3' end with cDNA encoding a ribozyme sequence; C) generating a recombinant Bunyavirus replicon particle which can be isolated from the growth medium; wherein the sequence of steps of B1, B2, B3, B4 and B5 is random and all or part of these steps may be performed simultaneously.

The cDNAs of the bunyavirus L, S and M genome segments are present in the vector in the genomic sense orientation or in the antigenomic sense orientation. When the cDNAs of the bunyavirus L, S and M genome segments are present in the vector in the genomic sense orientation, it is preferred that the cells are provided with plasmids that produce the N and L proteins.

The cDNAs of the bunyavirus genome segments in a method for generating a recombinant bunyavirus replicon particle according to the invention are flanked at the 5' end by a promoter sequence for a DNA-dependent RNA polymerase. Said promoter sequence for a DNA-dependent RNA polymerase is selected from any known promoter sequences of DNA-dependent RNA polymerases such as, but not limited to, the promoter sequence of a eukaryotic RNA polymerase I such as, for example, a promoter for murine RNA polymerase I, SP6, T3 and T7. For example, a method according to the invention in which a eukaryotic cell is provided with sufficient T3 polymerase and in which Bunyavirus genomic segments are flanked by a T3 promoter sequence or a method according to the invention in which a eukaryotic cell is provided with sufficient SP6 polymerase and in which cDNA encoding bunyavirus genomic segments are flanked by a SP6 promoter sequence, are also provided by the invention. T7 is a preferred DNA-dependent RNA polymerase. Although the description and the claims refer to T7 polymerase, it is to be understood that the invention is not limited to T7 polymerase but includes other DNA-dependent RNA polymerase such as, for example, T3 polymerase and SP6 polymerase. A preferred promoter sequence for a T7 polymerase is TAATACGACTCACTATAG.

Copy DNA of bunyavirus genomic segments or fragments thereof are flanked at the 3' ends by a cDNA encoding a ribozyme sequence that mediates 3' end formation of the RNA by self-cleavage of the nascent RNA. A preferred ribozyme sequence is a hepatitis delta virus (HDV) ribozyme sequence. A termination sequence that mediates termination of the DNA-dependent RNA polymerase may further be present distal to the cDNA encoding the ribozyme sequence. In a preferred embodiment, the DNA-dependent RNA polymerase is T7 polymerase and the termination sequence is a T7 transcription termination sequence. Promoter sequences for DNA-dependent RNA polymerases, such as T7 polymerase, and termination sequences such as a T7 transcription termination sequence, are known to the skilled person.

The term "recombinant bunyavirus replicon particle" refers to a bunyavirus particle that comprises at least a bunyavirus L-genome segment and (at least) a part of a bunyavirus S genome segment comprising the N-gene and the 3' and 5' UTRs. These genomic segments encode the proteins that are required for transcription and replication of these viral genomic segments in an infected cell, resulting in replication and thus amplification of the L and S genome segments in an infected cell. Cells that are infected with a recombinant bunyavirus replicon particle according to the invention express high levels of at least the bunyavirus L and N proteins.

The term "L-genome segment" refers to a substantially complete L-genome segment. The term "substantially complete" is used to indicate that the L genome segment comprises cis-acting elements that mediate replication of the L genome segment and that mediate functional expression of the L-gene. The term "substantially complete" indicates that sequences that are not involved in replication of the L genome segment or in functional expression of the L-gene may be deleted or substituted. The term "functional expression" refers to expression of an L protein, a viral RNA-dependent RNA polymerase, that is able to mediate replication and transcription of a bunyavirus genome segment or bunyavirus minigenome. The term "minigenome" refers to an RNA molecule that comprises the 5' and 3' regions of a bunyavirus genome segment that function in replication of the segment, but which lacks at least one bunyavirus coding region that is present on the wildtype genome segment. A minigenome may further comprise a foreign gene such as, but not limited to, a marker gene such as a Fluorescent Protein, beta-glucuronidase and beta-galactosidase. The term "L genome segment from which the L coding region has been functionally inactivated" refers to an L genome segment, comprising the 3' and 5' UTRs of the L genome segment.

The term "S genome segment comprising the N gene" refers to an S genome segment, comprising the untranslated regions of both the 3' and the 5' end of the S genome segment and at least the nucleotide sequences for expression of the N protein, such as nucleotide sequences for transcription of the N-gene and translation of the N-gene-transcript. The term "S genome segment from which the NSs and N coding regions have been functionally inactivated" refers to an S genome segment, comprising the 3' and 5' UTRs and the untranslated intergenic region of the S genome segment.

The term "M genome segment from which the GnGc coding region has been functionally inactivated" refers to an M genome segment, comprising the untranslated regions of both the 3' and the 5' end of the M genome segment.

Bunyavirus L-, S- and M-genome segments are preferably cloned in standard eukaryotic expression vectors, whereby the genome segments are flanked by a DNA-dependent RNA polymerase promoter, preferably a T7 promoter, and a HDV ribozyme sequence. Suitable vectors comprise pBluescript (Stratagene), pUC plasmids such as preferably pUC57 (Genscript), and medium and low-copy number vectors such as pBR322 and derivates thereof (Mobitec, Germany), pACYC184 (Chang and Cohen, 1978) and pCC1 (Epicentre Biotechnologies, Madison, Wis.). Some Bunyavirus genome segments, especially L-genome segments, are more stable when cloned in medium or low copy number vectors preferably pCC1.

The term functionally inactivated refers to a gene of which the activity of the encoded RNA or protein is less than 10% under the same conditions of the activity of the encoded RNA or protein of a gene that is not functionally inactivated, more preferred less than 5%, more preferred less than 2%, more preferred less than 1%. The term "functionally inactivated" most preferably indicates a gene that is not expressed because it is not transcribed or not translated, or a gene of which the encoded protein is not active, for example by alteration or deletion of one or more nucleotides within the coding region of the gene. The term "functionally inactivated gene" preferably is a gene of which part or all of the coding sequences have been deleted.

The order in which a eukaryotic cell is provided with sufficient T7 polymerase, sufficient bunyavirus (NSm)GnGc protein, a bunyavirus L genome segment, a bunyavirus S genome segment comprising at least the N-gene and, optionally, a Bunyavirus M genome segment from which the (NSm)GnGc coding region has been functionally inactivated, is random. All or part of these steps may be performed subsequent to one another, or simultaneously. It will be clear to the skilled person that the bunyavirus L genome segment and/or a bunyavirus S genome segment may comprise a functional deletion of the L-gene and/or N-gene, respectively, when the cell is provided with RNA polymerase enzyme that is encoded by a Bunyavirus L-genome segment and/or a N protein that is encoded by a bunyavirus S-genome segment.

For practical reasons, it is preferred that a eukaryotic cell is provided first with a bunyavirus L genome segment, a bunyavirus S genome segment comprising the N-gene and, optionally, a bunyavirus M genome segment from which the (NSm)GnGc coding region has been functionally inactivated, The resulting cell line harbouring a Bunyavirus L genome segment, a bunyavirus S genome segment comprising the N-gene and, optionally, a bunyavirus M genome segment from which the (NSm)GnGc coding region has been functionally inactivated, is subsequently provided with sufficient bunyavirus (NSm)GnGc protein to mediate efficient packaging of the bunyavirus genome segments into BRPs.

Alternatively, a cell line is first provided with sufficient T7 polymerase and sufficient bunyavirus (NSm)GnGc protein by infection or transfection of a construct encoding these proteins, followed by provision of the cell with a bunyavirus L genome segment, a bunyavirus S genome segment comprising the N-gene and, optionally, a bunyavirus M genome segment from which the (NSm)GnGc coding region has been functionally inactivated.

The term "sufficient T7 polymerase" refers to the amount of T7 polymerase that is provided to a eukaryotic cell that is sufficient to mediate efficient transcription of cDNA molecules encoding the bunyavirus L genome segment and the complete S genome segment or the part of a bunyavirus S genome segment at least comprising the N gene, that are flanked by a T7 promoter sequence and cDNA encoding a HDV ribozyme. It was found that rescue of a bunyavirus by providing a eukaryotic cell stably expressing T7 RNA polymerase under control of a cytomegalovirus promoter such as, for example, the BSR T7/5 cell line (Buchholz et al. 1999. J. Virol. 73: 251-259) with one or more vectors that comprise a bunyavirus L genome segment, a bunyavirus M genome, and/or a bunyavirus S genome segment, or functional parts of one or more of the bunyavirus genome segments, was inefficient.

An improved and reproducible rescuing efficiency was obtained when eukaryotic cells were freshly infected or transfected with an expression vector that encodes the T7 polymerase.

Therefore, in a preferred method according to the invention, the eukaryotic cell is provided with sufficient T7 polymerase by freshly transfecting or infecting the eukaryotic cell with an expression vector that encodes the T7 polymerase.

In one embodiment, the expression vector is a plasmid that encodes the T7 polymerase. Suitable plasmids are, for example, pCAGGS, and pcDNA. In a preferred embodiment, the expression vector is a recombinant virus or viral vector that encodes the T7 polymerase. A suitable virus or viral vector is, for example, a replication defective retroviral vector such as a lentiviral vector, for example a HIV-based vector or an EIAV-based vector, or a replication defective MMLV-based vector. A further suitable virus or viral vector is provided by a replication defective adenoviral vector and a baculoviral vector. A preferred virus or viral vector is a replication defective poxvirus such as, for example, a vaccinia-based virus. In a most preferred method according to the invention, the eukaryotic cell is provided with sufficient T7 polymerase by infecting the eukaryotic cell with a fowlpoxvirus (FPV)-based expression vector that encodes the T7 polymerase. The FPV may be replication competent or replication defective.

Without being bound by theory, a reason for the improved and reproducible rescuing efficiency by using a FPV-based expression vector is that the level of T7 polymerase is sufficiently high to allow efficient transcription of the bunyavirus cDNA genome segments. A further reason could be that FPVs produce their own capping enzyme. Capping of the T7 transcripts could stabilize the bunyaviral RNA that is produced from the cDNA, protecting the RNA from degradation.

A further advantage of a FPV is that it belongs to the genus *Avipoxvirus* and is capable of spreading in avian cells. In non-avian cells such as, for example, mammalian cells, FPV replication is abortive with no evidence of production of infectious virus. Therefore, when the eukaryotic cell is a non-avian eukaryotic cell, a replication competent FPV-based expression vector or a replication deficient FPV-based expression vector is preferably used for a method of the invention. When the eukaryotic cell is an avian eukaryotic cell, it is preferred that a replication deficient FPV-based expression vector is used for a method of the invention.

The term "providing (NSm)GnGc protein" indicates that at least the bunyavirus Gn and Gc proteins are provided. In addition to the Gn and Gc protein, also one or more NSm proteins may be provided.

The term "sufficient bunyavirus (NSm)GnGc protein" refers to the amount of (NSm)GnGc proteins that are provided to a eukaryotic cell that is sufficient to mediate efficient packaging of the bunyavirus genome segments in a recombinant bunyavirus replicon particle. A cell can be provided with sufficient bunyavirus (NSm)GnGc proteins by transfecting or infecting the cell with a vector that mediates expression of the bunyavirus (NSm)GnGc proteins. If a Bunyavirus M genome segment from which the (NSm)GnGc coding region has been functionally inactivated, is present in the eukaryotic cell, it is preferred that there is no sequence overlap between the bunyavirus (NSm)GnGc protein-encoding sequence in the eukaryotic cell and the bunyavirus M genome segment to prevent the generation of a packaging-competent bunyavirus.

A eukaryotic cell is preferably provided with sufficient bunyavirus (NSm)GnGc proteins by transfecting the eukaryotic cell with an expression plasmid encoding the bunyavirus (NSm)GnGc proteins. Said expression plasmid preferably comprises a promoter region comprising regulatory sequences that control the expression of the bunyavirus (NSm)GnGc proteins. Suitable promoter sequences are known in the art, including, but not limiting to, promoter sequences from a virus such as cytomegalovirus (CMV), or a promoter region from a housekeeping gene such as beta-actin, for example a chicken actin promoter. If introduction of such expression vector(s) results in death of cells that produce high levels of the proteins due to their toxicity, end-point dilution yields clones that express tolerable levels of these proteins. It was found that the selected cells were tolerable for higher expression levels provided by subsequent (re)introduction of (NSm)GnGc-producing expression vector(s).

The invention further provides a eukaryotic replicon cell line expressing (NSm)GnGc-proteins and comprising the bunyavirus L genome segment and the bunyavirus S genome segment or at least part of a bunyavirus S genome segment comprising the N-gene and the 3' and 5' UTRs. It was found that low levels of (NSm)GnGc was sufficient to prevent loss of the bunyavirus genome segments from the cells. Without being bound by theory, expression of the (NSm)GnGc-proteins, albeit at low levels, allowed production of BRPs which continuously re-infected cells. To produce BRPs, the eukaryotic replicon cell line is provided with sufficient bunyavirus (NSm)GnGc protein by repetitive introduction of a vector providing bunyavirus (NSm)GnGc protein.

In a more preferred embodiment, the eukaryotic cell in a method according to the invention is provided with bunyavirus (NSm)GnGc proteins by infecting the eukaryotic cell with a viral vector that transduces the bunyavirus (NSm)GnGc proteins. In one embodiment, said viral vector is an adenovirus-based vector, a retrovirus-based vector or a herpesvirus-based vector. A preferred viral vector that transduces the bunyavirus (NSm)GnGc proteins is a paramyxovirus-based vector. A preferred paramyxovirus is of the genus *Avulavirus*, which includes avian paramyxovirus. A preferred avian paramyxovirus is Newcastle disease virus (NDV). A preferred NDV comprises a recombinant cDNA clone of NDV strain LaSota, named NDFL (Peeters et al. 1999. J. Virol. 73: 5001-5009), in which a codon-optimized GnGc gene is flanked by newly introduced transcription start and stop sequences (Kortekaas et al. 2010. Vaccine 28:4394-4401). A further preferred NDV is a vector derived from a recombinant virulent strain such as, for example, GB Texas, Italien, Milano and Herts '33/56, that transduces (NSm)GnGc proteins. The vector preferably is a non-replicative or non-spreading NDV. A preferred vector comprises a genome from a recombinant virulent NDV strain with a deletion in the gene encoding the HN-protein. The viral vector is produced in a cell line that trans-complements the HN protein.

In a further preferred embodiment, the eukaryotic cell is provided with bunyavirus (NSm)GnGc proteins by infecting the eukaryotic cell with a recombinant viral vector that transduces the bunyavirus (NSm)GnGc proteins, followed by selection of a cell in which the recombinant viral vector is persistently present without causing overt cytopathogenic effect. Proteins encoded by the virus such as, for example, bunyavirus (NSm)GnGc proteins, are expressed during the persistent infection. It was found that a persistently infected cell tolerates higher expression levels of bunyavirus GnGc proteins, compared to a cell that is stably transformed with an expression vector expressing bunyavirus GnGc proteins.

A preferred viral vector for generating a persistently infected cell is based on a herpesvirus, for example a herpes simplex virus, Epstein-Bar virus, or varicella zoster virus, on a retrovirus such as, for example HIV, EIAV, or MMLV, or on a paramyxovirus, for example an *Avulavirus*, which includes avian paramyxovirus. A preferred avian paramyxovirus is Newcastle disease virus (NDV). A preferred NDV comprises a recombinant cDNA clone of NDV strain LaSota, named NDFL (Peeters et al. 1999. J. Virol. 73: 5001-5009), in which a codon-optimized GnGc gene is present flanked by newly introduced transcription start and stop sequences (Kortekaas et al. 2010. Vaccine 28:4394-4401).

A eukaryotic cell may be transiently or stably expressing bunyavirus (NSm)GnGc proteins. It was found initially that a eukaryotic cell that was stably transformed with an expression plasmid mediating high expression levels of bunyavirus (NSm)GnGc proteins could not be obtained. This may in part be explained by our observation that constitutive high expression levels of GnGc might not be tolerated in eukaryotic cells. However, expression from a virus that persistently infected these eukaryotic cells was tolerated.

To enable the generation of a stable cell line, a eukaryotic cell is preferably provided with bunyavirus (NSm)GnGc proteins by transfecting or infecting the eukaryotic cell with an expression vector that provides conditional expression of the bunyavirus (NSm)GnGc proteins. The term "conditional expression" is known to the skilled person and refers to a controlled expression of a protein, which is not, or only at low level expressed under a first condition, but of which the expression is increased under a second condition.

In a preferred conditional expression system, expression of bunyavirus (NSm)GnGc proteins is dependent on the presence of an inducer or the absence of an inhibitor. Several inducible gene expression systems are currently available that can be used to control expression of (NSm)GnGc proteins. Tet-On and Tet-Off expression systems (for example Tet-On® and Tet-Off® Advanced Inducible Gene Expression Systems, Clontech) can be used for inducible expression of a gene of interest. In these systems expression of the transcriptional activator (tTA) is regulated by the presence (Tet-On) or absence (Tet-Off) of tetracycline (TC) or a derivative of tetracycline such as doxycycline (dox). The tTA is composed of the *Escherichia coli* Tet repressor protein (TetR) and Herpes simplex virus transactivating domain VP16. tTA regulates transcription of a gene of interest under the control of a tetracycline-responsive element (TRE) consisting of the Tet operator (TetO) DNA sequence and a promoter sequence, for instance the human cytomegalovirus (hCMV) promoter (Baron, U. and Bujard, H. Methods Enzymol 327, 401-421 (2000)). A gene encoding bunyavirus (NSm)GnGc is positioned downstream of the tetracycline-responsive element.

In the Tet-Off system, tTA binds to TRE in the absence of TC or dox (Gossen, M. and Bujard, H. Proc Natl Acad Sci USA 89, 5547-5551 (1992)) and transcription of bunyavirus (NSm)GnGc proteins is activated, whereas tTA cannot bind TRE in the presence of TC or dox and expression is inhibited. In contrast, the Tet-On system uses a reverse tTA (rtTA) that can only bind the TRE in the presence of dox (Gossen, M. et al. Science 268, 1766-1769 (1995)). Transcription of bunyavirus (NSm)GnGc proteins is inhibited in the absence of TC or dox and activated in the presence of TC or dox.

In another embodiment, conditional expression is executed using a hormone inducible gene expression system such as, for instance, an ecdysone inducible gene expression system (for example RheoSwitch®, New England Biolabs) (Christopherson, K. S. et al. Proc Natl Acad Sci USA 89, 6314-6318 (1992)). Ecdysone is an insect steroid hormone. In cells expressing the ecdysone receptor, a heterodimer consisting of the ecdysone receptor (Ecr) and retinoid X receptor (RXR) is formed in the presence of an ecdysone agonist. An exdysone agonist can be selected from ecdysone, one of its analogues such as muristerone A and ponasterone A, and a non-steroid ecdysone agonist. In the presence of an agonist, Ecr and RXR interact and bind to an ecdysone response element that is present on an expression cassette. Transcription of a protein that is placed in an expression cassette downstream of the ecdysone response element is thus induced by exposing the cell to an ecdysone agonist.

It will be clear to the skilled person that a eukaryotic cell line can be obtained that expresses sufficient bunyavirus (NSm)GnGc proteins by transfecting or infecting the eukaryotic cell with a vector that mediates conditional expression of the bunyavirus (NSm)GnGc proteins. Said vector preferably is a viral vector, for example derived from a paramyxovirus such as a Newcastle disease virus, or, more preferred, an extra chromosomal DNA molecule which is capable of replicating independently from the chromosomal DNA such as a plasmid.

In a preferred method according the invention, one or more of the bunyavirus L genome segment, the S genome segment, and/or, when present, the M genome segment comprises a foreign gene. Said foreign gene is preferably derived from an organism that is a transmitter of an infectious disease. Said organism is preferably selected from adenovirus, African horsesickness virus, African swine fever, Bluetongue virus, Border disease virus, Borna virus, Bovine viral diarrhoe virus, Bovine respiratory syncytial virus, Cache Valley fever virus, Chikungunya virus, Chrysomya bezziana, Classical swine fever, Crimean-Congo hemorrhagic fever virus, Nairobi sheep disease virus, *Cochliomyia hominivorax*, Coronavirus, Cytomegalovirus, Dengue virus, Eastern equine encephalitis virus, Ebola virus, Equine encephalomyelitis virus, Equine encephalosis virus, Foot and mouth disease virus, Goat pox virus, Hantaanvirus, Hendra virus, Hepatitis A virus, Hepatitis B virus, Hepatitis C virus, Hepatitis E virus, Herpes simplex virus, Highly pathogenic avian influenza virus, Human immunodeficiency virus, Human parainfluenza virus, Influenza virus, Japanese encephalitis virus, Kaposi's sarcoma-associated herpesvirus, Lassa virus, Lujo virus, Marburg virus, Marsilia virus, Measles virus, Monkeypox virus, Mumps virus, Nipah virus, Papillomavirus, Papova virus, Peste des petits ruminants, Polio virus, Polyomavirus, Rabies virus, Respiratory syncytial virus, Rhinovirus, Rinderpest virus, Rotavirus, Rubella virus, Sandfly fever Naples virus, Sandfly fever Sicilian virus, SARS coronavirus, Sheep pox virus, Simian immunodeficiency virus, Smallpox virus, St. Louis encephalitis virus, Toscana virus, Varicella-zoster virus, West Nile virus, Western equine encephalitis virus, Yellow fever virus, *Bacillus anthracis, Bordetella pertussis, Brucella* spp., *Campylobacter jujuni, Chlamydia trachomatis, Clostridium botulinum, Coxiella burnettii, Francisella tularensis,* Group B *streptococcus, Legionella pneumophila, Leptospira* spp., *Mycobacterium leprae, Mycobacterium tuberculosis, Mycobacterium ulcerans, Neisseria meningitidis, Salmonella, Shigella* spp., *Trypanosoma cruzi, Vibrio cholerae, Yersinia pestis, Mycoplasma mycoides, Plasmodium malariae, Plasmodium ovale, Plasmodium* ssp., *Plasmodium vivax, Taenia solium, Taenia* spp., and *Trypanosoma brucei*. Said organism may also be a bunyavirus that is the same or different from the bunyavirus from which the (NSm)GnGc proteins are derived. Said foreign gene is preferably derived from an influenza virus and preferably comprises a hemagglutinin protein and/or a neuramidase protein.

In a further preferred method according to the invention, a foreign gene is present on a M, L or S-minigenome. The term "minigenome" refers to an RNA molecule that at least comprises the 5' and 3' regions of a bunyavirus M, L and/or S genome segment that function in replication and transcription of the genomic segment. The 5' and 3' regions of a bunyavirus M, L and/or S genome segment comprise partially complementary untranslated regions (UTRs) flanking the coding region of each segment. The terminal 8 nucleotides of these UTRs are conserved between the three segments, while the remaining sequences of the regions are unique. The UTRs direct replication and transcription of viral RNA and mediate encapsidation of viral RNA into ribonucleoprotein complexes. A minigenome is preferably present in addition to a bunyavirus L genome segment and an S genome segment at least comprising the N-gene. In addition, an M genome segment from which the GnGc coding region has been functionally inactivated is optionally present.

When present, the foreign gene is preferably positioned in an expression cassette that mediates expression of the RNA and/or protein product of the foreign gene. It is further preferred that said expression cassette mediates cell-specific or tissue-specific expression of the RNA and/or protein product of the foreign gene.

The eukaryotic cell in a method of the invention is preferably a cell that can easily be infected and/or transfected using standard methods known to the skilled person, such as, for example, yeast cells and chicken fibroblast cells. Said eukaryotic cell preferably is an insect cell or a mammalian cell. Suitable insect cells comprise, for example, ovarian *Spodoptera frugiperda* cells such as Sf9 and Sf21, *Drosophila* Schneider 2 cells and *Aedes albopictus* C6/36 cells. Suitable mammalian cells comprise, for example, Baby Hamster Kidney cells such as BHK-21, Human Embryonic Kidney cells such as HEK293, VERO cells, MDCK cells, CHO cells, HuH-7, HeLa, SW13 and PER.C6 cells (Fallaux, F. J. et al. 1998. Hum Gene Ther 9: 1909-1917). A preferred cell is BHK-21.

A method according to the invention can be used to generate a recombinant bunyavirus replicon particle from a bunyavirus that is or will be known to a skilled person. A method according to the invention is preferably used to generate a recombinant Crimean-Congo hemorrhagic fever virus replicon particle, a recombinant Nairobi-sheep disease virus replicon particle, a recombinant Dobrava-Belgrade virus replicon particle or, most preferred, a recombinant Rift Valley fever virus replicon particle.

The invention further provides a recombinant bunyavirus replicon particle, comprising a bunyavirus L genome segment, a bunyavirus S genome segment or part of a bunyavirus S genome segment comprising at least the N gene and, optionally, a bunyavirus M genome segment from which the GnGc coding region has been functionally inactivated. Said recombinant bunyavirus replicon particle can be generated using a method according to the invention. Said bunyavirus replicon particle is preferably selected from the genera *Hantavirus, Nairovirus, Orthobunyavirus,* and *Phlebovirus,* which include numerous virus species capable of causing severe disease in both animals and humans. Well known examples are hantaanvirus (HTNV) and Dobrava-Belgrade virus (DOBV) (both of the *Hantavirus* genus), Crimean-Congo hemorrhagic fever virus (CCHFV) and Dugbe virus (both of the *Nairovirus* genus), Bunyamwera virus (Orthobunyavirus), Oropouche virus (Orthobunyavirus), Rift Valley fever virus (RVFV, *Phlebovirus* genus) and further members of the *Phlebovirus* genus: Toscana virus, Sandfly fever Naples virus, Punta Toro virus, Uukuniemi virus, Massilia virus and severe fever with thrombocytopenia syndrome virus. Further preferred bunyaviruses include, but are not limited to, viruses of the Dera Ghazi Khan virus Group, the Hughes virus Group, Nairobi sheep disease virus Group, Qalyub virus Group, Sakhalin virus Group, and the Thiafora virus Group.

It is preferred that one or more of the bunyavirus L genome segment, the S genome segment, and/or, when present, the M genome segment of recombinant bunyavirus replicon particle according the invention, comprises a foreign gene. Said foreign gene is preferably derived from an organism that is a transmitter of an infectious disease. As an alternative, a preferred recombinant bunyavirus replicon particle according to the invention comprises a foreign gene that is present on a M, L or S-minigenome.

A preferred recombinant bunyavirus replicon particle according to the invention is derived from a bunyavirus selected from Crimean-Congo hemorrhagic fever virus, Nairobi-sheep disease virus, Dobrava-Belgrade virus and Rift Valley fever virus. A most preferred bunyavirus is Rift Valley fever virus.

The invention additionally provides a method for producing a recombinant bunyavirus replicon particle, the method comprising A) providing a eukaryotic cell with growth medium, B) providing the eukaryotic cell with sufficient bunyavirus (NSm)GnGc, and C) infecting the eukaryotic cell with a recombinant bunyavirus replicon particle according to the invention, so as to produce a bunyavirus replicon particle. Said eukaryotic cell is preferably a cell that is persistently infected with a viral vector that transduces the bunyavirus (NSm)GnGc proteins, or a stable cell in which an expression construct that expresses the Bunyavirus (NSm)GnGc proteins is integrated into the genome. Said expression construct preferably comprises means for conditional expression of the bunyavirus (NSm)GnGc proteins.

A recombinant bunyavirus replicon particle according to the invention is safe and can be used outside a biosafety containment. Said recombinant bunyavirus replicon particle can be used, for example, for screening and development of anti-viral agents, for example for development of a high throughput system for screening of suitable compound libraries. Said recombinant bunyavirus replicon particle can also be used in tests or assays including virus neutralization assays or virus neutralization tests (VNT) and ELISAs, including whole-virus ELISAs, and hemagglutination assays.

For example, a classical VNT requires handling of live bunyavirus and must therefore be performed in appropriate biosafety containment facilities. Another drawback of the classical VNT is that the assay requires 5-7 days for completion. An advantage of the use of bunyavirus replicon particles, such as RVFV replicon particles (RRPs), in stead of live bunyavirus, is that the VNT can be performed outside biocontainment facilities. A further advantage is that the VNT requires only 24-48 hrs for completion.

The invention further provides a recombinant bunyavirus replicon particle according the invention for use as a medicament. A recombinant bunyavirus replicon particle according the invention is preferably for use as a medicament for amelioration of a bunyavirus infection in an animal, including in a human.

A pharmaceutical medicament comprising a recombinant bunyavirus replicon particle according the invention may additionally comprise a pharmaceutical acceptable adjuvant, diluent or carrier. A medicament according to the invention is preferably combined with other therapeutic options, including but not limited to a combination treatment with ribavirin, and/or derivatives of ribavirin such as taribavirin.

The invention further provides a vaccine comprising a recombinant bunyavirus replicon particle according to the invention. Said vaccine preferably comprises an adjuvant. Adjuvant substances are used to stimulate immunogenicity. Examples of commonly used immunological adjuvants are aluminum salts, immunostimulating complexes (ISCOMS), non-ionic block polymers or copolymers, cytokines (like IL-1, IL-2, IL-7, etc.), saponins, monophosphoryl lipid A (MPLA), muramyl dipeptides, vitamin E, polyacrylate resins, and oil emulsions. Preferably, the adjuvant is a sulfolipopolysaccharide, such as the SLP/S/W adjuvant described in Hilgers et al. Vaccine 1994 12:653-660. A further preferred adjuvant is provided by a triterpene, such as squalene, and derivatives and modifications thereof.

Bunyavirus replicon particles, for example RRPs, according to the invention are non-spreading particles that are capable of autonomous genome replication. Bunyavirus replicon particles according to the invention contain both the S and L genome segment, or functional parts thereof, but lack a bunyavirus M genome segment or comprise a bunyavirus M genome segment on which the GnGc coding region has been functionally inactivated. The presence of the L and S genome segments, which encode the N protein and the L protein, enables the resulting particles of autonomous genome replication. The absence or inactivity of a GnGc coding region prevents assembly and spread of virus particles. The replicon particles can be produced in cells that supply GnGc in trans to titers up to 10E7 infectious particles/ml. Replication of the bunyavirus genome and/or expression of the N and L protein in a host might result in an improved immune response, when compared with an immune response induced by vaccination with bunyavirus-like particles or viral subunits. For example, a single intramuscular vaccination with RRPs protects mice against a lethal challenge dose with RVFV strain 35/74.

Said vaccine may be administered to an animal, including a human, by any method known in the art. Said vaccine is preferably administered by needle-free, non-invasive methods such as oral, intranasal and/or intratracheal administration, for example through inhalation or the use of nose-sprays. Said vaccine is more preferably parenterally administered, for example, intramuscularly, subcutaneously, intraperitoneally, intradermally or the like, preferably intramuscularly.

A vaccine according to the invention is administered in effective amounts according to a schedule which may be determined by the time of anticipated potential exposure to a bunyavirus. In this way, the treated animal, including a human, may have time to build immunity prior to the natural exposure. A typical treatment schedule or dosing regimen comprises parenteral administration, preferably intramuscular injection, of one dosage unit, at least about 2-8 weeks prior to potential exposure. If required, a second dosage unit is administered at about 2-4 weeks prior to potential exposure. The second dosage may be administered by the same method, or by a method differing from the first dosage unit.

The administration of a vaccine according to the invention preferably protects the animal, including a human, against a subsequent infection by the bunyavirus. In a preferred embodiment, a vaccine according to the invention comprises a recombinant Rift Valley fever virus replicon particle that protects the animal, including a human, against a subsequent infection by Rift Valley fever virus.

An important advantage of a vaccine according to the invention is that the virus is not capable of autonomous spread in the vaccinated animal. The inability to spread from the initial site of inoculation, greatly adds to the safety of this vaccine, both for the inoculated animal, the administrator of the vaccine as well as the environment. The inability to cause viremia in the vaccinated animal also prevents any concerns about possible transmission of this vaccine by insect vectors (see Moutailler et al. 2010. Vector Borne Zoonotic Dis 10:681-688). A vaccine comprising a non-spreading Bunyavirus replicon particle according to the invention which lacks the NSs gene (such as those reported in Example 1 and in Kortekaas et al. 2011. J. Virol. Accepted for publication) are considered of optimal safety, due to the lack of this major virulence factor.

A further important advantage of a vaccine according to the invention compared to inactivated vaccines or subunit vaccines is the fact that the present vaccine does not depend on an adjuvant to induce immunity. In addition, a vaccine according to the invention can be produced with superior cost-effectiveness and will be superior with respect to duration of immunity. Although the virus is non-spreading, due to the inability to express GnGc protein, the viral genome is replicated in infected cells and N- and L-proteins are expressed, resulting in a strong, long-lasting induction of an immune response in a recipient.

It is important to note that there are concerns about the safety of the MP-12 (Morrill et al. 1991. Vaccine 9:35-41, Morrill et al. 1997. Am J Vet Res 58:1104-1109, Morrill et al. 1997. 58:1110-1114, Morrill et al. 2011. 204:229-236, Morrill et al. 2011. J Infect Dis 204:617-625), Clone 13 (Muller et al., 1995. Am J Trop Med Hyg. 53:405-411, Vialat et al. 2000. J Virol 74:1538-1543, Dungu et al. 2010. Vaccine 28:4581-4587) and R566, a reassortant virus that contains the S segment of the Clone 13 virus and the L and M segments of the MP-12 virus (Flick et al. 2009. Antiviral Res 84:101-118) vaccine viruses. The MP-12 vaccine virus was shown to contain potential attenuating mutations on each of the three genome segments (Vialat et al. 1997. Virus Res 52:43-50). The nucleotide changes responsible for attenuation of this virus are, however, not mapped. It is therefore possible that only a single nucleotide change could result in reversion to virulence. Although several studies have demonstrated the safety of the MP-12 vaccine (see papers of Morrill et al. noted above), a further study demonstrated that the MP-12 vaccine is not safe when administered to gestating ewes during the first trimester of gestation (Hunter et al., 2002 Onderstepoort J Vet Res 69; 95-98). Since the R566 vaccine contains the L and M segments of the MP-12 virus, similar concerns may be raised about the safety of this vaccine.

Death of Clone 13-vaccinated mice due to neurological disorders and paralysis was reported in one of the first articles on the Clone 13 virus (Vialat et al. 2000. J Virol 74:1538-1543). This finding suggested that the safety of the Clone 13 virus should also be further studied in clinical trials involving large numbers of animals.

None of the animals that were vaccinated with a Bunyavirus replicon particle according to the invention suffered from complications associated with the vaccination.

The invention further provides a method of stimulating an immune response against bunyavirus in an animal, including a human, the method comprising providing the animal with a recombinant bunyavirus replicon particle according to the invention. In a preferred method, a recombinant Rift Valley fever virus replicon particle according to the invention is provided to an animal, including a human, to stimulate an immune response against Rift Valley fever virus.

The invention further provides the use of a recombinant bunyavirus replicon particle according to the invention, for stimulating an immune response against a protein encoded by the foreign gene. In one embodiment, said foreign gene preferably encodes an antigenic protein that is expressed by an Orthomyxovirus, preferably influenza A virus, or an immunologically-active part or derivative of a protein that is expressed by an Orthomyxovirus. Methods for determining whether a protein, or a part or derivative of a protein, is immunologically active are known to the person skilled in the art, including algorithms that predict the immunogenicity of a protein such as an algorithm of Parker and an algorithm of Rammensee, as disclosed in Provenzano et al. 2004. Blood 104: Abstract 2862) and including the injection of the purified protein, or a part or derivative of the protein in a suitable animal and determining whether the protein, or a part or derivative of a protein is capable of stimulating antibodies against the protein, or a part or derivative of a protein.

The term immunologically-active part indicates a part of a protein that is able to induce a cellular and/or humoral immune response against the protein in an animal, including a human. The term immunologically-active derivative indicates a protein or part of a protein that is modified, for example by addition, deletion or alteration of one or more amino acids and which is able to induce a cellular and/or humoral immune response against the protein in an animal, including a human. It is preferred that an immunologically-active derivative has a sequence identity of more than 70% compared to the parental protein, for example the protein that is expressed by the Orthomyxovirus, preferably an influenza A virus. The sequence identity is more preferred more than 80%, more preferred more than 90%, more preferred more than 95%, more preferred more than 99%, most preferred 100%, as based on the amino acid sequence of the protein or protein parts. Said immunologically-active derivative is, for example, a protein that comprises a signal peptide for secretion out of the cell in which it is produced, a protein that comprises a sequence that provides a trans-membrane such as a type I, II or III targeting domain, or a protein in which a protease cleavage site has been altered to enhance the half-life of the protein.

FIGURE LEGENDS

FIG. 1.
Expression of the N protein from the RVFV S genome segment. BSR-T7/5 cells (A) or FP-T7-infected BHK-21 cells (B) were transfected with plasmid pUC57-S, encoding the RVFV S genome segment in the antigenomic-sense orientation. Expression of the RVFV N protein was detected using a N protein-specific mAb and HRP-conjugated anti-mouse IgG antibodies.

FIG. 2.
Production of Rift Valley fever virus replicon particles (RRPs) containing three genome segments. BHK cells were infected with FP-T7 and subsequently transfected with a plasmid encoding the M-eGFP minigenome (M-eGFP), or in combination with plasmids encoding the RVFV L and S genome segments (M-eGFP/L/S), or in combination with the aforementioned plasmids and pCAGGS-NSmGnGc (M-eGFP/L/S+NSmGnGc). The number of eGFP-positive producer cells, recipient cells or recipient cells previously transfected with helperplasmids (+HP) pCIneo-RVFV-L and pCAGGS-N were determined by flow cytometry.

Figure 3:
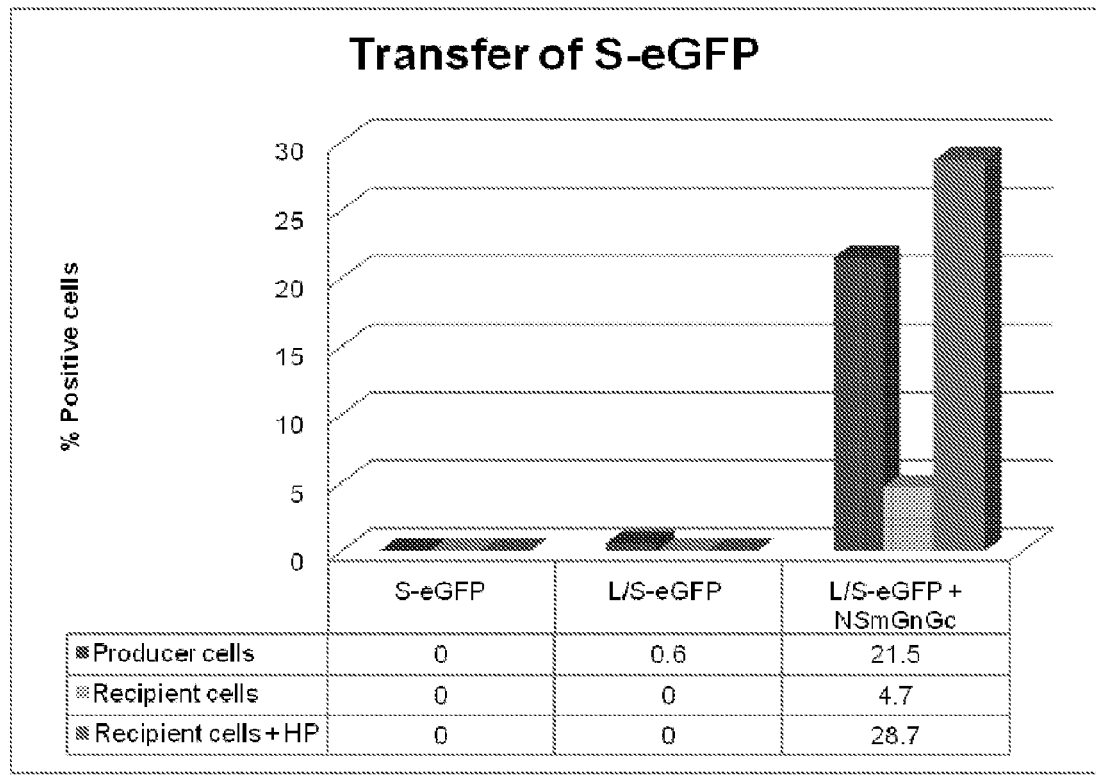

FIG. 3.
Production of RRPs containing two genome segments. BHK cells were infected with FP-T7 and subsequently transfected with a plasmid encoding the S-eGFP minigenome (S-eGFP), or in combination with plasmids encoding the RVFV L genome segments (S-eGFP/L), or in combination with the aforementioned plasmids and pCAGGS-NSmGnGc (S-eGFP/L+NSmGnGc). The number of eGFP-positive producer cells, recipient cells or recipient cells previously transfected with helperplasmids (+HP) pCIneo-RVFV-L and pCAGGS-N were determined by flow cytometry.

Figure 4:
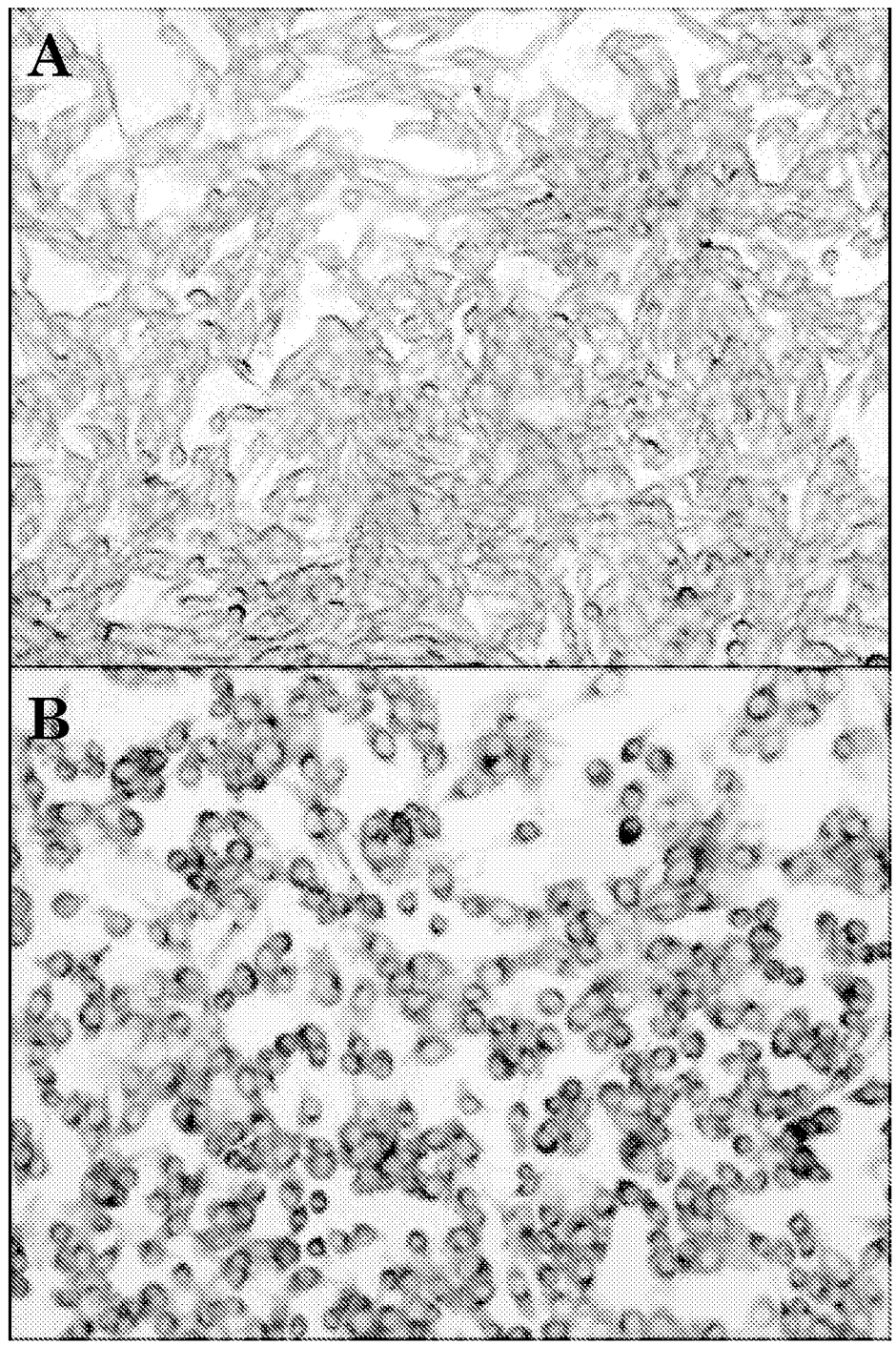
Figure 4:
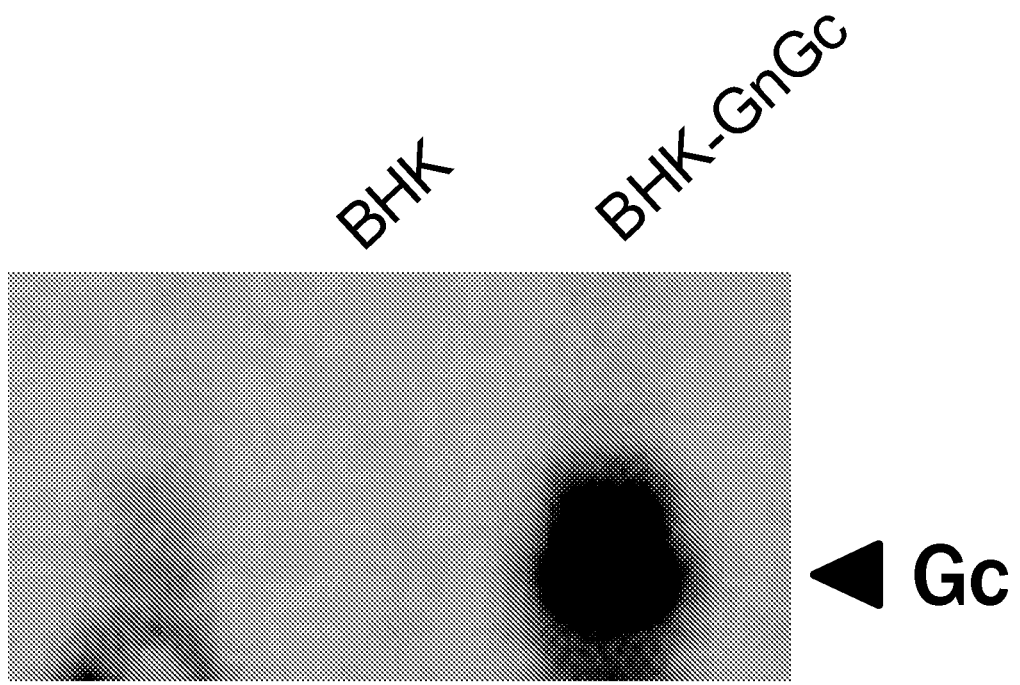

FIG. 4.
Expression of GnGc in BHK-GnGc cells. Detection of GnGc expression in BHK-21 cells (negative control, A) and BHK-GnGc cells (B) by IPMA using polyclonal antibodies directed against the Gn and Gc proteins and detection of Gc in cell lysates on a Western blot (C) using a peptide antiserum.

FIG. 5.

Expression of eGFP in BHK-GnGc cells persistently infected with NDV-GnGc maintaining the RVFV L genome segment and S-eGFP minigenome at cell passage 18.

FIG. 6.

RRP production by BHK-GnGc cells after introduction of pCAGGS-GnGc or pCAGGS-NSmGnGc. At 16 h after transfection, the culture medium was replaced by fresh medium. RRP titers were determined on BHK-21 cells using the Spearman-Kärber method (Kärber 1931. Arch. Exp. Path. Pharmak 162, 480-483; Spearman 1908 Br. J. Psychol 2, 227-242).

FIG. 7.

(A) Partial sequence pUC57-L (SEQ ID NO:20): Plasmid encodes the RVFV strain 35/75 L genome segment in antigenomic-sense orientation.

cDNA of the RVFV strain 35/74 L genome segment, flanked by a T7 promoter and cDNA encoding a HDV ribozyme was synthesized by the GenScript Corporation and cloned in the pUC57 vector using KpnI/HindIII. The T7 promoter, HDV ribozyme sequence and T7 terminator sequences, respectively, are underlined. The UTRs are indicated in italics, the open reading frame encoding the L protein is indicated in bold.

(B) Partial sequence of plasmid pUC57-M (SEQ ID NO:21): Plasmid encodes the RVFV strain 35/74M genome segment in antigenomic-sense orientation.

cDNA encoding the antigenomic-sense RNA of the RVFV strain 35/74 M genome segment, flanked by a T7 promoter and cDNA encoding a HDV ribozyme was synthesized by the GenScript Corporation and cloned in the pUC57 vector using EcoRI/SalI. The T7 promoter, HDV ribozyme sequence and T7 terminator sequences, respectively, are underlined. The UTRs are indicated in italics, the open reading frame encoding the NSmGnGc proteins is indicated in bold.

(C) Partial sequence of plasmid pUC57-S(−) (SEQ ID NO:22): Plasmid encodes the RVFV strain 35/74 S genome segment in genomic-sense orientation.

cDNA encoding the genomic-sense RNA of the RVFV strain 35/74 S genome segment, flanked by a T7 promoter and cDNA encoding a HDV ribozyme was synthesized by the GenScript Corporation and cloned in the pUC57 vector using BamHI/XbaI. The T7 promoter, HDV ribozyme sequence and T7 terminator sequences, respectively, are underlined. The UTRs and intergenic region are indicated in italics, the open reading frames encoding the N and NSs proteins are indicated in bold.

(D) Partial sequence of plasmid pUC57-SΔNSs (SEQ ID NO:23): Plasmid encodes the RVFV strain 35/74 S genome segment in antigenomic-sense orientation with a major deletion in NSs.

The synthetic DNA was cloned between XbaI and ApaI of pUC57. The T7 promoter, HDV ribozyme sequence and T7 terminator sequences, respectively, are underlined. The UTRs and intergenic region are indicated in italics, the open reading frame encoding the N and the open reading frame encoding part of the NSs protein are indicated in bold.

(E) Partial sequence of plasmid pUC57-S (SEQ ID NO:24): Plasmid encodes the RVFV strain 35/74 M genome segment in antigenomic-sense orientation.

To construct cDNA encoding the complete S genome segment in antigenomic-sense orientation, the sequence between NcoI, EcoRV was isolated from the pUC57-S(−) construct and used to replace the sequence between NcoI and EcoRV of plasmid pUC57-SΔNSs, yielding pUC57-S. The T7 promoter and HDV ribozyme and T7 terminator sequences, respectively are underline. The UTRs and intergenic region are indicated in italics, the open reading frames encoding the N and NSs proteins are indicated in bold.

(F) Partial sequence of plasmid pUC57-S-eGFP (SEQ ID NO:25): Plasmid encodes the RVFV strain 35/74 NI genome segment in antigenomic-sense orientation, where the NSs gene is replaced for the gene encoding enhanced green-fluorescent protein (eGFP).

The T7 promoter and HDV ribozyme and T7 terminator sequences, respectively are underlined. The UTRs and intergenic region are indicated in italics, the open reading frames encoding the N and eGFP proteins are indicated in bold. The sequence was cloned between KpnI and SalI of pUC57. A silent C→T mutation is underlined.

(G) Partial sequence of plasmid pUC57-Mv (SEQ ID NO:26): Plasmid encodes the RVFV strain 35/74M genome segment in genomic-sense orientation, where the complete NSmGnGc ORF is deleted and NcoI and XbaI sites are introduced.

The T7 promoter and HDV ribozyme and T7 terminator sequences, respectively are underlined. The UTRs are indicated in italics, the sequence between the UTRs is indicated in bold. Cloned between EcoRI and PstI pUC57.

(H) Partial sequence of plasmid pUC57-Mv-eGFP (SEQ ID NO:27): Plasmid encodes the RVFV strain 35/74 M genome segment in genomic-sense orientation, where the complete NSmGnGc ORF is deleted and eGFP is introduced between the NcoI and XbaI sites. The T7 promoter and HDV ribozyme sequences are underlined.

(I) Partial sequence of plasmid pUC57-GnGc (SEQ ID NO:28): Plasmid encodes a codon-optimized version of the open reading frame of the RVFV strain 35/74 M genome segment starting at the fourth methionine codon. The gene was synthesized and cloned between EcoRI and HindIII. This gene was used to construct pCIneo-GnGc and pCAGGS-GcGc Using EcoRI and NotI (underlined). The GnGc open reading frame is indicated in bold.

(J) Plasmids pCIneo-NSmGnGc and pCAGGS-NSmGnGc encode the open reading frame of the RVFV strain 35/74 M genome segment starting at the first methionine codon (SEQ ID NO:29). The gene was amplified from 35/74 cDNA and cloned in pCIneo and pCAGGS using EcoRI and NotI (underlined). The NSmGnGc open reading frame is indicated in bold.

(K) Plasmid pUC57-N encodes a codon-optimized version of the N open reading frame of the RVFV strain 35/74 (SEQ ID NO:30). The gene was introduced into pCAGGS and pCIneo using EcoRI and NotI (underlined). The open reading frame of the N protein is indicated in bold.

(L) Plasmid pCIneo-L contains the open reading frame of the L gene of RVFV strain 35/75 (SEQ ID NO:31). The gene was introduced into using XhoI and NotI (underlined). The transition mutation (T5912C), resulting in the substitution of isoleucin-1971 for threonine is also underlined. The open reading frame of the L protein is indicated in bold.

FIG. 8.

RRPs are incapable of autonomous spread. BHK cells were infected with RRPs at an m.o.i. of 1. After two days, eGFP expression was observed in infected cells (left panel). Fresh BHK cells were incubated with the collected supernatant and monitored for eGFP expression after three days (right panel).

FIG. 9.

RRP production kinetics. BHK-Rep cells were grown in GMEM supplemented with 5% serum and were either left untreated (−GP) or transfected with pCAGGS-NSmGnGc (+GP). RRP titers were determined at different time points on BHK cells using eGFP expression as the readout parameter. Titers were determined using the Spearman-Kärber method.

FIG. 10.

Western blot analysis of RRP proteins. Culture medium of BHK-Rep cells (−GP) or of BHK-Rep cells transfected with pCAGGS-NSmGnGc (+GP) was ultracentrifuged at 100 000×g for 2 h. The proteins present in the pellets were separated in 4-12% NuPAGE Bis-Tris gels and subsequently transferred to nitrocellulose blots. Specific proteins were detected by an anti-Gn (α-Gn) or anti-Gc (α-Gc) peptide antiserum or a mAb specific for the N protein (αN). The positions of the NSm, Gn, Gc and N protein are indicated by arrows. Molecular weight standard proteins are indicated to the right in kilodaltons.

FIG. 11.

RRP infection of mammalian and insect cells. Cells were infected with RRPs and the number of positive cells was determined by flow-cytometry at 42 (BHK and HEK293T) or 72 hours post infection (S2 and C6/36). (A) Representative result from flow cytometry of RRP-infected mammalian and insect cells. Counts of non-infected control cells and infected cells are depicted in grey and green respectively. (B) Histograms showing averaged results of three independent measurements with S.D.

FIG. 12.

Vaccine efficacy of RRPs. Mice were either non-vaccinated (n=9; Mock) or vaccinated (n=10) either once (1×) or twice (2×) via the intramuscular route (IM) or subcutaneous route (SC) with 106 TCID50 of RRPs. Mice were challenged with a known lethal dose of RVFV strain 35/74 via the intraperitoneal route. The mortality rates were determined until 21 days post challenge (d.p.c.).

FIG. 13.

Injection site reactions observed at different time points after vaccination. Score 0: No aberrations noted; 1: Swelling observed; 2: Round swelling of maximal 5 cm in diameter; 3: Major swelling/abscess chance of rupture. PM, post mortem. Results are depicted as averages (n=6) with SD.

FIG. 14.

Rectal temperatures of vaccinated and unvaccinated (Mock) lambs before and after challenge with RVFV. Rectal body temperatures (° C.) were determined daily. Fever was defined as a body temperature above 41° C. (interrupted line). Results are depicted as averages (n=6) with SD.

FIG. 15.

Detection of viral RNA in plasma samples of vaccinated and unvaccinated lambs obtained at different time points after challenge infection with RVFV. The number of positive samples differs at each time point. Results are depicted as averages (n=6) with SD.

FIG. 16.

Body weight of lambs vaccinated once with one of the indicated vaccines. Results are depicted as averages (n=6) with SD.

FIG. 17.

Biochemical analysis of serum samples. ALT, ALP, TP, Creatinine and BUN concentrations are depicted as averages (n=6) with SD. The upper and lower reference values are indicated by dashed lines.

FIG. 18.

Schematic representation of the method used to create replicon cell lines producing the sHA$_3$ and sNA$_4$ proteins. GOI, gene of interest (in this work either the eGFP, sHA$_3$ or sNA$_4$, gene).

FIG. 19.

Flow cytometry demonstrating the percentage of replicon cell lines that produce the N protein at cell passage 8. N protein expression is dependent on the presence of the S and L genome segment, of which the former contains the foreign gene of interest (GOI). Cells expressing L and S-eGFP genome segments (A); cells expressing L and the S-CD5-HA-GCN4-ST (i.e. S-$_s$HA$_3$) segment (B); cells expressing L and the S-CD5-OS-GCN4-NA segment (i.e. 5-$_s$NA$_4$) (C); control cells expressing GnGc are depicted in (D), (E) and (F).

FIG. 20.

Purified sHA$_3$ and sNA$_4$ were analyzed on Silver-stained polyacrylamide gels (A) and Western blots using Strep-Tacting-HRP for detection (B). The negative control sample (eGFP) was provided by following the purification procedure using medium collected from replicon cells expressing eGFP. The positions of molecular weight standard proteins are indicated to the left in kDa.

EXAMPLES

Example 1

Materials and Methods

Cells and Growth Conditions.

BSR-T7/5 were kindly provided by Prof. Dr. K. Conzelmann (Max von Pettenkofer-Institut, Munchen, Germany). BHK-GnGc are BHK-21 cells that contain a genome-integrated plasmid pCIneo-GnGc described hereinbelow. BSR-T7/5 and BHK-GnGc cells were grown in Glasgow Minimum Essential Medium (GMEM; Invitrogen, Carlsbad, Calif., USA) supplemented with 4% tryptose phosphate broth (Invitrogen), 1% non-essential amino acids (Invitrogen), 10% fetal bovine serum (FBS; Pam Biotech, Aidenbach, Germany) and penicillin/streptomycin (Invitrogen) at a concentration of 100 U/ml and 100 µg/ml, respectively. For maintenance of stable cell lines, geneticin (G-418; Invitrogen) was used at a concentration of 1 mg/ml. Cells were grown at 37° C. and 5% CO2.

Plasmids and Viruses.

Plasmids pCIneo-GnGc and pCAGGS-GnGc contain the open reading frame (ORF) of the M segment of RVFV strain 35/74, starting at the fourth methionine codon (FIG. 7I). Plasmid pCAGGS-N contains the ORF encoding the N gene (FIG. 7K). The N and GnGc-encoding sequences were codon-optimized for optimal expression in mammalian and insect cells and synthesized by the GenScript Corporation (Piscataway, N.J., USA). Plasmid pCAGGS-NSmGnGc contains the authentic ORF of the M segment starting at the first methionine codon (FIG. 7J). pCIneo-RVFV-L encodes the authentic ORF encoding the viral polymerase of RVFV strain 35/74 (FIG. 7L). This gene contains a transition mutation (T5912C), resulting in the substitution of isoleucin-1971 for threonine. The effect of this mutation was not studied. Expression of RVFV genes from pCIneo plasmids is controlled by a cytomegalovirus (CMV) immediate-early enhancer/promoter, whereas the expression of genes from pGAGGS plasmids is controlled by a CMV immediate enhancer/β-actin (CAG) promoter (Niwa et al. 1991. Gene 108: 193-199). RVFV strain 35/74 was isolated at the Agricultural Research Council-Onderstepoort Veterinary Institute (ARC-OVI) from the liver of a sheep that died during a RVFV outbreak in the Free State province of South Africa in 1974 (Barnard 1979. J S Afr Vet Assoc 50: 155). The virus was passaged four times in suckling mice by intra-cerebral injection and three times on BHK-21 cells. Amplification of the genome segments was performed by one-step RT-PCR with SBS Genetech AMV-RT, TaKaRa Ex Taq HS and the primers described by Bird et al. (Bird et al. 2007. J Virol 81: 2805-2816). PCR products were purified with the Qiagen Gel extraction kit after separation on agarose gel and mixed in appropriate equal amounts before GS FLX sequencing at Inqaba Biotec (Pretoria, South Africa). Sequencing and sequence assembly was performed essentially as described for dsRNA virus genomes (Potgieter et al. 2009. J Gen Virol 90: 1423-1432). Consensus sequences corresponding to each genome segment were synthesized and cloned in pUC57, a standard cloning vector of GenScript Corporation (Piscataway, N.J., USA). pUC57-L (FIG. 7A), pUC57-M (FIG. 7B) and pUC57-S (FIG. 7E) encode the RVFV L, M and S genome segment in antigenomic (i.e. positive) sense orientation, respectively. These transcription plasmids each contain a complete copy of the viral RNA segments and are flanked by a T7 promoter and a HDV ribozyme sequence. In pUC57-S-eGFP(−) (FIG. 7F), the NSs gene is replaced by the gene encoding enhanced green fluorescent protein (eGFP). Of note, transcription of this plasmid results in a S-eGFP minigenome in which the eGFP gene is in the genomic (i.e. negative-sense) orientation. In plasmid pUC57-Mv-eGFP(−) (FIG. 7H), the complete ORF of the M segment is replaced by the eGFP gene. The M-eGFP minigenome produced from this plasmid is in the genomic-sense orientation as well.

A recombinant Newcastle disease virus (NDV) that produces the RVFV structural glycoproteins Gn and Gc (i.e. NDFL-GnGc), from hereon referred to as NDV-GnGc, was previously described (Kortekaas et al. 2010. Vaccine 28: 4394-4401).

A recombinant fowlpox virus that produces T7 polymerase, named fpEFLT7pol (Das et al. 2000. J Virol Meth 89: 119-127), from hereon referred to as FP-T7, was kindly provided by the Institute for Animal Health (IAH, Compton, UK). Virus titers were determined as 50% tissue culture infective dose (TCID50) on BHK-21 cells using the Spearman-Kärber method (Kärber 1931. Arch. Exp. Path. Pharmak 162, 480-483; Spearman 1908 Br. J. Psychol 2, 227-242).

Rescue of Recombinant RVFV Strain 35/74.

BSR-T7/5 cells were seeded in 6-well plates and were co-transfected with 1 µg of plasmids pUC57-L, pUC57-M and pUC57-S using jetPEI transfection reagent according to the instructions of the manufacturers (Polyplus-transfection SA, Illkirch, France). After 6 days of incubation, medium was collected. For the detection of infectious virus, BHK-21 cells were incubated with the collected supernatant. When clear cytopathic effect was observed, the cells were fixed in 4% paraformaldehyde/PBS for 40 min. Plates were subsequently submerged completely in 80% ethanol/4% acetic acid to inactivate the virus and washed with PBS. Immunoperoxidase monolayer assays (IPMAs) were performed as described hereinbelow.

Alternatively, BHK-21 cells were infected with FP-T7. Approximately 10E6 cells in each well of a six-well plate were inoculated with 1.5 ml of culture medium containing 10E5 TCID50 of FP-T7 (multiplicity of infection [m.o.i.] of 0.1). After incubation with FP-T7 for 1 h and recovery for another hour, the cells were treated in a similar way as described for BSR-T7/5 cells.

Rescue of RVFV BRPs (RRPs).

BHK-21 or BHK-GnGc cells were seeded in 6-well plates and incubated with FP-T7 for 1 h at 37° C. Medium was refreshed and cells were allowed to recover for 1 h. For the production of RRPs containing three genome segments, the cells were subsequently transfected with 600 ng of plasmids pUC57-L, pUC57-S, pUC57-Mv-eGFP(−) and pCAGGS-NSmGnGc. For the production of RRPs containing two genome segments, cells were transfected with pUC57-L, pUC57-S-eGFP(−) and pCAGGS-NSmGnGc. The medium was refreshed the next day. Alternatively, when NDV was used to provide Gn and Gc, NDV-GnGc infection was performed together with FP-T7. NDV-GnGc was used at an m.o.i. of 0.05. Supernatants were harvested after 72 h, precleared at 5 000 rpm for 5 min at RT and stored at 4° C. until further use.

NuPAGE and Western Blotting

NuPAGE and Western blotting was performed as described (Kortekaas et al. 2010. Vaccine 28: 2271-2276). Briefly, proteins were diluted in 3× Laemmli sample buffer (0.5 M Tris pH 6.8, 6% (w/w) SDS, 26% (v/v) glycerol, 15% (v/v) 2-mercaptoethanol and 0.002% (w/w) bromophenol blue) and heated at 95° C. for 5 minutes, before loading onto 4-12% NuPAGE Bis-Tris gels. Proteins were subsequently transferred to nitrocellulose blots. To visualize Gc, rabbit polyclonal antibodies were used that were previously raised against a Gc-derived peptide (residues 975-VFERGSLPQTRNDKTFAASK-994), respectively (De Boer et al. 2010. Vaccine 28:2330-2339). Goat anti-rabbit IgG antibodies conjugated to horseradish peroxidase (HRP) (Dako, Heverlee, Belgium) were used as the secondary antibodies. Peroxidase activity was detected using the Amersham ECL™ Western blotting detection reagents (GE Healthcare, Diegem, Belgium). For the detection of the N protein, monoclonal antibody F1D11 (kindly provided by Dr. Alejandro Brun, CISA-INIA, Madrid, Spain) was used as the primary antibody and rabbit anti-mouse IgG (DAKO) as the secondary antibody.

Immunoperoxidase Monolayer Assays (IPMA).

IPMAs were performed as described previously (deBoer et al. 2010. Vaccine 28: 2330-2339). As the primary antibody, either a polyclonal antiserum was used that was previously obtained from a sheep that was vaccinated with NDFL-GnGc (Kortekaas et al. 2010. Vaccine 28: 4394-4401). For detection of the RVFV N protein, mAb F1D11 was used, which was previously kindly provided by Dr. Alejandro Brun (CISA-INIA, Spain). As the secondary antibody HRP-conjugated rabbit anti-mouse IgG (Dako, Heverlee, Belgium) was used.

Flow Cytometry.

For flow cytometry, cells of a six-well plate were washed with 3 ml PBS and then trypsinized with 0.3 ml 0.5% trypsine-EDTA (Invitrogen). After incubation for 2-3 min at 37° C. and resuspension, the cells were diluted in 1 ml culture medium. Cells were pelleted by centrifugation, resuspended in 0.5 ml PBS and pelleted again. Cells were fixed by adding 0.1 ml 4% PFA in PBS for 15-30 min and subsequently diluted in 0.5 ml PBS. Each sample contained all the cells from one well. The samples were stored at 4° C. until analysis. All measurements were performed at the day of harvesting the cells. Flow cytometry was performed using a CyAn ADP flow cytometer (Beckman, Woerden, The Netherlands), equipped with a 488 nm wavelength laser. Data analysis was performed with the Summit v4.3 software.

Results

Rescue of recombinant RVFV strain 35/74 from cDNA using BSR-T7/5 cells. Recombinant RVFV strain 35/74 (rec35/74) was rescued using three plasmids encoding the three viral RNA segments L, M and S in antigenomic-sense orientation. Transfection of the three plasmids into BSR-T7/5 cells resulted in cytopathic effect after 3-4 days. BHK-21 cells were inoculated with the collected supernatant. A titer of 10E9 TCID50/ml was obtained after two passages of the virus. No silent mutations were introduced in the genome of recombinant RVFV strain 35/74 to confirm rescue and exclude contamination with non-recombinant wildtype virus, since no wildtype virus was ever present in our laboratory before rescue of rec35/74.

Production of VLPs containing a reporter minigenome using transient expression of NSmGnGc from plasmid.

As a first step towards the establishment of an Rift Valley fever virus replicon particle (RRP) production system, a minireplicon system was developed. A plasmid was designed in which the gene encoding eGFP is placed between M segment untranslated regions (UTRs). This plasmid was named pUC57-Mv-eGFP(−) and encodes the M-eGFP minigenome in genomic-sense orientation. Like the full-length constructs, the cDNA encoding this minigenome is flanked by a T7 polymerase promoter and cDNA encoding a HDV ribozyme sequence. Transfection of pUC57-Mv-eGFP(−) together with plasmids pUC57-L and pUC57-S resulted in eGFP expression in only a few cells (data not shown). In an attempt to improve reporter minigenome expression, the two helper plasmids pCIneo-RVFV-L and pCAGGS-N were added to the transfection mixture. This resulted in a slight increase in the number of positive cells (data not shown). Despite the very low number of eGFP-positive cells, an attempt was made to package the genome segments into VLPs by co-transfecting the cells with pCAGGS-NSmGnGc. If indeed VLPs were produced, we reasoned that these VLPs could contain either one, two or three genome segments. To be able to detect also VLPs that contain only the reporter minigenome, the supernatant was not only added to untreated BHK-21 cells, but also to BHK-21 cells that were previously transfected with helper plasmids pCIneo-RVFV-L and pCAGGS-N. Very few BHK-21 cells that were inoculated with the collected supernatant were shown to express eGFP after 18-24 hrs of incubation and expression was only observed in cells that were previously transfected with helper plasmids (data not shown). Thus, although VLPs were produced, none of these VLPs apparently contained all three genome segments.

Production of VLPs containing a reporter minigenome using NDV to provide Gn and Gc.

Although we were previously able to produce large amounts of VLPs by expressing GnGc in insect cells (de Boer et al. 2010. Vaccine 28: 2330-2339), production of GnGc from pol-II promoters in mammalian cells was extremely poor in previous experiments, yielding no detectable VLPs in the culture supernatant (unpublished results). We also previously reported the production of an NDV recombinant (i.e. NDFL-GnGc, from hereon referred to as NDV-GnGc) that produces the GnGc glycoproteins. Interestingly, infection of BHK-21 cells with this recombinant virus did result in the production of detectable amounts of Gn and Gc in the supernatant (Kortekaas et al. 2010. Vaccine 28: 4394-4401). In the present work, we wondered if NDV-GnGc could be used to provide the Gn and Gc proteins for the packaging of RVFV genome segments. Cells were first transfected with pUC57-L, pUC57-S and pUC57-Mv-eGFP(−) and infected with NDV-GnGc, 24 hrs later. Expression of eGFP was observed in a small percentage of producer cells and in very few recipient cells (data not shown). Expression of eGFP in recipient cells was again dependent on a previous transfection with the helper plasmids pCIneo-RVFV-L and pCAGGS-N. These experiments demonstrated that we were able to package a reporter minigenome into VLPs using NDV-GnGc as a source of the glycoproteins, but that particles capable of autonomous replication were not obtained.

Improved rescue of RVFV from cDNA using a recombinant fowlpox virus as a source of T7 polymerase and successful production of RRPs.

Virus recovery from BSR-T7/5 cells was not reproducible. As an alternative for BSR-T7/5 cells, we decided to use a recombinant fowlpox virus that expresses T7 polymerase (i.e. FP-T7) (Das et al. 2000. J Virol Methods 89: 119-127). In experiments where the rescue efficiency of RVFV using BSR-T7/5 cells and FP-T7-infected BHK-21 cells were compared, use of FP-T7 resulted in RVFV rescue in 5/5 attempts, whereas rescue using BSR-T7/5 cells was unsuccessful. We anticipated that a higher level of T7 polymerase expression by FP-T7 could result in higher production levels of the N and L proteins from the antigenomic (i.e. positive-sense) genome segments, facilitating initiation of replication. To test this hypothesis, the pUC57-S segment was transfected into BSR-T7/5 cells and into BHK-21 cells that were previously infected with FP-T7. Transcription of the pUC57-S plasmid by T7 polymerase results in antigenomic sense viral RNA of which the N gene is in sense orientation. Whereas the N protein could not be detected in BSR-T7/5 cells transfected with pUC57-S (FIG. 1A), FP-T7-infected BHK-21 cells that were transfected with this plasmid stained intensely with anti-N antibodies (FIG. 1B).

We then proceeded with co-transfection of pUC57-S, pUC57-L and pUC57-Mv-eGFP(−) in FP-T7-infected BHK-21 cells. Whereas in previous experiments using BSR-T7/5 cells, only a few eGFP-positive cells were observed, in these experiments, FACS analysis showed that 1.3% of the cells were positive for eGFP (FIG. 2). A similar experiment was performed where cells were co-transfected with pCAGGS-NSmGnGc. In this experiment, 2.5% of the cells were positive for eGFP (FIG. 2). Interestingly, the observation of clusters of eGFP-positive cells suggested local spread of VLPs containing the reporter minigenome (data not shown). After three days, the culture supernatant was collected and incubated with BHK-21 cells that were either untreated or transfected with the helper plasmids pCIneo-RVFV-L and pCAGGS-N. In cells that were transfected with helperplasmids, 1.3% was positive for eGFP expression (FIG. 2). Moreover, 0.9% of the cells that were not previously transfected with helperplasmids was positive for eGFP expression, demonstrating that we were successful in producing replicon particles that contain all three genome segments (FIG. 2).

Production of RRPs Containing Two Genome Segments.

To facilitate further optimization of the system, we aimed to produce RRPs that contain only two genome segments. To this end, a reporter minigenome was produced in which the gene encoding the NSs gene of the S segment was exchanged for the gene encoding eGFP (i.e. S-eGFP). Previous work demonstrated that the NSs gene is not essential for growth in tissue culture (Muller et al. 1995. Am J Trop Med Hyg 53: 405-411) and other studies demonstrated that a virus containing this deletion is viable (Ikegami et al. 2006. J Virol 80: 2933-2940). Co-transfection of the resulting plasmid, pUC57-S-eGFP(−) with pUC57-L resulted in expression of eGFP in a small percentage of cells. However, when pCAGGS-NSmGnGc was added to the transfection mixture, 21.5% of the cells were positive for eGFP, as determined by FACS analysis (FIG. 3). Incubation of BHK-21 cells with the collected supernatant resulted in 4.7% of positive cells when helper plasmids were not provided, whereas the number of cells increased to 28.7% when helper plasmids were included (FIG. 3).

Production of Stable BHK-21 Cell Lines that Produce the Gn and Gc Glycoproteins.

With the aim to produce a system for the continuous production of RRPs, stable cell lines were produced that constitutively produce the Gn and Gc proteins. Briefly, BHK-21 cells were transfected with pCIneo-GnGc and clones with integrated plasmids were grown in the presence of geneticin G-418. A number of clones were tested for Gn/Gc expression by IPMA. A highly positive antiserum from a naturally infected sheep did not reveal any Gn/Gc positive cells (data not shown). An antiserum derived from a sheep that was previously vaccinated with NDV-GnGc was, however, successfully used to identify positive clones. One of the clones clearly displayed the highest Gn and Gc expression level as revealed by IPMA, although the expression levels appeared low (FIG. 4). This clone was tested for expression of Gc by Western blotting of proteins from cell lysates. Using a previously described polyclonal antiserum specific for a Gc-derived peptide, Gc expression was clearly detected (FIG. 4C). This cell line was designated BHK-GnGc. To determine if VLPs were produced by these cells, supernatants were ultracentrifuged and the proteins present in the collected pellets were analyzed by Western blotting. The Gc protein was not detected in the pellet fractions, suggesting that either no VLPs were produced, or that glycoprotein production was too low to allow detection.

Use of a cell line that maintains the RVFV L and S-eGFP segments is essential for the efficient production of RRPs.

Production of RRPs by infection of BHK-21 cells with FP-T7 and subsequent introduction of plasmids providing the L segment, S-eGFP segment and pCAGGS-NSmGnGc resulted in a maximum of RRP titers of 10E3 to 10E4 TCID50/ml (data not shown). Although the BHK-GnGc cell line appeared not suitable for the constitutive large scale production of RRPs, it was striking to find that introduction of FP-T7 and subsequent introduction of plasmids providing the L segment, S-eGFP segment and pCAGGS-NSmGnGc, resulted in clusters of positive cells that were larger in both number and size than those obtained with normal BHK-21 cells.

A cell line maintaining the RVFV L and S-eGFP segments could be highly valuable for several applications, including high-throughput screens of antiviral agents outside biosafety containment facilities. We therefore aimed to produce a cell culture of which each cell contains the RVFV L and S-eGFP segment. To this end, the FP-T7 virus was introduced, followed by introduction of the plasmids providing the L segment and the S-eGFP segment. To facilitate spread of the L and S-eGFP segment, pCAGGS-NSmGnGc was introduced several times after passage of the cells. Using this method, cell lines of both wildtype BHK-21 cells as well as BHK-GnGc were obtained of which most, if not all, cells expressed the eGFP reporter. However, whereas repetitive passage of the eGFP-expressing BHK-21 cells resulted in loss of eGFP, passage of the eGFP-expressing BHK-GnGc cells did not result in any loss of eGFP expression. For at least 50 cell passages, eGFP expression in these cells remained unchanged. When not transfected, BHK-GnGc cells containing the RVFV replicons were found to produce very small amounts of RRPs, with a maximum yield of 10E2 TCID50/ml. Importantly, introduction of pCAGGS-NSmGnGc or pCAGGS-GnGc in these cells resulted in RRP titers of maximally 10E6.8 or 10E6.4 TCID50/ml, respectively (FIG. 5).

Efficient Production of RRPs Using NDV-GnGc.

Figure 6:
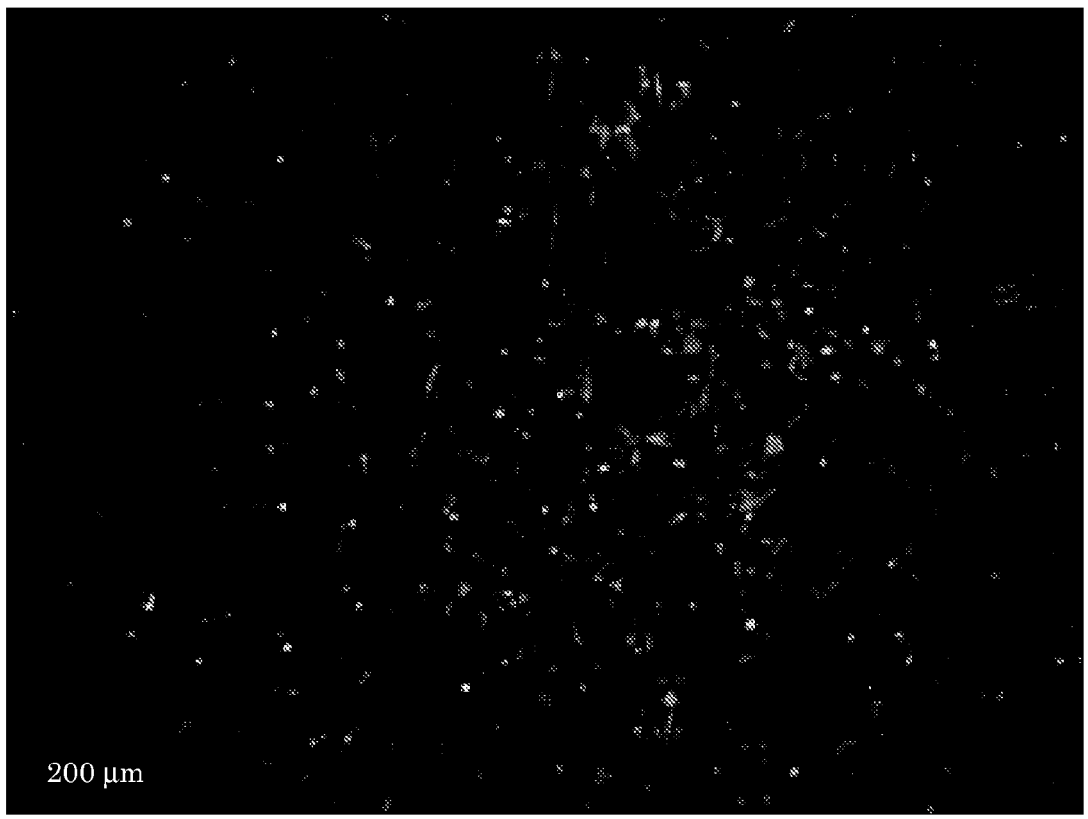

Considering the superior production of GnGc by NDV when compared to expression from plasmid, we tested if RRPs could be produced by infection of the cells with NDV-GnGc. BHK-GnGc cells were co-infected with FP-T7 and NDV-GnGc and, after recovery, were transfected with pUC57-L and pUC57-S-eGFP(−). After 72 hrs of incubation, extremely large "comets" of positive cells were observed in the flasks (data not shown). This result suggested that large amounts of RRPs are produced when NDV-GnGc is used to provide the glycoproteins. We subsequently split the culture into two flasks. One was left untreated, the other was again infected with NDV-GnGc. The supernatants of these cells were collected after 48 h and the TCID50 RRP titers were determined on BHK-21 cells. The supernatant of the cells that were infected with NDV-GnGc twice, contained a titer of 10E7 TCID50/ml, whereas the supernatant of the cells that were infected only once contained a titer of 10E4.5 TCID50/ml. The latter cell line was passaged 18 times, after which the RRP titer was again determined. Surprisingly, this revealed a titer of 10E6 TCID50/ml. Moreover, visual examination of this cell line by fluorescence microscopy revealed that most, if not all, cells expressed eGFP (FIG. 6). This result led us to suggest that the cells were persistently infected with NDFL-GnGc, thereby providing a continuous source of Gn and Gc. Indeed, IPMAs using a mAb specific for the NDV F protein, revealed the presence of the virus in a subset of the cells. It is important to note, however, that the virus present in the supernatant of these cells was shown to be non-infectious. This was expected however, since lentogenic NDV strains such as the recombinant LaSota strain used in the current work, requires cleavage of the F protein by trypsin-like proteases for infectivity. In conclusion, by virtue of the persistent infection of the cells with NDFL-GnGc, RRPs can continuously be produced to titers of up to 10E7 TCID50/ml.

Figure 8:
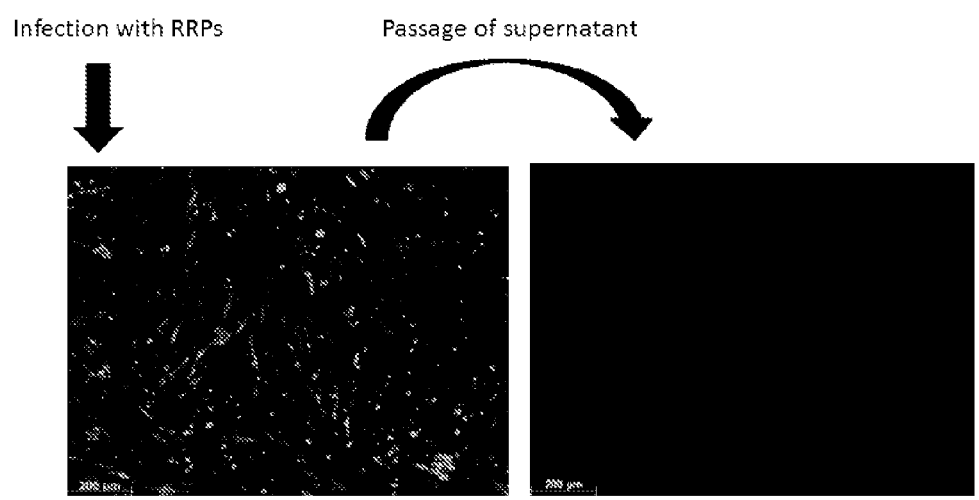
Figure 9:
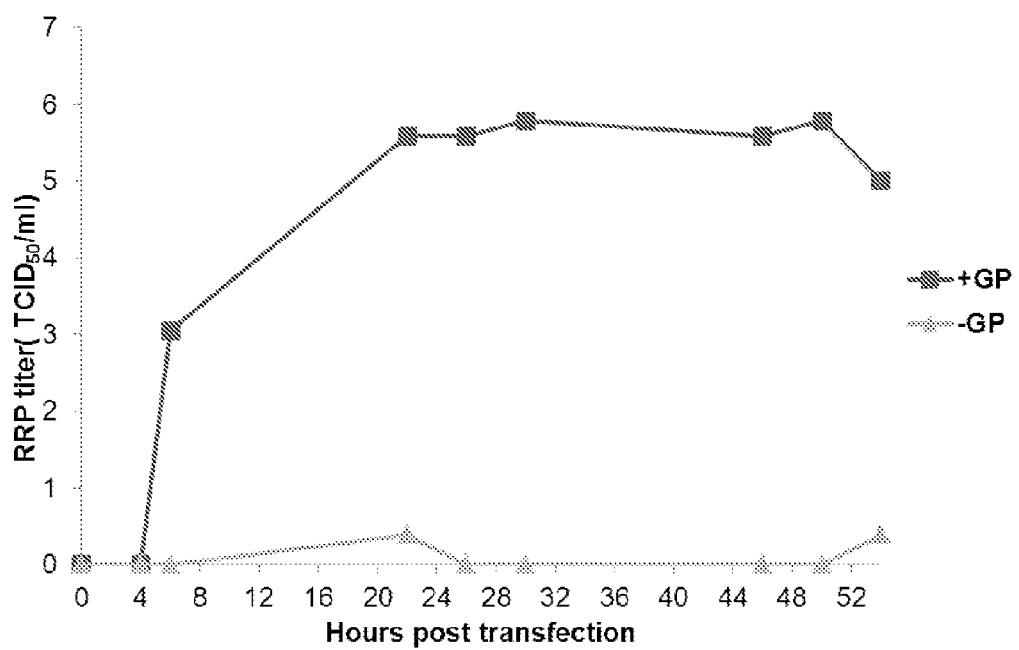

To demonstrate that RRPs are incapable of autonomous spread, BHK cells were infected with RRPs at a multiplicity of infection (m.o.i.) of 1. After two days, eGFP expression was observed by fluorescence microscopy (FIG. 8, left panel). BHK cells were incubated with collected pre-cleared supernatant and after three days, cells were monitored for eGFP expression. No eGFP expression was observed, demonstrating that no progeny infectious particles were produced by the RRP-infected BHK cells (FIG. 8, right panel). To establish the kinetics of RRP production, BHK-rep cells were transfected with pCAGGS-NSmGnGc and the culture medium was collected at different time points post transfection. RRPs were titrated on BHK cells using eGFP expression as the readout parameter. This experiment demonstrated that a titer close to 106 TCID50/ml was obtained already after 22 h (FIG. 9).

Figure 10:
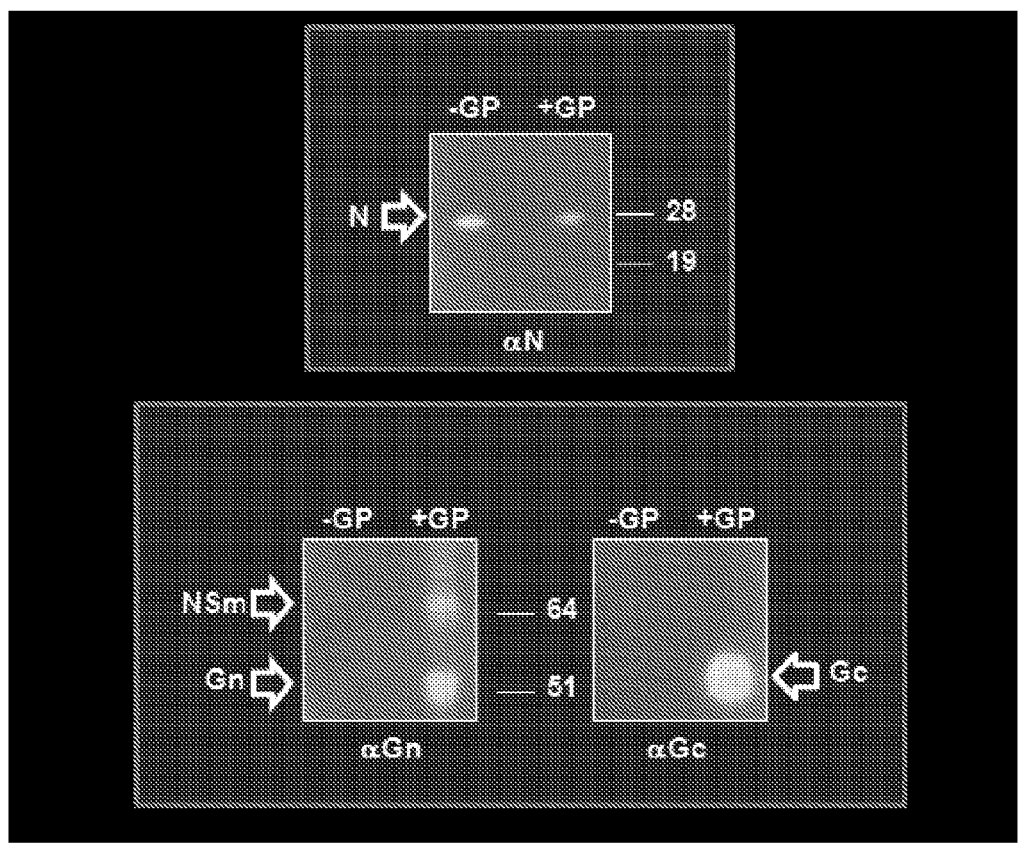

To visualize RRP proteins, RRPs were pelleted by ultracentrifugation. The proteins were separated in NuPAGE gels, transferred to nitrocellulose membranes and detected using peptide antisera specific for the Gn and Gc protein or a monoclonal antibody specific for the N protein. Analysis of the supernatant obtained from non-transfected BHK-Rep cells revealed only the N protein (FIG. 10). Interestingly, this result suggests that the RVFV N protein is released from cells, presumably in the form of ribonucleoprotein core particles, resembling results previously described from studies on CCHFV (Bergeron et al., 2007. J Virol 81: 13271-13276). Analysis of supernatant from BHK-Rep cells transfected with pCAGGS-NSmGnGc (pCAGGS-M) revealed the Gn protein, the NSm protein, the Gc protein and the N protein (FIG. 10).

Example 2

Production of Bunyavirus Replicon Particles (BRPs) of Crimean-Congo Hemorrhagic Fever Virus Strain IbAr10200 cDNA encoding anti virus-sense full-length RNA of the L (GenBank: AY389508.2), M (GenBank: AF467768.2) and S (GenBank: U88410.1) genome segments CCHFV strain IbAr10200 are synthesized and flanked by a T7 polymerase promoter and cDNA encoding a HDV ribozyme sequence. A T7 transcription termination sequence is preferably positioned downstream of the ribozyme cDNA. These sequences are cloned into pUC57 vectors essentially as exemplified in Example 1, resulting in pUC57-CCHFV-L, pUC57-CCHFV-M and pUC57-CCHFV-S.

To facilitate cloning into pUC57 of the cDNA encoding the CCHFV L genome segment, a KpnI restriction site is introduced immediately upstream of the T7 promoter sequence and immediately downstream of the T7 transcription termination sequence.

To facilitate cloning of the cDNA encoding the CCHFV M genome segment, a KpnI restriction site is introduced immediately upstream of the T7 promoter sequence and a SalI restriction site is introduced immediately downstream of the T7 transcription termination sequence.

To facilitate cloning of the cDNA encoding the CCHFV S genome segment, an EcoRI restriction site is introduced immediately upstream of the T7 promoter sequence and a BamHI restriction site is introduced immediately downstream of the T7 transcription termination sequence.

The complete open reading frame of the M genome segment (M-ORF, nucleotides 93-5147 of GenBank sequence AF467768.2) is introduced downstream of the CMV promoter of pCIneo. Stable cell lines are produced by transfecting pCIneo-M-ORF into BHK-21 cells and cells with integrated plasmids are selected by culturing in the presence of G-418.

As an alternative, BHK-21 cells are provided with the CCHFV M-ORF encoded proteins by infecting the eukaryotic cell with a recombinant viral vector that transduces the CCHFV M-ORF-encoded polyprotein, followed by selecting a cell in which the recombinant viral vector is persistently present without causing overt cytopathogenic effect.

The cells that (conditionally or constitutively) express the CCHFV M-ORF-encoded proteins are infected with FP-T7 and, after recovery, transfected with plasmids pUC57-CCHFV-L and pUC57-CCHFV-S. When required for efficient production, a construct encoding the CCHFV structural glycoproteins under the control of a suitable Polymerase-II promoter (such as the CAG promoter in the pCAGGS plasmid) is also transfected or infected to provide the CCHFV structural glycoproteins. This procedure results in the production of CCHFV replicon particles that do not contain a CCHFV M genome segment.

The T7 promoter that is used has the nucleotide sequence: 5'-TAATACGACTCACTATAG-3'

The HDV ribozyme sequence that is used has the nucleotide sequence 5'-GGGTCGGCATGGCATCTCC-3'.

The T7 terminator sequence that is used has the nucleotide sequence: 5-TAGCATAACCCCTTGGGGC-CTCTAAACGGGTCTTGAGGGGTTTTTTG-3'

Example 3

Production of bunyavirus replicon particles (BRPs) of Dobrava-Belgrade virus (DOBV) strain DOBV/Ano-Poroia/Afl9/1999 cDNA encoding anti virus-sense full-length RNA of the L (GenBank: AJ410617.1), M (GenBank: AJ410616.1) and S (GenBank: AJ410615.1) genome segments DOBV strain DOBV/Ano-Poroia/Afl9/1999 is synthesized and flanked by a T7 polymerase promoter and cDNA encoding a HDV ribozyme sequence. A T7 transcription termination sequence is preferably present downstream of the introduced ribozyme cDNA. These sequences are cloned into pUC57 vectors essentially as exemplified in Example 1, resulting in pUC57-DOBV-L, pUC57-DOBV-M and pUC57-DOBV-S.

To facilitate cloning into pUC57 of the cDNA encoding the DOBV L genome segment, a BamHI restriction site is introduced immediately upstream of the T7 promoter sequence and immediately downstream of the T7 transcription termination sequence.

To facilitate cloning of the cDNA encoding the DOBV M genome segment, a KpnI restriction site is introduced immediately upstream of the T7 promoter sequence and a SalI restriction site is introduced immediately downstream of the T7 transcription termination sequence.

To facilitate cloning of the cDNA encoding the DOBV S genome segment, a KpnI restriction site is introduced immediately upstream of the T7 promoter sequence and a SalI restriction site is introduced immediately downstream of the T7 transcription termination sequence.

The complete open reading frame of the M genome segment (MDOBV-ORF, nucleotides 41-3448 of GenBank sequence AJ410616.1) is introduced downstream of the CMV promoter of pCIneo. Stable cell lines are produced by transfecting pCIneo-MDOBV-ORF into BHK-21 cells and selecting cells with integrated plasmids by culturing in the presence of G-418.

Alternatively, the eukaryotic cell is provided with MDOBV-ORF-encoded proteins by infecting the eukaryotic cell with a recombinant viral vector that produces the MDOBV proteins, followed by selecting a cell in which the recombinant viral vector is persistently present without causing overt cytopathogenic effect.

The cells that (conditionally or constitutively) express the MDOBV-ORF-encoded proteins are infected with FP-T7 and, after recovery, transfected with plasmids pUC57-DOBV-L and pUC57-DOBV-S. When required for efficient production, a construct encoding the DOBV structural glycoproteins under the control of a suitable Polymerase-II promoter (such as the CAG promoter in the pCAGGS plasmid) is also transfected or infected to provide the DOBV structural glycoproteins. This procedure results in the production of DOBV replicon particles.

The T7 promoter that is used has the nucleotide sequence: 5'-TAATACGACTCACTATAG-3'

The HDV ribozyme sequence that is used has the nucleotide sequence 5'-GGGTCGGCATGGCATCTCC-3'.

The T7 terminator sequence that is used has the nucleotide sequence: 5-TAGCATAACCCCTTGGGGC-CTCTAAACGGGTCTTGAGGGGTTTTTTG-3'

Example 4

Tet-Off system for the inducible expression of RVFV NSm, Gn and Gc proteins

BHK-21 cells are transfected with the pTet-Off Advanced plasmid (Clontech, CA, USA) according to the instructions of the manufacturers. After selection with G-418, resistant clones are selected, yielding a BHK-Tet-Off Advanced cell line.

The complete open reading frames of the M segment of a RVFV strain 35/74, (nucleotides 21-3614) are synthesized with flanked KpnI (5' end) and NotI and SalI (3' end) restriction sites and cloned into pUC57 using KpnI and SalI restriction sites (GenScript Corporation). The inserts are released from the pUC57 plasmids by KpnI/NotI digestion and cloned into the KpnI/NotI-digested pTREtight vector (Clontech).

The BHK-Tet-Off Advanced cells are transfected with pTREtight-NSmGnGc and a linear marker that facilitates the selection of transfected cells by hygromycin or puromycin. Clones that produce the proteins of interest are selected by growing the clones in the absence of doxycycline (DOX).

After selection of suitable clones, the cells are grown in the presence of DOX and infected with FP-T7. After recovery, the cells are transfected with pUC57-L and pUC57-S-eGFP. After recovery, the culture medium of the cells is replaced by

Example 5

RVFV Replicon Particles that Produce Recombinant Soluble Multimeric HA of Pandemic Swine-Origin 2009 A (H1N1) Influenza Virus Oligo MSC-1 and Oligo MSC-2 are synthesized. Annealing of Oligo MCS-1 and Oligo MCS-2 results in a double-stranded DNA molecule containing NcoI and XbaI overhangs and additional SpeI, XhoI, BglI, NotI restriction sites.

```
Oligo MCS 1:
5'-CATGGACTAGTCTCGAGGCTAGCAGATCTGCGGCCGCT-3'

Oligo MCS 2:
5'-CTAGAGCGGCCGCAGATCTGCTAGCCTCGAGACTAGTC-3'
```

The eGFP gene is removed from pUC57-S-eGFP (FIG. 7F) by NcoI/XbaI digestion and the MCS linker is ligated into this vector, yielding pUC57-S-MCS.

The sequence listed below (Seq CD5-HA-GCN4-ST) encodes a human codon-optimized soluble hemagglutinin ectodomain (sHA, amino acids 17 to 522) of influenza virus A/California/04/2009 (H1N1). This sequence is synthesized at the GenScript Corporation. The HA gene is preceded by a sequence encoding an N-terminal CD5 signal peptide and followed by sequences encoding a C-terminal artificial GCN4 trimerization domain (GCN4-pII, Harbury et al. 1993. Science 262: 1401-1407) and a Streptavidin-tag (Strep) for affinity purification. This construct is described in Bosch et al. 2010. J. Virol. 84: 10366-10374).

To generate a vector comprising CD5-sHA-GCN4-pII, pUC57-S-MCS is digested with NheI/XbaI and NheI/XbaI digested HA-GCN4-ST sequence is cloned into this plasmid, yielding pUC57-S-HA-GCN4-ST. The CD5 sequence is subsequently introduced by annealing of the following oligo's:

```
Oligo CD5-1:
5'-CTAGTATGCCCATGGGGTCTCTGCAACCGCTGGCCACCTTGTACCTGCTG
GGGATGCTGGTCGCTTCCGTG-3'

Oligo CD5-2:
5'-CTAGCACGGAAGCGACCAGCATCCCCAGCAGGTACAAGGTGGCCAGCGG
TTGCAGAGACCCCATGGGCATA-3'
```

The CD5 linker is ligated into SpeI/NheI-digested pUC57-S-HA-GCN4-ST, yielding pUC57-S-CD5-HA-GCN4-ST.

BHK-GnGc cells are infected with FP-T7. After recovery, the cells are transfected with pUC57-L, pUC57-S-CD5-HA-GCN4-ST and pCAGGS-NSmGnGc, essentially as exemplified in Example 1. After cell passage, the transfection is repeated. This sequence of events is repeated until all the cells of the monolayer express the CD5-HA-GCN4-ST protein, as is determined by IPMA. The quantity of HA-GCN4-ST in the culture medium of these cells is determined. To establish high levels of NSmGnGc proteins, plasmid pCAGGS-NSmGnGc is again introduced in the cell line, yielding replicon particles containing the S-CD5-HA-GCN4-ST gene. The replicon particles are used for vaccination/challenge experiments in mice to establish the protective efficacy against a lethal H1N1 challenge.

Seq. CD5-HA-GCN4-ST
Nucleotides 1-69 (underlined) encode the CD5 sequence
Nucleotides 70-1590 encode the HA ectodomain
Nucleotides 1591-1713 (underlined) encode the GCN4 domain
Nucleotides 1714-1737 encode the Strep tag

```
atgcccatggggtctctgcaaccgctggccaccttgtacctgctggggatgctggtcgct
 M   P   M   G   S   L   Q   P   L   A   T   L   Y   L   L   G   M   L   V   A tccgtgctagcagacaccctgtgcatcggctaccacgccaacaacagcaccgacaccgtg
 S   V   L   A   D   T   L   C   I   G   Y   H   A   N   N   S   T   D   T   V gacaccgtgctggagaagaacgtgaccgtgacccacagcgtgaacctgctggaggacaag
 D   T   V   L   E   K   N   V   T   V   T   H   S   V   N   L   L   E   D   K cacaacggcaagctgtgcaagctgcgcggcgtggctccactgcacctgggcaagtgcaac
 H   N   G   K   L   C   K   L   R   G   V   A   P   L   H   L   G   K   C   N attgctggatggatcctgggaaacccagagtgcgagagcctgagcaccgccagcagctgg
 I   A   G   W   I   L   G   N   P   E   C   E   S   L   S   T   A   S   S   W agctacatcgtggagacccccagcagcgacaacggcacctgctaccccggcgacttcatc
 S   Y   I   V   E   T   P   S   S   D   N   G   T   C   Y   P   G   D   F   I gactacgaggagctgcgcgagcagctgagcagcgtgagcagcttcgagcgcttcgagatc
 D   Y   E   E   L   R   E   Q   L   S   S   V   S   S   F   E   R   F   E   I ttccccaagaccagcagctggccaaaccacgacagcaacaagggagtgaccgctgcttgc
 F   P   K   T   S   S   W   P   N   H   D   S   N   K   G   V   T   A   A   C ccacacgctggagccaagagcttctacaagaacctgatctggctggtgaagaagggcaac
 P   H   A   G   K   S   F   Y   K   N   L   I   W   L   V   K   K   G   N agctaccccaagctgagcaagagctacatcaacgacaagggcaaggaggtgctggtgctg
 S   Y   P   K   L   S   K   S   Y   I   N   D   K   G   K   E   V   L   V   L tggggcatccaccaccccagcaccagcgccgaccagcagagcctgtaccagaacgccgac
 W   G   I   H   H   P   S   T   S   A   D   Q   Q   S   L   Y   Q   N   A   D acctacgtgttcgtgggcagcagccgctacagcaagaagttcaagcccgagatcgccatc
```

-continued

```
 T  Y  V  F  V  G  S  S  R  Y  S  K  K  F  K  P  E  I  A  I cgccccaaggtgcgcgaccaggagggccgcatgaactactactggaccctggtggagccc
 R  P  K  V  R  D  Q  E  G  R  M  N  Y  Y  W  T  L  V  E  P ggcgacaagatcacctttgaggctaccggaaacctggtggtgccacgctacgcttttgct
 G  D  K  I  T  F  E  A  T  G  N  L  V  V  P  R  Y  A  F  A atggagaggaatgctggcagcggcatcatcatcagcgacaccccgtgcacgactgcaac
 M  E  R  N  A  G  S  G  I  I  I  S  D  T  P  V  H  D  C  N accacctgccagacccccaagggcgccatcaacaccagcctgcccttccagaacatccac
 T  T  C  Q  T  P  K  G  A  I  N  T  S  L  P  F  Q  N  I  H cccatcaccatcggcaagtgccccaagtacgtgaagagcaccaagctgcgcctggccacc
 P  I  T  I  G  K  C  P  K  Y  V  K  S  T  K  L  R  L  A  T ggactgaggaacatcccaagcatccagagccgcggcctgtttggagctattgctggattc
 G  L  R  N  I  P  S  I  Q  S  R  G  L  F  G  A  I  A  G  F attgagggcggctggaccggaatggtggatggatggtacggctaccaccaccagaacgag
 I  E  G  G  W  T  G  M  V  D  G  W  Y  G  Y  H  H  Q  N  E cagggcagcggctacgccgccgacctgaagagcacccagaacgccatcgacgagatcacc
 Q  G  S  G  Y  A  A  D  L  K  S  T  Q  N  A  I  D  E  I  T aacaaggtgaacagcgtgatcgagaagatgaacacccagttcaccgccgtgggcaaggag
 N  K  V  N  S  V  I  E  K  M  N  T  Q  F  T  A  V  G  K  E ttcaaccacctggagaagcgcatcgagaacctgaacaagaaggtggacgacggcttcctg
 F  N  H  L  E  K  R  I  E  N  L  N  K  K  V  D  D  G  F  L gacatctggacctacaacgccgagctgctggtgctgctggagaacgagcgcaccctggac
 D  I  W  T  Y  N  A  E  L  L  V  L  L  E  N  E  R  T  L  D taccacgacagcaacgtgaagaacctgtacgagaaggtgcgcagccagctgaagaacaac
 Y  H  D  S  N  V  K  N  L  Y  E  K  V  R  S  Q  L  K  N  N gccaaggagatcggcaacggctgcttcgagttctaccacaagtgcgacaacacctgcatg
 A  K  E  I  G  N  G  C  F  E  F  Y  H  K  C  D  N  T  C  M gagagcgtgaagaacggcacctacgactaccccaagtacagcgaggaggccaagctgaac
 E  S  V  K  N  G  T  Y  D  Y  P  K  Y  S  E  E  A  K  L  N Cgcgaggagatcgacggcgtgaagctcgagttaattaagcgcatgaagcagatcgaggac
 R  E  E  I  D  G  V  K  L  E  L  I  K  R  M  K  Q  I  E  D aagatcgaagagatcgagtccaagcagaagaagatcgagaacgagatcgcccgcatcaag
 K  I  E  E  I  E  S  K  Q  K  K  I  E  N  E  I  A  R  I  K Aagattaagctggtgccgcgcggcagcctcgagtggagccacccgcagttcgagaagtga
 K  I  K  L  V  P  R  G  S  L  E  W  S  H  P  Q  F  E  K  -
```

Example 6

RRP Infection of Mammalian and Insect Cells and Production of RRPs

Figure 11:
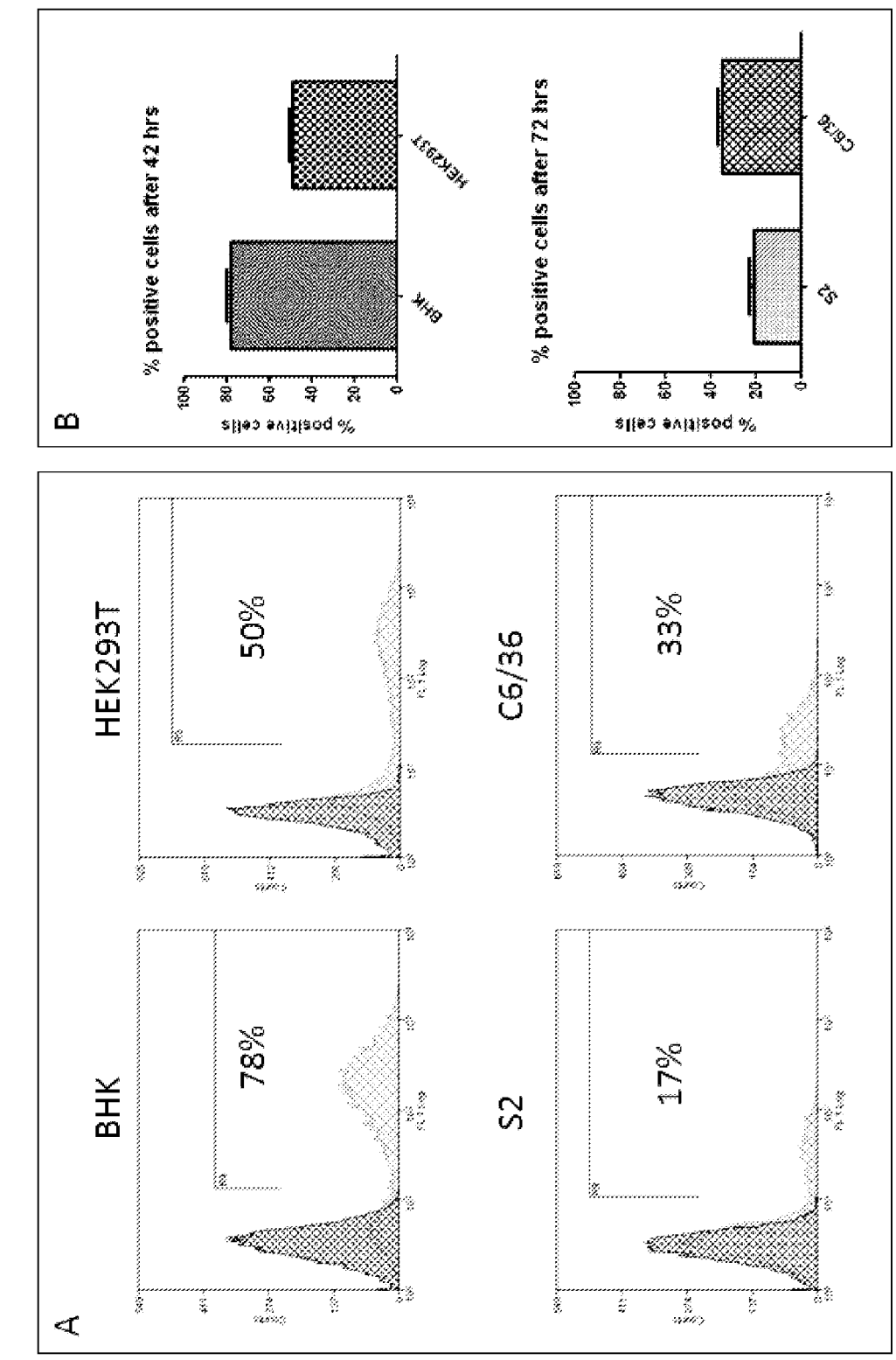

To determine if other mammalian and insect cells can be infected with RRPs, Human Embryonic Kidney 293 cells (HEK293T), *Drosophila* S2 cells and *Aedes albopictus* C6/36 cells were infected with RRPs at an m.o.i. of 1. Of note, the m.o.i. was calculated using the titer determined on BHK cells. This experiment demonstrated that both mammalian and insect cells can be readily infected with RRPs, although reporter gene expression in insect cells is considerably lower (FIG. 11A). Expression of eGFP in mammalian cells and insect cells was optimal at 42 or 72 hours post infection (hpi), respectively (FIG. 11).

Next, we were interested in determining if HEK293T cells can be used for the production of RRPs. To this end, BHK cells and HEK293T cells were infected with RRPs at an m.o.i. of 3. After three days, the cells were seeded in a 6-well plate and transfected with pCAGGS-NSmGnGc. The supernatant was collected after three days and the RRP titers obtained were 10E7 ($10^7$) or BHK cells and 10E6.5 ($10^{6.5}$) TCID50/ml for HEK293T cells. This result demonstrates that wildtype BHK cells and HEK293T cells can be used for the production of RRPs by combining an RRP infection with a transfection of the pCAGGS-NSmGnGc plasmid

Example 7

Use of RRPs in a Virus Neutralization Test (VNT)

Classical VNT and a novel VNT that uses RRPs instead of live virus (RaPid VNT) were performed with sera from lambs that were previously experimentally infected with the 35/74 virus. To confirm the presence of RVFV-specific antibodies, the sera were analyzed by the recN RVFV ELISA (BDSL, Ayrshire Scotland, UK) prior to analysis by VNT. The classical VNT was performed as described previously (de Boer et al., 2010. Vaccine 28: 2330-2339). For the RaPid VNT, serum dilutions were prepared in 96-well plates in 50 μl GMEM supplemented with 5% FBS, 4% TPB, 1% MEM NEAA, 1% pen/strep. Growth medium containing ~200 RRPs in a 50 μl volume was added to the serum dilutions and incubated for 1.5 h at room temperature. Next, 50 µl of growth medium containing 40 000 BHK cells was added to each well. Plates were incubated at 37° C. and 5% CO2. After 36-48 hrs the neutralization titer was calculated using the Spearman-Kärber method (Karber (1931). Arch Exp Path Pharmak 162:480-483; Spearman (1908). Br J Psychol 2: 227-242).

TABLE 1

Comparison of the classical VNT assay with the RaPid VNT.
Sera from experimentally infected lambs were analysed by the recN ELISA (ELISA), classical VNT, and RaPid VNT. Neutralization titres are determined as $^{10}$log 50% end-point titres.

| Lamb no: | Classical VNT | RaPid VNT | ELISA |
|---|---|---|---|
| 4308 | 3.56 | 3.94 | POS |
| 4309 | 4.09 | 4.16 | POS |
| 4310 | 0 | 0 | NEG |
| 4311 | 4.01 | 4.24 | POS |
| 4312 | 3.71 | 4.76 | POS |
| 4314 | 3.56 | 4.46 | POS |
| 4315 | 3.71 | 4.39 | POS |
| 4318 | 4.16 | 4.39 | POS |
| 4321 | 0 | 0 | NEG |
| 4324 | 4.24 | 4.31 | POS |
| 4328 | 4.01 | 4.69 | POS |

This experiment revealed that the use of RRPs in the so-called RaPid VNT has an optimal readout between 36 and 48 hrs and is of equal, if not higher sensitivity than the classical VNT (Table 1).

Example 8

Vaccination and Challenge of Mice

Female BALB/c mice (Charles River laboratories, Maastricht, The Netherlands) were housed in groups of five animals in type-III filter-top cages and kept under biosafety level-3 containment. Groups of 10 mice were vaccinated via the intramuscular or subcutaneous route either once on day 21 or two times on days 0 and 21 with 10E6 TCID50 of RRPs in 50 µl PBS. One group of nine mice was left untreated (non-vaccinated). The body weights of the mice were monitored weekly. On day 42, all mice were challenged via the intraperitoneal route with 10E2.7 TCID50 of RVFV strain 35/74 in 0.5 ml culture medium. Challenged mice were monitored daily for visual signs of illness and mortality. This experiment was approved by the Ethics Committee for Animal Experiments of the Central Veterinary Institute of Wageningen University and Research Centre.

Figure 12:
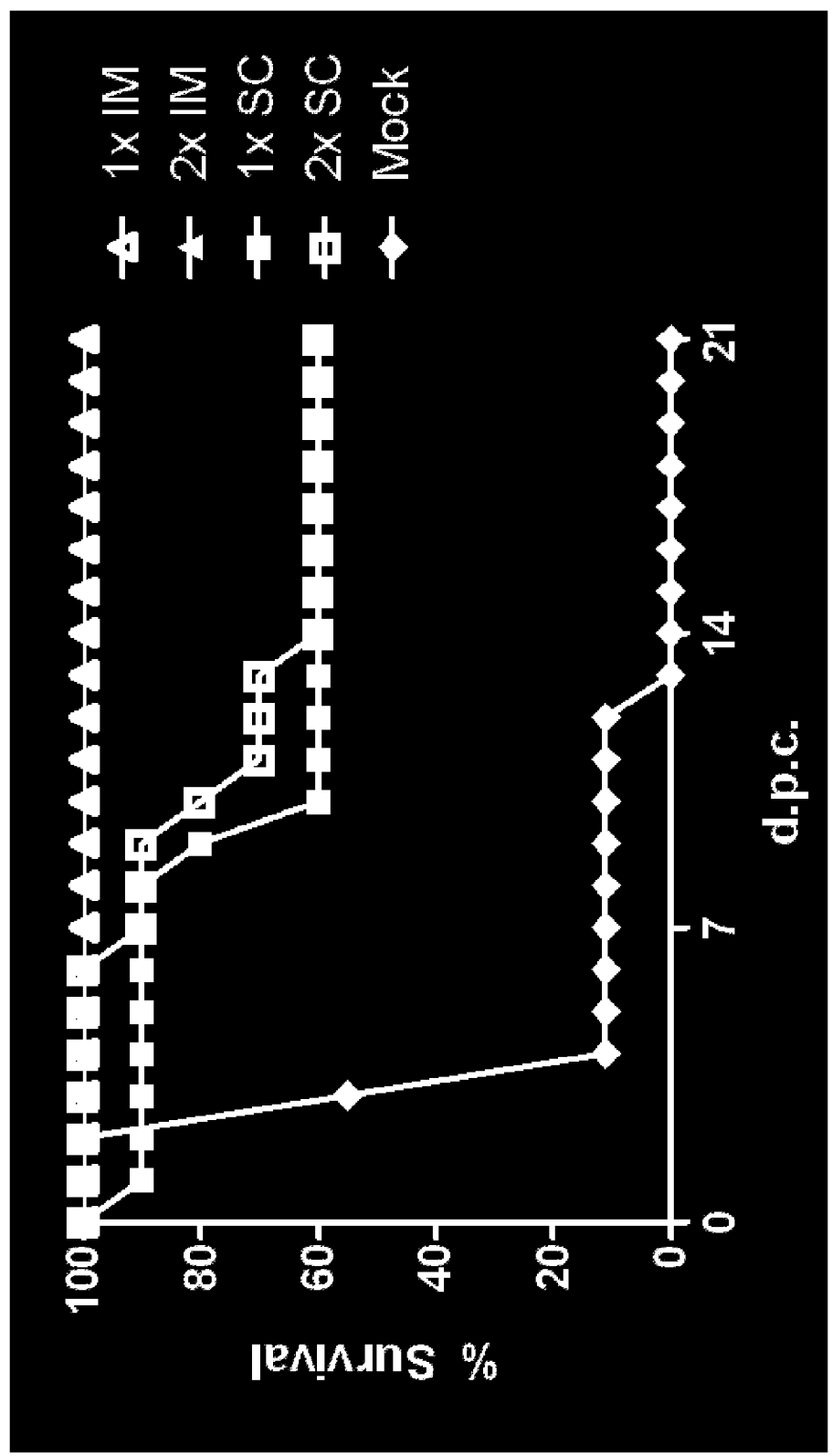

To study the vaccine efficacy of RRPs, groups of 10 mice were immunized with 50 µl of an inoculum containing 10E6 TCID50 RRPs, via either the subcutaneous or intramuscular route, either once or twice, with a three week interval. One group of 9 non-vaccinated mice was added as a control group. The mice were challenged on day 42 with a known lethal dose of RVFV strain 35/74. All non-vaccinated mice displayed overt clinical signs and weight loss and eight of a total of nine non-vaccinated mice succumbed to the infection within four days after challenge. One mouse survived for twelve days, but eventually died. The percentage of survival in the groups of mice vaccinated either once or twice via the subcutaneous route was 60% (FIG. 12). In contrast, 100% of the mice vaccinated via the intramuscular route, either once or twice, survived the challenge (FIG. 12). These mice did not show any clinical signs or weight loss throughout the experiment. This demonstrates that a single intramuscular vaccination with 10E6 RRPs can protect mice from a lethal dose of RVFV.

Example 9

Production of Bunyavirus Replicon Particles of Severe Fever with Thrombocytopenia Syndrome (SFTS) Virus Isolate HB29

SFTS virus was first described by Yu et al. (Yu X J, et al. Fever with Thrombocytopenia Associated with a Novel Bunyavirus in China. N Engl J Med 2011 Mar. 16).

cDNAs encoding full-length viral RNA corresponding to the L (GenBank: HM745930.1), M (GenBank: HM745931.1) and S (GenBank: HM745932.1) genome segments of SFTS virus isolate HB29 are synthesized and flanked by a T7 polymerase promoter and cDNA encoding a HDV ribozyme sequence. A T7 transcription termination sequence is preferably positioned downstream of the ribozyme cDNA. These sequences are cloned into pUC57 vectors essentially as exemplified in Example 1, resulting in pUC57-SFTS-L, pUC57-SFTS-M and pUC57-SFTS-S.

To facilitate cloning into pUC57 of the cDNA encoding the SFTS L genome segment, a KpnI restriction site is introduced immediately upstream of the T7 promoter sequence and immediately downstream of the T7 transcription termination sequence.

To facilitate cloning of the cDNA encoding the SFTS M genome segment, a KpnI restriction site is introduced immediately upstream of the T7 promoter and immediately downstream of the T7 transcription termination sequence.

To facilitate cloning of the cDNA encoding the SFTS S genome segment, a KpnI restriction site is introduced immediately upstream of the T7 promoter sequence and immediately downstream of the T7 transcription termination sequence.

An additional construct encoding an SFTS S genome-like segment in which the NSs gene (nucleotides 835-1716 of GenBank: HM745932.1) is replaced by a gene encoding a suitable reporter protein (i.e. eGFP or luciferase) is also developed. A plasmid encoding an S-like genome segment in which the NSs gene is replaced by the eGFP gene is named pUC57-SFTS-S-eGFP. Similar as was shown for RVFV, introduction of the SFTS-L and SFTS-S-eGFP genome segments in suitable cells (e.g. BHK-21 cells) results in viable cells maintaining these genome segments.

The complete open reading frame of the M genome segment (M-ORF, nucleotides 19-3240 of GenBank sequence HM745931.1) is introduced downstream of the CMV promoter of pCIneo. Stable cell lines are produced by transfecting pCIneo-SFTS-M-ORF into BHK-21 cells and cells with integrated plasmids are selected by culturing in the presence of G-418.

As an alternative, BHK-21 cells are provided with the SFTS-M-ORF encoded proteins by infecting the eukaryotic cell with a recombinant viral vector that transduces the SFTS M-ORF-encoded polyprotein and a cell line is selected in which the recombinant viral vector is persistently present without causing overt cytopathogenic effect.

The cells expressing the SFTS M-ORF-encoded proteins are infected with FP-T7 and, after recovery, transfected with plasmids pUC57-SFTS-L and either pUC57-SFTS-S or pUC57-SFTS-S-eGFP. When required for efficient production, a construct encoding the SFTS structural glycoproteins under the control of a suitable Polymerase-II promoter (such as the CAG promoter in the pCAGGS plasmid) is also transfected or infected to provide the SFTS structural glycoproteins. This procedure results in the production of SFTS replicon particles of isolate HB29 that do not contain an SFTS M genome segment.

The T7 promoter that is used has the nucleotide sequence: 5'-TAATACGACTCACTATAG-3'

The HDV ribozyme sequence that is used has the nucleotide sequence 5'-GGGTCGGCATGGCATCTCC-3'.

The T7 terminator sequence that is used has the nucleotide sequence: 5-TAGCATAACCCCTTGGGGC-CTCTAAACGGGTCTTGAGGGGTTTTTTG-3'

A similar method can be used to produce replicon particles of other SFTS isolates.

Example 10

Rapid Immunity Against RVFV in Sheep after a Single Vaccination with the NSR Vaccine Materials and Methods
Preparation of the Challenge Virus The RVFV virus that was used for challenge was rescued from cDNA (see Example 1 and Kortekaas et al. 2011. J. Virol. Accepted for publication). The recombinant 35/74 (rec35/74) virus was titrated on BHK-21 cells and the titer was determined as tissue culture infective dose 50 (TCID50) using the Spearman-Kärber algorithm (Example 1). The complete sequence of the L, M and S genome sequences of the 35/74 isolate can be found on GenBank under the accession numbers JF784386, JF784387 and JF784388, respectively.

2.2 Preparation of the Vaccines

The ectodomain of the Gn protein (GneS3) was produced from the insect expression vector pMT/BiP/V5-HisA (Invitrogen, Carlsbad, Calif., USA). The sequence encoding the authentic Gn signal peptide was replaced by a sequence coding for the BiP signal peptide, specifying the junction sequence "GLSLG-RSLRSLAEDPH", in which GLSLG denotes the BiP, RSLRSL denotes a linker sequence, and AEDPH the start of the Gn ectodomain. In the pMT-GneS3 plasmid, the Gn ectodomain sequence was fused to a sequence encoding a combined FLAG-tag/enterokinase (EK) cleavage site for easy detection and purification of the monomeric protein (DYKDDDDK) and three Strep tags (WSH-PQFEK) separated by glycine linkers (GGGSGGGSGGGS), resulting in the following sequence: ( . . . YQCHTDPT-GDYKDDDDKAGPGWSHPQFEK GGGSGGGSGGGSWSH-PQFEKGGGSGGGSGGGSWSHPQFEK in which the sequences resulting from introduced restriction sites are indicated in bold. The enterokinase cleavage site was introduced to allow removal of the Strep-tag after purification.

The secreted Gn ectodomain was purified from the cell culture supernatant by virtue of its C-terminal 3× Strep-tag using Strep-Tactin Sepharose according to the manufacturer's recommendations (IBA, Göttingen, Germany). The GneS3 protein was eluted from the washed beads with 4 mM D-Desthiobiotin (IBA) and concentrated using an Amicon® Ultra-4 concentrator with a molecular mass cut-off of 30 kDa (Millipore, Billerica, Mass., USA). The protein, named GneS3, was formulated in Stimune water-in-oil adjuvant (Prionics, Lelystad, The Netherlands) to a final concentration of 20 µg/ml.

Production of the NDFL-GnGc was previously reported (Kortekaas et al. 2010. Vaccine 28: 4394-4401). OBP vaccine is a commercially available inactivated RVFV vaccine (Onderstepoort Biological Products [OBP], Onderstepoort, South Africa). This vaccine was purchased from OBP and administered according to the instructions of the manufacturer. The administered doses and routes of vaccination of the four indicated vaccines are depicted in Table 2.

TABLE 2

Route and dose of vaccines

| Vaccine | Route | Dose | Adjuvant |
|---|---|---|---|
| OBP vaccine | Subcutaneous | According to protocol of manufacturer | Aluminium hydroxide gel |
| NDFL-GnGc | Intramuscular | $2.10^7$ $TCID_{50}$ | None |
| NSR | Intramuscular | $10^7$ $TCID_{50}$ | None |
| GneS3 | Subcutaneous | 20 µg | Stimune water-in-oil |

2.3 Vaccination and Challenge

Thirty conventional European breed lambs were purchased from a commercial sheep farm in The Netherlands and divided over five groups. Lambs were vaccinated once at the age of six weeks (day 0), as depicted in Table 2. On day 19 (days post challenge [DPC] 0), all lambs were challenged via the intraperitoneal route with $10^5$ TCID50 of RVFV rec35/74. EDTA blood samples were collected daily starting from day 19 (DPC 0) until day 26 (DPC 7) and again on days 28, 30, 33, 35, 37 and 40 (DPC 9, 11, 14, 15, 17 and 20). Serum samples were collected on days −7, 0, 7, 14, and daily from day 19 (day of challenge) to 26 (DPC 7) and finally on days 33 (DPC 14) and 40 (DPC 20). Body weights were determined weekly, on DPI −7, −1, 6, 13, 18, 25, 32 and 39. Rectal body temperatures were determined daily starting on day 17 (two days prior to challenge) until the end of the experiment.

2.4 Quantitative Real-Time PCR and ELISA

Viral RNA was isolated from plasma samples using the QuickGene DNA tissue kit S (DT-S, Fuji Photo Film Europe GmbH, Dusseldorf, Germany) with the following modifications. Proteinase K solution (EDT, DT-S kit, 30 µl) and 3 µl polyadenylic acid A (polyA 5 µg/µl, Sigma, St. Louis, Mo., USA) were added to 250 µl lysis buffer (LDT, DT-S kit). Of this mixture, 250 µl was added to 300 µl plasma. The mixture was heated at 72° C. for 10 min in a heating block and stored at −20° C. until further analysis. RNA isolation was subsequently performed using the QG-Mini80 Workflow (Fuji Film). The lysate was mixed with 350 µl 99% ethanol before loading on the column. After three wash steps with 750 µl wash buffer (WDT, DT-S kit) the RNA was eluted with 50 µl elution buffer (CDT, DT-S kit). The material was stored at −70° C. until further analysis.

RNA samples (5 µl) were used for quantitative Taqman reverse-transcriptase real-time PCR (qRRT-PCR). The Light-Cycler RNA Amplification Kit HybProbe (Roche, Almere, The Netherlands) was used and primers, probes and cycling conditions were used as previously described (Drosten et al. 2002 J Clin Microbiol 40: 2323-2330).

2.5 Clinical Chemistry

Clinical chemistry was performed with serum collected on the day of challenge (study day 19, DPC 0) and subsequently on days 20-25 (DPC 1-6), and on days 32 (DPC 14) and 38 (DPC 21). Enzyme analysis was performed using the Spotchem EZ SP-4430 analyser (Menarini Diagnostics, Valkenswaard, The Netherlands) using strips capable of detecting alkaline phosphatase (ALP), alanine transaminase (ALT), creatinine, glucose, total protein and urea.

On day 0, blood samples (n=30) were collected and used to define the upper and lower limits of blood parameters. Limits were set at the average upper and lower averages plus two times their standard deviations.

2.6 Statistical Analysis

Statistical analyses were performed with the one-way analysis of variance (ANOVA) with Bonferroni's multiple comparison test using GraphPad Prism version 5.00 for Windows (GraphPad Software, San Diego, Calif., USA). Statistical differences with p-values<0.05 were considered significant.

Results

Figure 13:
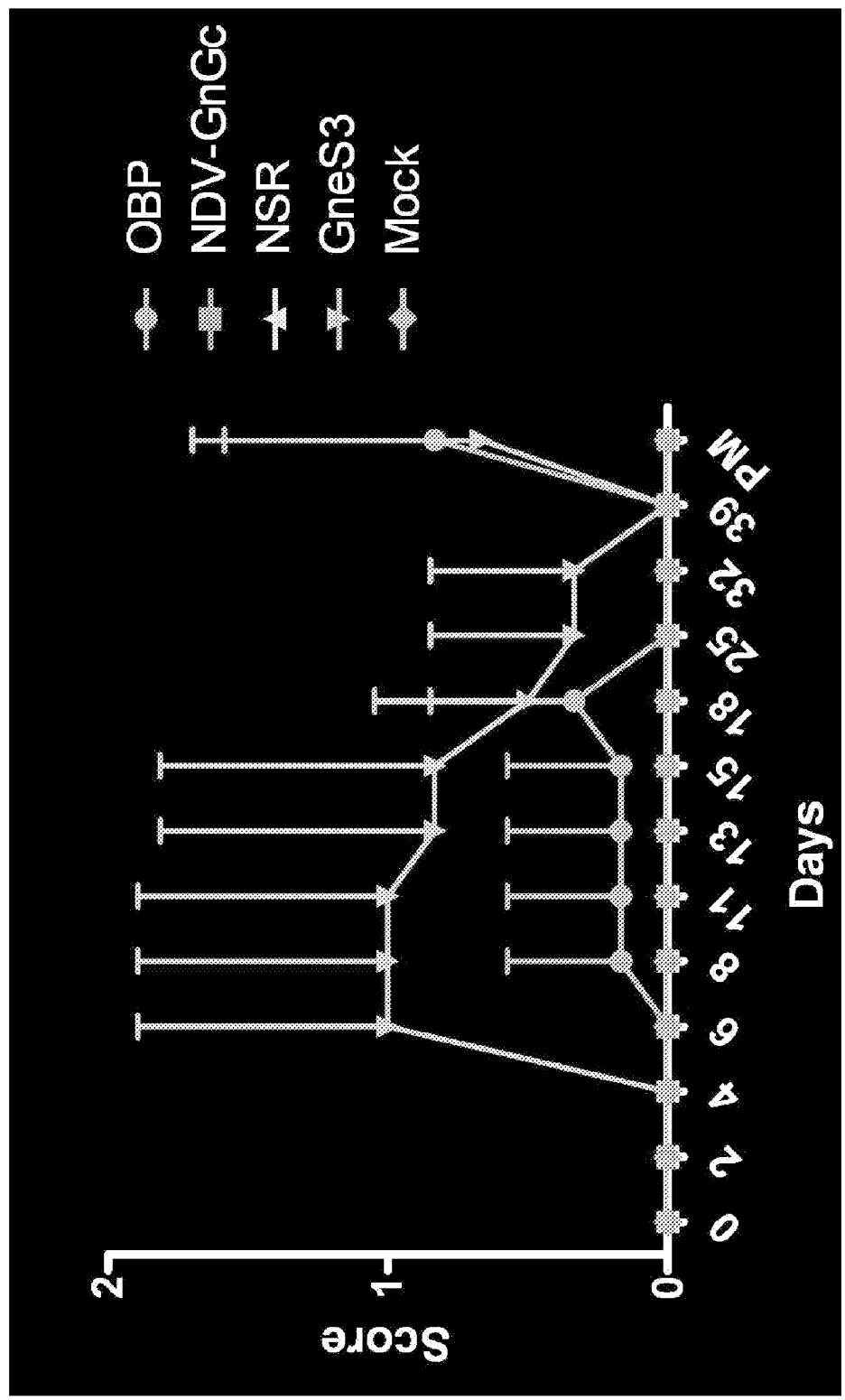

After acclimatization for one week, all lambs were vaccinated as depicted in Table 2. On different time points after vaccination, the injection sites were inspected for possible adverse reactions. These inspections revealed mild to moderate swelling in four and five out of six lambs vaccinated with the OBP and GneS3 vaccine, respectively. In the other groups, no injection site reactions were observed (FIG. 13). No adverse reactions at the injection site were observed in lambs vaccinated with the NDV-GnGc vaccine or the NSR vaccine.

Figure 14:
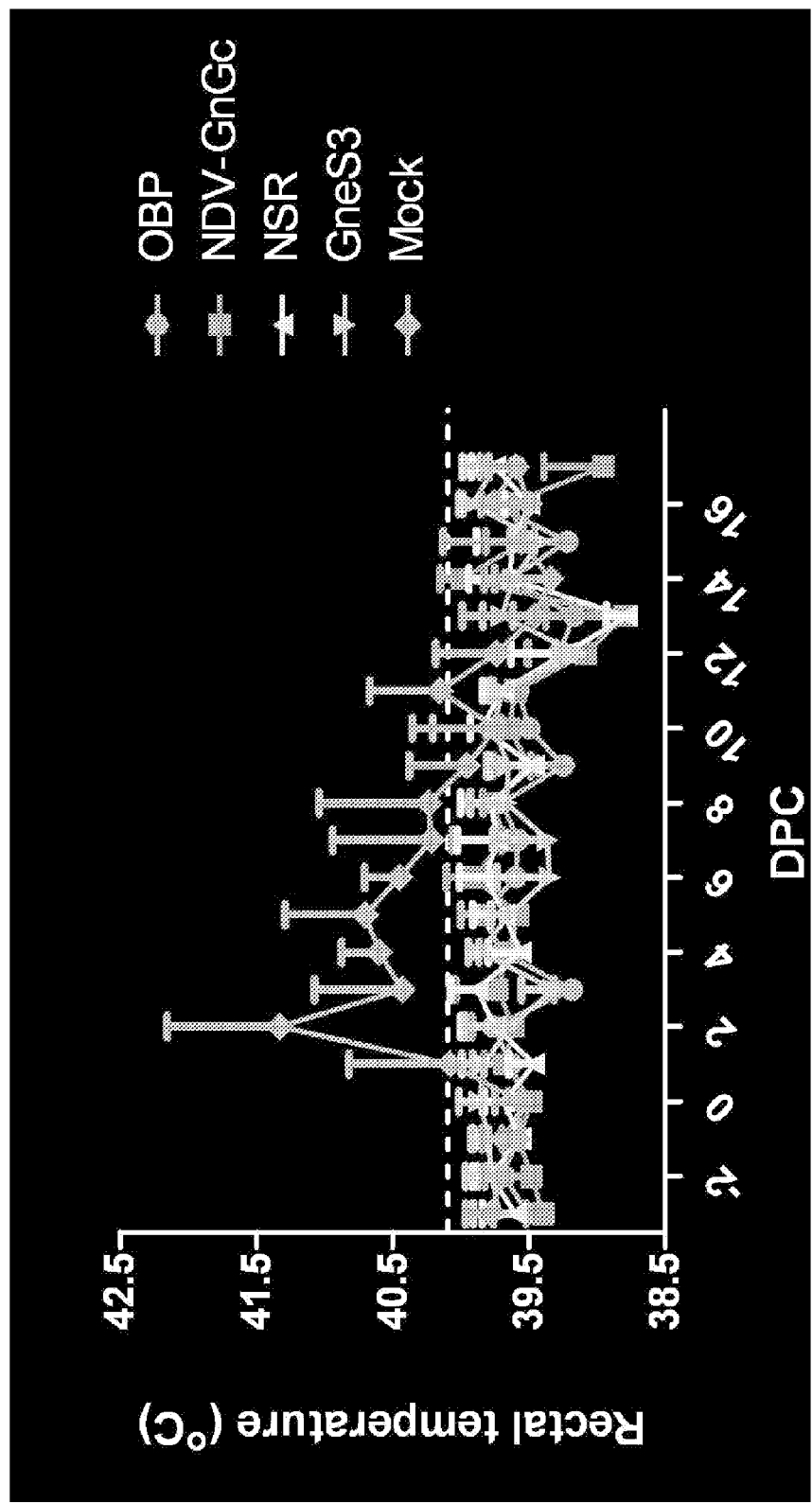

After challenge the rectal temperatures in the control group peaked at 2 DPC (FIG. 14). Peak rectal temperatures and the total days of fever (rectal body temperature ≥40.1° C.) were both significantly lower (p<0.0001) in all vaccinated groups, compared to the control group.

Figure 15:
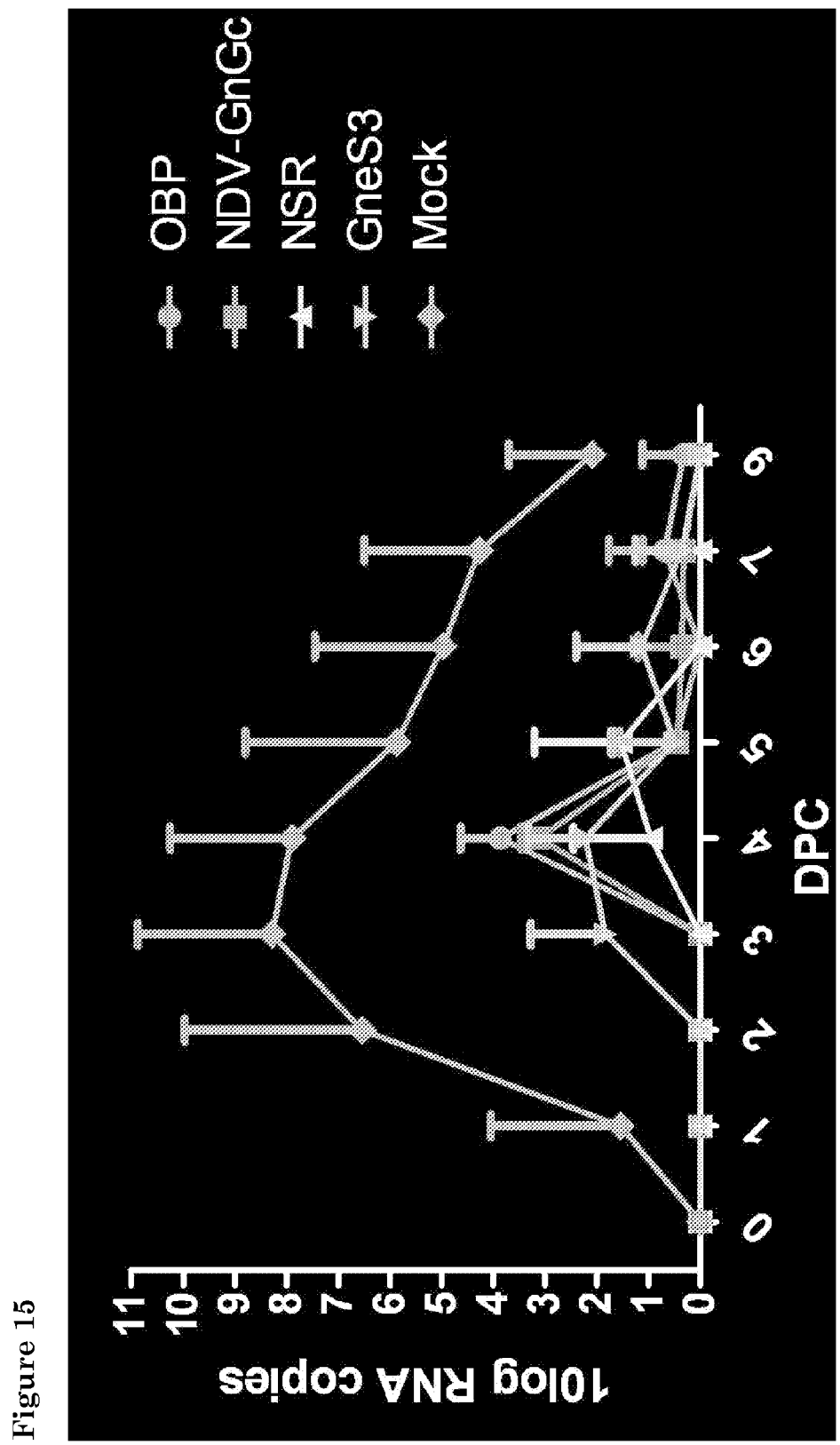

The occurrence of viremia was determined by qRRT-PCR on RNA isolated from plasma samples. High levels of viral RNA were detected in all but one of the unvaccinated control animals, peaking on DPC 3 (FIG. 15). Viral RNA levels were significantly lower in all vaccinated groups (p<0.0001).

Figure 16:
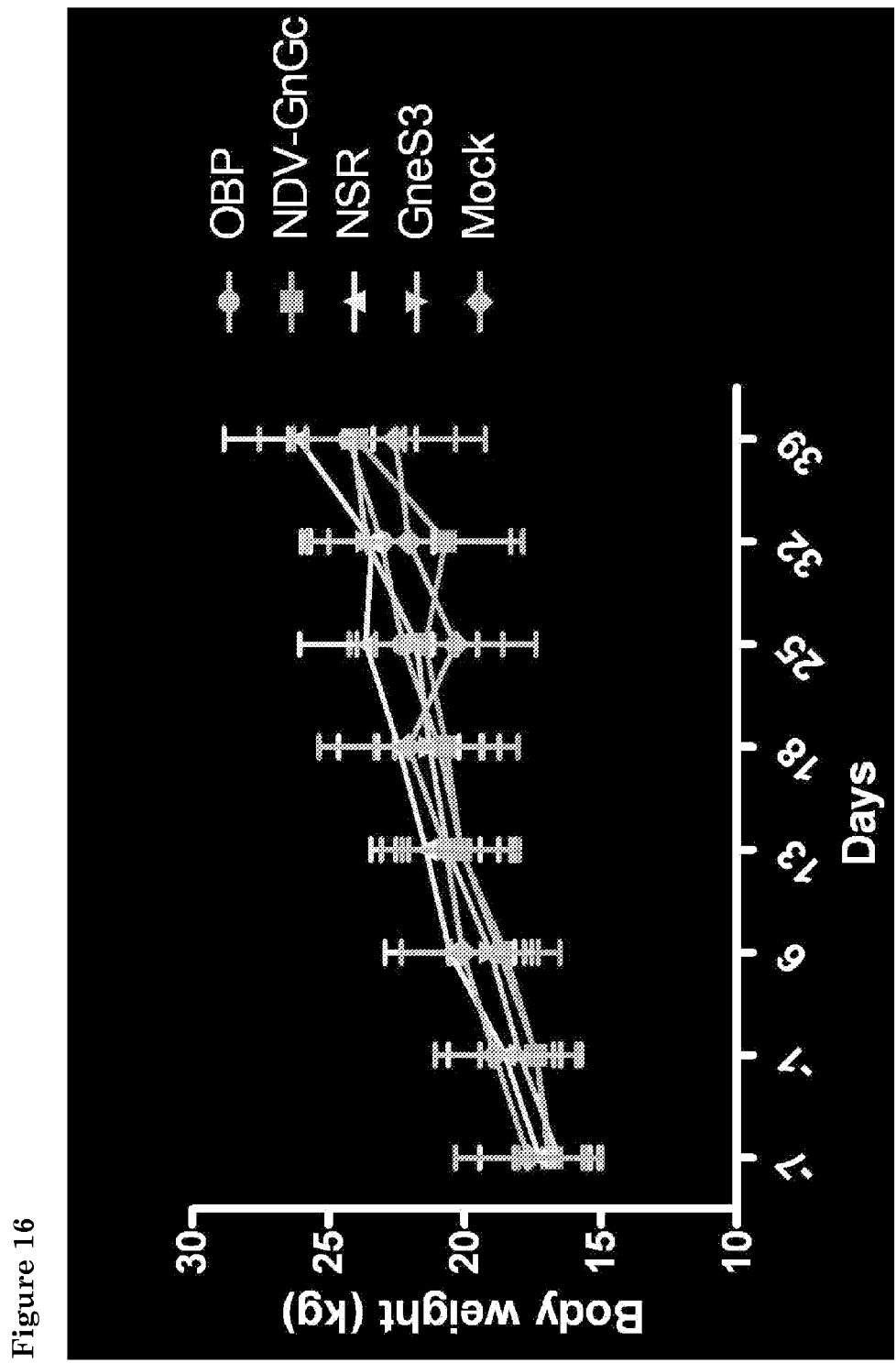

The body weights of the lambs were determined weekly. The lambs in the unvaccinated control group all displayed weight loss in the first two weeks after challenge (between days 18-25). Some weight loss, at a later time point (between days 25-32), was noted in five lambs vaccinated with NDV-GnGc and two lambs vaccinated with the NSR vaccine (FIG. 16). Differences between body weights were not statistically significant.

Figure 17:
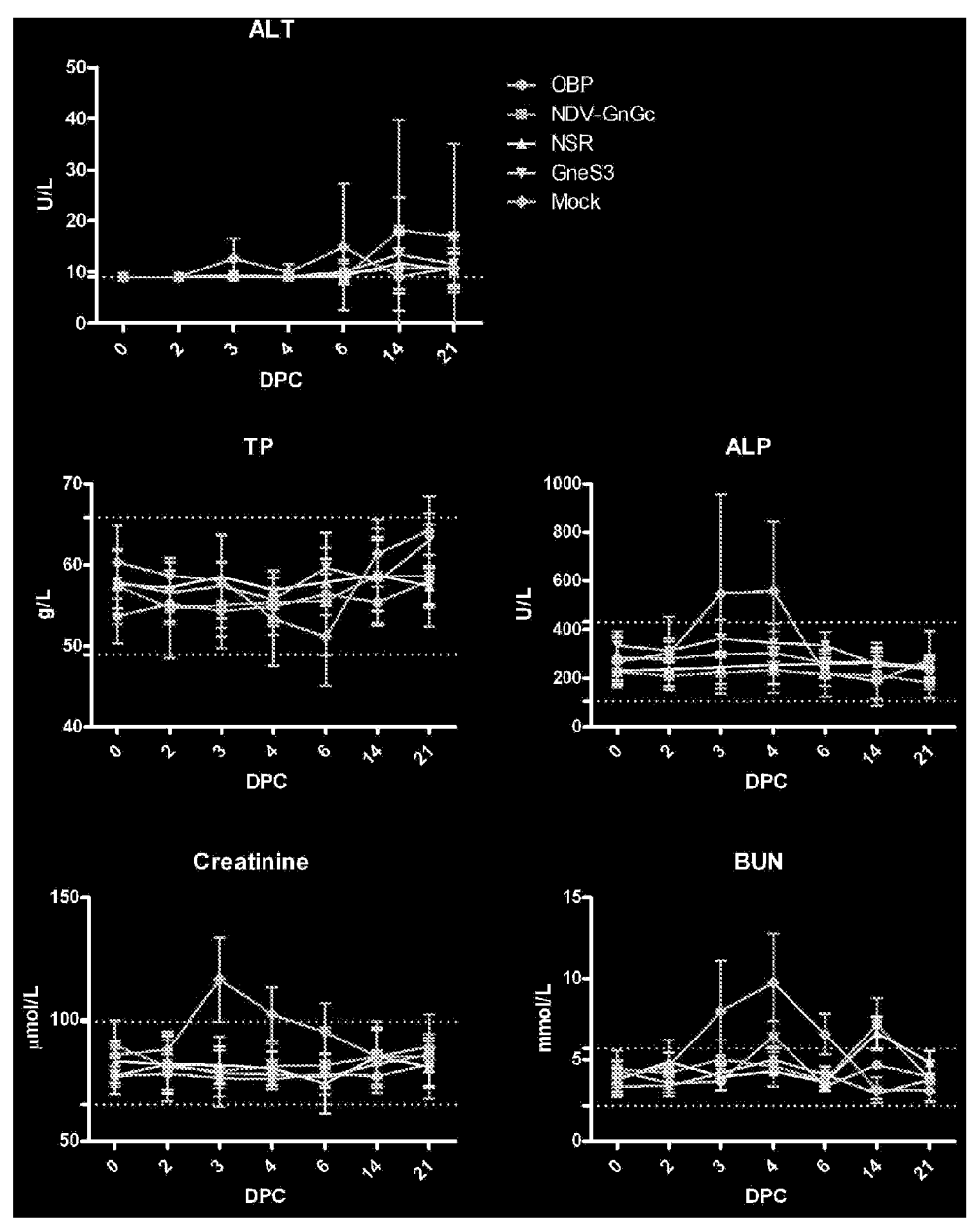

To investigate the occurrence of liver and renal damage, biochemical analyses were performed on serum samples using the Spotchem EZ dry chemistry analyzer. Hepatic dysfunction was assessed by sequential measurements of serum alkaline phosphatase (ALP), alanine transaminase (ALT) and total protein concentrations (TP) (FIG. 17). Total protein concentration is assumed to represent mostly albumin levels. In unvaccinated lambs, ALP and ALT levels were clearly increased when compared to vaccinated lambs. Statistical significance (p<0.05) was however only achieved when comparing ALP levels in plasma obtained from unvaccinated lambs (Mock) and NDV-GnGc-vaccinated lambs.

The concentrations of blood urea nitrogen (BUN) and creatinine were measured to assess renal function. BUN levels in serum obtained from unvaccinated lambs were clearly on average higher than levels detected in the serum of vaccinated lambs (FIG. 17).

Creatinine levels in serum from unvaccinated lambs were significantly higher when compared to levels detected in serum from vaccinated lambs (OBP vaccine, p<0.0005; GneS3, p<0.005; NSR, p<0.005; NDV-GnGc, p<0.05).

One lamb in the Mock-vaccinated control group succumbed to the infection. In this lamb, creatinine levels peaked on DPC 8 to a level of 582 μmol/l and BUN levels peaked to 30.6 mmol/l. This strongly suggests that this lamb died from severe kidney failure. Liver failure was revealed by a peak in ALT concentration of 20 U/l.

Conclusions

We here demonstrate that a single vaccination of sheep with the non-spreading NSR vaccine prevents mortality and morbidity and significantly reduces viremia, fever and clinical signs resulting from a RVFV challenge. The efficacy of the NSR vaccine did not significantly differ from the other vaccines evaluated in our study. The high immunogenicity of the NSR vaccine explains that the use of adjuvants is not required. The inability of the NSR vaccine to spread from the vaccinated animal provides optimal safety.

Example 11

RVFV Replicon Particles that Produce Recombinant Soluble Multimeric NA of Pandemic Swine-Origin 2009 A (H1N1) Influenza Virus Seq S-CD5-OS-GCN4-NA (see below) encodes a human codon-optimized soluble neuraminidase ectodomain (NA amino acids 75 to 469) of influenza virus A/California/04/2009 (H1N1). This sequence was synthesized at the GenScript Corporation. The NA gene is preceded by a sequence encoding an N-terminal CD5 signal peptide which is followed by sequences encoding a N-terminal OneSTrEP (OS) comprising a purification motif and a tetramerization motif (GCN4-pLI; Bosch et al. 2010. J. Virol. 84: 10366-10374).

To generate a vector comprising CD5-OS-GCN4-NA, pUC57-S-MCS was digested with NheI and XbaI and NheI/XbaI digested OS-GCN4-NA sequence was cloned into this plasmid, yielding pUC57-S-GCN4-NA. The CD5 sequence was subsequently introduced by annealing of the following oligo's:

Oligo CD5-3:
5'-CATGCCCATGGGGTCTCTGCAACCGCTGGCCACCTTGTACCTGCTGGGGATGCTGGTCGCTTCCGTG-3'

Oligo CD5-4:
5'-CTAGCACGGAAGCGACCAGCATCCCCAGCAGGTACAAGGTGGCCAGCGGTTGCAGAGACCCCATGGG-3'

The CD5 linker is ligated into NcoI/NheI-digested pUC57-S-GCN4-NA, yielding pUC57-S-CD5-OS-GCN4-NA.

BHK-GnGc cells were infected with FP-T7. After recovery, the cells were transfected with pUC57-L, pUC57-S-CD5-OS-GCN4-NA and pCAGGS-NSmGnGc, essentially as exemplified in Example 1. After cell passage, the transfection was repeated. This sequence of events was repeated until all the cells of the monolayer express the CD5-OS-GCN4-NA protein, as determined by IPMA. The quantity of GCN4-NA in the culture medium of these cells was determined. To establish high levels of NSmGnGc proteins, plasmid pCAGGS-NSmGnGc was again introduced in the cell line, yielding replicon particles containing the S-CD5-OS-GCN4-NA gene. The replicon particles are used for vaccination/challenge experiments in mice to establish the protective efficacy against a lethal H1N1 challenge.

Seq. S-CD5-OS-GCN4-NA
Nucleotides 1-69 (underlined) encode the CD5 sequence
Nucleotides 73-156 encodes the OneSTrEP(OS) peptide
Nucleotides 163-261 encodes the GCN4 domain
Nucleotides 262-1449 encodes the NA ectodomain

```
atgcccatggggtctctgcaaccgctggccacccttgtacctgctggggatgctggtcgct
 M  P  M  G  S  L  Q  P  L  A  T  L  Y  L  L  G  M  L  V  A tccgtgctagcgtggagccacccgcagttcgagaaaggtggaggttccggaggtggatcg
 S  V  L  A  W  S  H  P  Q  F  E  K  G  G  G  S  G  G  G  S ggaggtggatcgtggagccacccgcagttcgaaaaaagatctatgaaacaaatcgaagac
 G  G  G  S  W  S  H  P  Q  F  E  K  R  S  M  K  Q  I  E  D aagctggaagaaatcctttcgaaactgtaccacatcgaaaacgagctggccaggatcaag
 K  L  E  E  I  L  S  K  L  Y  H  I  E  N  E  L  A  R  I  K aaactgctgggcgaaggatccgctgctggacagtccgtcgtgagcgtgaagctggccgga
 K  L  L  G  E  G  S  A  A  G  Q  S  V  V  S  V  K  L  A  G aacagcagcctgtgcccagtgagcggatgggccatctacagcaaggacaacagcgtgcgc
 N  S  S  L  C  P  V  S  G  W  A  I  Y  S  K  D  N  S  V  R atcggcagcaagggcgacgtgttcgtgatccgcgagcccttcatcagctgcagcccctg
 I  G  S  K  G  D  V  F  V  I  R  E  P  F  I  S  C  S  P  L gagtgccgcaccttcttcctgacccagggcgccctgctgaacgacaagcacagcaacggc
 E  C  R  T  F  F  L  T  Q  G  A  L  L  N  D  K  H  S  N  G accattaaggaccgcagcccatacaggaccctgatgagctgccccattggagaggtgcca
 T  I  K  D  R  S  P  Y  R  T  L  M  S  C  P  I  G  E  V  P agcccatacaacagcaggtttgagagcgtggcttggtccgccagcgcttgccacgatgga
 S  P  Y  N  S  R  F  E  S  V  A  W  S  A  S  A  C  H  D  G atcaactggctgaccattggaatcagcggaccagacaacggcgccgtggccgtgctgaag
 I  N  W  L  T  I  G  I  S  G  P  D  N  G  A  V  A  V  L  K tacaacggcatcatcaccgacaccatcaagagctggcgcaacaacatcctgcgcacccag
 Y  N  G  I  I  T  D  T  I  K  S  W  R  N  N  I  L  R  T  Q gagagcgagtgcgcctgcgtgaacggcagctgcttcaccgtgatgaccgacggccccagc
 E  S  E  C  A  C  V  N  G  S  C  F  T  V  M  T  D  G  P  S aacggccaggccagctacaagatttccgcatcgagaagggcaagatcgtgaagagcgtg
 N  G  Q  A  S  Y  K  I  F  R  I  E  K  G  K  I  V  K  S  V gagatgaacgcccccaactaccactacgaggagtgcagctgctaccccgacagcagcgag
 E  M  N  A  P  N  Y  H  Y  E  E  C  S  C  Y  P  D  S  S  E atcacctgcgtgtgccgcgacaactggcacggcagcaaccgcccctgggtcagcttcaac
 I  T  C  V  C  R  D  N  W  H  G  S  N  R  P  W  V  S  F  N Cagaacctggagtaccagatcggctacatctgctccggaatctttggagacaatcccagg
 Q  N  L  E  Y  Q  I  G  Y  I  C  S  G  I  F  G  D  N  P  R ccaaatgacaagaccggcagctgcggaccagtgagcagcaatggagctaacggcgtgaag
 P  N  D  K  T  G  S  C  G  P  V  S  S  N  G  A  N  G  V  K ggcttcagcttcaagtacggcaacggcgtgtggatcggccgcaccaagagcatcagcagc
 G  F  S  F  K  Y  G  N  G  V  W  I  G  R  T  K  S  I  S  S cgcaacggcttcgagatgatctgggaccccaacggctggaccggcaccgacaacaacttc
 R  N  G  F  E  M  I  W  D  P  N  G  W  T  G  T  D  N  N  F agcatcaagcaggacatcgtgggcatcaacgagtggagcggatacagcggcagctttgtg
 S  I  K  Q  D  I  V  G  I  N  E  W  S  G  Y  S  G  S  F  V cagcacccagagctgaccggactggactgcatcaggccctgcttctgggtggagctgatc
 Q  H  P  E  L  T  G  L  D  C  I  R  P  C  F  W  V  E  L  I aggggaagacccaaggagaacaccatctggaccagcggcagcagcattagcttttgcgga
 R  G  R  P  K  E  N  T  I  W  T  S  G  S  S  I  S  F  C  G gtgaacagcgacaccgtgggatggagctggccagatggagctgagctgcccttcaccatc
 V  N  S  D  T  V  G  W  S  W  P  D  G  A  E  L  P  F  T  I gacaagtga
 D  K  -
```

Example 12

Expression of Foreign Proteins from the NSR Genome

Figure 18:
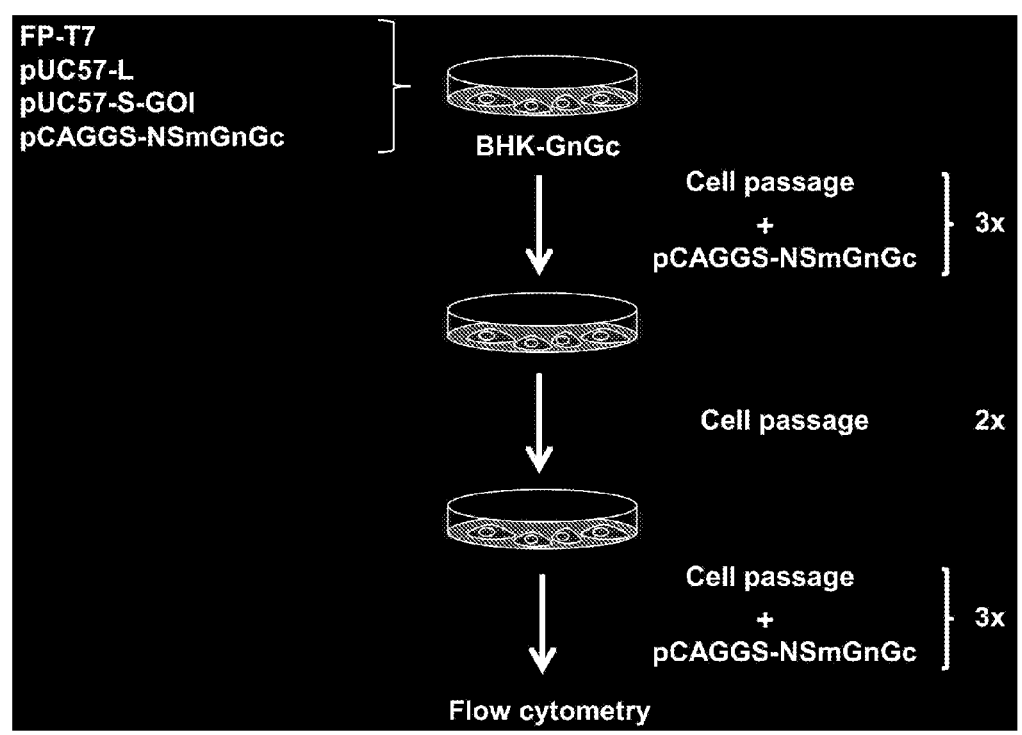

Replicon cell lines expressing trimeric soluble hemagglutinin protein (sHA$_3$) and tetrameric soluble neuraminidase protein (sNA$_4$) from influenza virus H1N1 were produced essentially as described in Example 5 with the modifications schematically depicted in FIG. 18. A replicon cell line expressing the eGFP protein was also produced alongside in these experiments.

Figure 19:
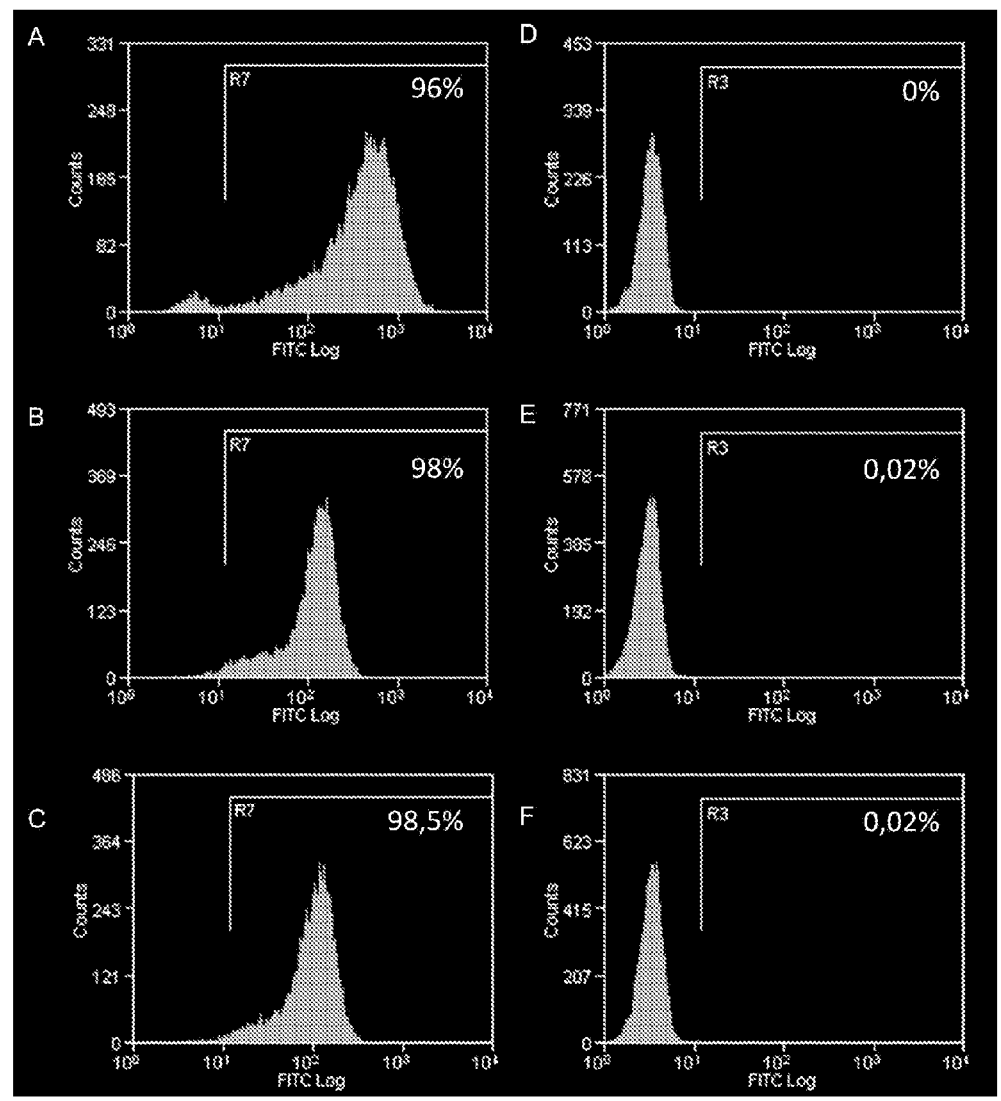

Flow cytometry analysis using an antibody specific for the N protein was used to determine the percentage of cells containing both the L and S(S-eGFP, S-$_s$HA$_3$ or S-$_s$NA$_4$) genome segments. N protein expression is dependent on the presence of both L and S genome segments. Flow cytometry demonstrated that 96% of the cells in which the L and S-eGFP genome segments were introduced were positive for N protein expression at passage 8 (FIG. 19A, results obtained from analysis of control BHK-GnGc cells are depicted in FIGS. 19D, E and F). Flow cytometry analysis of cells containing L and the S-CD5-HA-GCN4-ST (i.e. S-$_s$HA$_3$) segment demonstrated that 98% of the cells were positive for N expression (FIG. 19B). Flow cytometry analysis of cells containing L and the S-CD5-OS-GCN4-NA segment (i.e. S-$_s$NA$_4$) demonstrated that 98.5% of the cells were positive for N expression (FIG. 19C).

Production of the sHA$_3$ and sNA$_4$ Proteins by the Replicon Cell Lines

Figure 20:
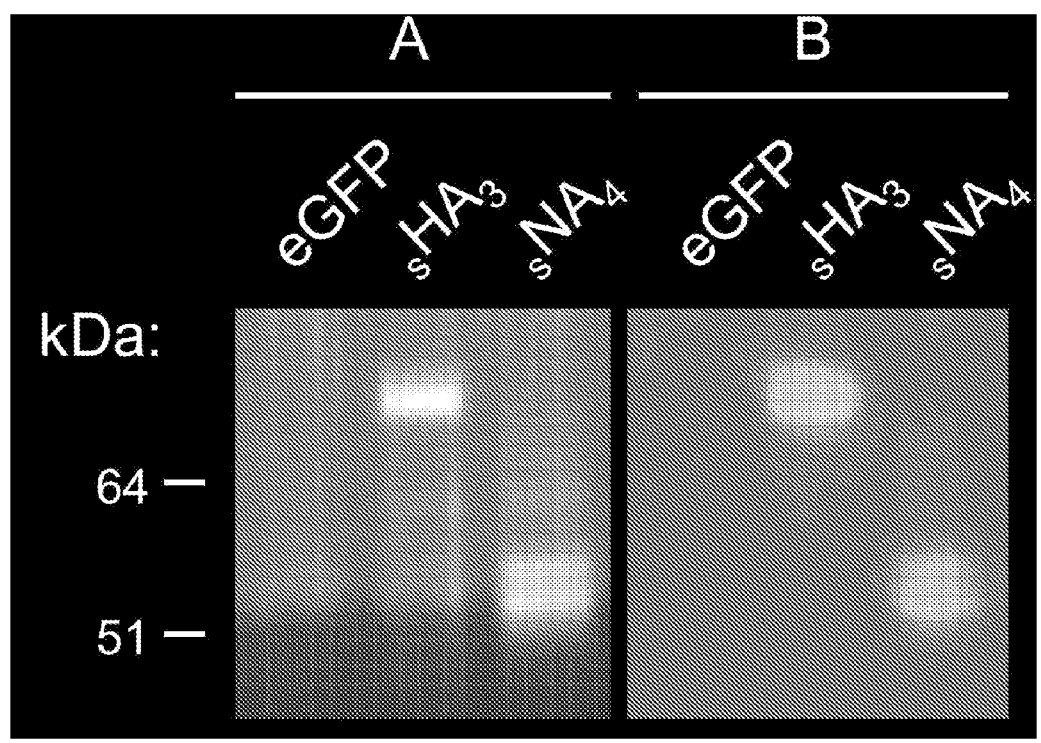

Cell culture medium was collected and pre-cleared by slow-speed centrifugation. Proteins were purified from the culture medium using Strep-Tactin Sepharose gravity-flow columns according to the instructions from the manufacturers (IBA, Göttingen, Germany). The eluted fractions were analyzed by Silver-stained polyacrylamide gels (FIG. 20A) and Western blot using Strep-Tactin conjugated to horseradish peroxidase (Strep-Tactin-HRP, IBA, FIG. 20B).

The yield of both proteins was estimated at 1 mg/l of culture medium (BCA assay, Pierce, Thermo Scientific, Landsmeer, The Netherlands). The production yields of the sHA$_3$ and sNA$_4$ proteins were again determined after cell passage 20 and found unchanged.

Transfection of the replicon cell lines with the pCAGGS-NSmGnGc plasmid resulted in NSR titers of $10^{7.3}$ TCID50/ml of NSR-$_s$HA$_3$ and $10^6$ TCID50/ml of NSR-$_s$NA$_4$. These particles will be used as vaccines for the control of influenza.

---

The invention claimed is:

1. A method for generating a recombinant, non-spreading bunyavirus replicon particle, the method comprising:
   A) culturing a eukaryotic cell with growth medium;
   B1) expressing T7 polymerase in the eukaryotic cell;
   B2) expressing bunyavirus Gn protein and bunyavirus Gc proteins, and optionally bunyavirus NSm protein, in the eukaryotic cell, wherein said Gn and Gc proteins may form a heterodimeric polyprotein (GnGc); and wherein upon the optional expression of NSm protein, a heterotrimeric polyprotein (NSmGnGc) may form;
   B3) transforming or transducing the eukaryotic cell with a vector comprising cDNA that encodes a bunyavirus L genome segment, wherein said L genome segment cDNA is flanked by a T7 promoter and cDNA of a ribozyme sequence;
   B4) transforming or transducing the eukaryotic cell with a vector comprising cDNA that encodes at least part of a bunyavirus S genome segment, wherein said S genome segment cDNA comprises at least the N-gene and the 3' and 5' UTRs, wherein said S genome segment cDNA is flanked by a T7 promoter and cDNA of a ribozyme sequence; and, optionally,
   B5) transforming or transducing the eukaryotic cell with a vector comprising cDNA that encodes a bunyavirus M genome segment from which the GnGc coding region has been functionally inactivated, wherein said M genome segment cDNA is flanked by a T7 promoter and cDNA of a ribozyme sequence;
   C) following steps B1-B5, the eukaryotic cell is maintained in the growth medium and recombinant, non-spreading bunyavirus replicon particles are generated and isolated from the growth medium;
   wherein the sequence of steps B1, B2, B3, B4, B5 is random and all or part of these steps may be performed simultaneously.

2. The method according to claim 1, wherein the T7 polymerase is provided to the eukaryotic cell by transfected the eukaryotic cell with a recombinant fowlpox virus expressing said T7 polymerase.

3. The method according to claim 1, wherein the eukaryotic cell is provided with the bunyavirus proteins of step B2) through transfection of the eukaryotic cell with a recombinant non-replicative and/or non-spreading paramyxovirus expressing said bunyavirus Gn, Gc, and/or NSm proteins.

4. The method according to claim 3, wherein the eukaryotic cell is stably transfected or wherein the recombinant non-replicative and/or non-spreading paramyxovirus is persistently present.

5. The method according to claim 1, wherein the eukaryotic cell is provided with the bunyavirus proteins of step B2)

through transfection of the eukaryotic cell with an expression vector conditionally expressing said bunyavirus Gn, Gc, and optionally NSm proteins.

6. The method according to claim 1, wherein the bunyavirus L genome segment and/or the S genome segment, and/or, when present, the M genome segment comprises a foreign gene.

7. The method according to claim 1, further comprising a M, L, or S minigenome, wherein a foreign gene is present in said M, L or S-minigenome.

8. The method according to claim 1, wherein the eukaryotic cell is a mammalian cell.

9. The method according to claim 1, wherein the bunyavirus is Rift Valley fever virus.

10. A recombinant, non-spreading bunyavirus replicon particle produced by the method according to claim 1.

11. The recombinant, non-spreading bunyavirus replicon particle according to claim 10, wherein the bunyavirus L genome segment and or the S genome segment and/or, when present, the M genome segment, comprises a foreign gene.

12. The recombinant, non-spreading bunyavirus replicon particle according claim 10, wherein the bunyavirus is Rift Valley fever virus.

13. A method for producing a bunyavirus replicon particle, the method comprising:
 A) culturing a eukaryotic cell with growth medium;
 B) transfecting, transforming, or transducing said eukaryotic cell with vectors expressing the bunyavirus NSm, Gn, and Gc proteins;
 C) transfecting the eukaryotic cell with the recombinant, non-spreading bunyavirus replicon particle according to claim 10.

14. A medicament or an immunogenic composition comprising the recombinant, non-spreading bunyavirus replicon particle according to claim 10.

15. method according to claim 8, wherein the mammalian cell is BHK-21.

16. The method according to claim 8, wherein the mammalian cell is BSR-T7/5.

* * * * *

SEQUENCE LISTING

```
<160> NUMBER OF SEQ ID NOS: 31

<210> SEQ ID NO 1
<211> LENGTH: 18
<212> TYPE: DNA
<213> ORGANISM: Artificial
<220> FEATURE:
<223> OTHER INFORMATION: T7 polymerase promoter sequence

<400> SEQUENCE: 1
taatacgact cactatag                                                 18

<210> SEQ ID NO 2
<211> LENGTH: 20
<212> TYPE: PRT
<213> ORGANISM: Artificial
<220> FEATURE:
<223> OTHER INFORMATION: Gc derived peptide

<400> SEQUENCE: 2

Val Phe Glu Arg Gly Ser Leu Pro Gln Thr Arg Asn Asp Lys Thr Phe
1               5                   10                  15

Ala Ala Ser Lys
            20

<210> SEQ ID NO 3
<211> LENGTH: 18
<212> TYPE: DNA
<213> ORGANISM: Artificial
<220> FEATURE:
<223> OTHER INFORMATION: T7 promoter

<400> SEQUENCE: 3
taatacgact cactatag                                                 18

<210> SEQ ID NO 4
<211> LENGTH: 19
<212> TYPE: DNA
<213> ORGANISM: Artificial
<220> FEATURE:
```

<223> OTHER INFORMATION: HDV ribozyme sequence

<400> SEQUENCE: 4
gggtcggcat ggcatctcc                                                    19

<210> SEQ ID NO 5
<211> LENGTH: 47
<212> TYPE: DNA
<213> ORGANISM: Artificial
<220> FEATURE:
<223> OTHER INFORMATION: T7 terminator sequence

<400> SEQUENCE: 5
tagcataacc ccttggggcc tctaaacggg tcttgagggg ttttttg                     47

<210> SEQ ID NO 6
<211> LENGTH: 38
<212> TYPE: DNA
<213> ORGANISM: Artificial
<220> FEATURE:
<223> OTHER INFORMATION: oligo MCS 1

<400> SEQUENCE: 6
catggactag tctcgaggct agcagatctg cggccgct                               38

<210> SEQ ID NO 7
<211> LENGTH: 38
<212> TYPE: DNA
<213> ORGANISM: Artificial
<220> FEATURE:
<223> OTHER INFORMATION: Oligo MCS 2

<400> SEQUENCE: 7
ctagagcggc cgcagatctg ctagcctcga gactagtc                               38

<210> SEQ ID NO 8
<211> LENGTH: 71
<212> TYPE: DNA
<213> ORGANISM: Artificial
<220> FEATURE:
<223> OTHER INFORMATION: oligo CD5-1

<400> SEQUENCE: 8
ctagtatgcc catgggtct ctgcaaccgc tggccacctt gtacctgctg gggatgctgg        60
tcgcttccgt g                                                            71

<210> SEQ ID NO 9
<211> LENGTH: 71
<212> TYPE: DNA
<213> ORGANISM: Artificial
<220> FEATURE:
<223> OTHER INFORMATION: Oligo CD5-2

<400> SEQUENCE: 9
ctagcacgga agcgaccagc atccccagca ggtacaaggt ggccagcggt tgcagagacc       60
ccatgggcat a                                                            71

<210> SEQ ID NO 10
<211> LENGTH: 1740
<212> TYPE: DNA
<213> ORGANISM: Artificial
<220> FEATURE:
<223> OTHER INFORMATION: CD5-HA-GCN4-ST
<220> FEATURE:
<221> NAME/KEY: CDS

<210> LOCATION: (1)..(1740)

<400> SEQUENCE: 10

```
atg ccc atg ggg tct ctg caa ccg ctg gcc acc ttg tac ctg ctg ggg      48
Met Pro Met Gly Ser Leu Gln Pro Leu Ala Thr Leu Tyr Leu Leu Gly
1               5                   10                  15 atg ctg gtc gct tcc gtg cta gca gac acc ctg tgc atc ggc tac cac      96
Met Leu Val Ala Ser Val Leu Ala Asp Thr Leu Cys Ile Gly Tyr His
            20                  25                  30 gcc aac aac agc acc gac acc gtg gac acc gtg ctg gag aag aac gtg     144
Ala Asn Asn Ser Thr Asp Thr Val Asp Thr Val Leu Glu Lys Asn Val
        35                  40                  45 acc gtg acc cac agc gtg aac ctg ctg gag gac aag cac aac ggc aag     192
Thr Val Thr His Ser Val Asn Leu Leu Glu Asp Lys His Asn Gly Lys
    50                  55                  60 ctg tgc aag ctg cgc ggc gtg gct cca ctg cac ctg ggc aag tgc aac     240
Leu Cys Lys Leu Arg Gly Val Ala Pro Leu His Leu Gly Lys Cys Asn
65                  70                  75                  80 att gct gga tgg atc ctg gga aac cca gag tgc gag agc ctg agc acc     288
Ile Ala Gly Trp Ile Leu Gly Asn Pro Glu Cys Glu Ser Leu Ser Thr
                85                  90                  95 gcc agc agc tgg agc tac atc gtg gag acc ccc agc agc gac aac ggc     336
Ala Ser Ser Trp Ser Tyr Ile Val Glu Thr Pro Ser Ser Asp Asn Gly
            100                 105                 110 acc tgc tac ccc ggc gac ttc atc gac tac gag gag ctg cgc gag cag     384
Thr Cys Tyr Pro Gly Asp Phe Ile Asp Tyr Glu Glu Leu Arg Glu Gln
        115                 120                 125 ctg agc agc gtg agc agc ttc gag cgc ttc gag atc ttc ccc aag acc     432
Leu Ser Ser Val Ser Ser Phe Glu Arg Phe Glu Ile Phe Pro Lys Thr
    130                 135                 140 agc agc tgg cca aac cac gac agc aac aag gga gtg acc gct gct tgc     480
Ser Ser Trp Pro Asn His Asp Ser Asn Lys Gly Val Thr Ala Ala Cys
145                 150                 155                 160 cca cac gct gga gcc aag agc ttc tac aag aac ctg atc tgg ctg gtg     528
Pro His Ala Gly Ala Lys Ser Phe Tyr Lys Asn Leu Ile Trp Leu Val
                165                 170                 175 aag aag ggc aac agc tac ccc aag ctg agc aag agc tac atc aac gac     576
Lys Lys Gly Asn Ser Tyr Pro Lys Leu Ser Lys Ser Tyr Ile Asn Asp
            180                 185                 190 aag ggc aag gag gtg ctg gtg ctg tgg ggc atc cac cac ccc agc acc     624
Lys Gly Lys Glu Val Leu Val Leu Trp Gly Ile His His Pro Ser Thr
        195                 200                 205 agc gcc gac cag cag agc ctg tac cag aac gcc gac acc tac gtg ttc     672
Ser Ala Asp Gln Gln Ser Leu Tyr Gln Asn Ala Asp Thr Tyr Val Phe
    210                 215                 220 gtg ggc agc agc cgc tac agc aag aag ttc aag ccc gag atc gcc atc     720
Val Gly Ser Ser Arg Tyr Ser Lys Lys Phe Lys Pro Glu Ile Ala Ile
225                 230                 235                 240 cgc ccc aag gtg cgc gac cag gag ggc cgc atg aac tac tac tgg acc     768
Arg Pro Lys Val Arg Asp Gln Glu Gly Arg Met Asn Tyr Tyr Trp Thr
                245                 250                 255 ctg gtg gag ccc ggc gac aag atc acc ttt gag gct acc gga aac ctg     816
Leu Val Glu Pro Gly Asp Lys Ile Thr Phe Glu Ala Thr Gly Asn Leu
            260                 265                 270 gtg gtg cca cgc tac gct ttt gct atg gag agg aat gct ggc agc ggc     864
Val Val Pro Arg Tyr Ala Phe Ala Met Glu Arg Asn Ala Gly Ser Gly
        275                 280                 285 atc atc atc agc gac acc ccc gtg cac gac tgc aac acc acc tgc cag     912
Ile Ile Ile Ser Asp Thr Pro Val His Asp Cys Asn Thr Thr Cys Gln
    290                 295                 300
```

| | | | | | | | | | | | | | | |
|---|---|---|---|---|---|---|---|---|---|---|---|---|---|---|
| acc | ccc | aag | ggc | gcc | atc | aac | acc | agc | ctg | ccc | ttc | cag | aac | atc | cac | 960 |
| Thr | Pro | Lys | Gly | Ala | Ile | Asn | Thr | Ser | Leu | Pro | Phe | Gln | Asn | Ile | His | |
| 305 | | | | 310 | | | | | 315 | | | | | 320 | | | ccc atc acc atc ggc aag tgc ccc aag tac gtg aag agc acc aag ctg    1008
Pro Ile Thr Ile Gly Lys Cys Pro Lys Tyr Val Lys Ser Thr Lys Leu
            325                 330                 335 cgc ctg gcc acc gga ctg agg aac atc cca agc atc cag agc cgc ggc    1056
Arg Leu Ala Thr Gly Leu Arg Asn Ile Pro Ser Ile Gln Ser Arg Gly
            340                 345                 350 ctg ttt gga gct att gct gga ttc att gag ggc ggc tgg acc gga atg    1104
Leu Phe Gly Ala Ile Ala Gly Phe Ile Glu Gly Gly Trp Thr Gly Met
        355                 360                 365 gtg gat gga tgg tac ggc tac cac cac cag aac gag cag ggc agc ggc    1152
Val Asp Gly Trp Tyr Gly Tyr His His Gln Asn Glu Gln Gly Ser Gly
    370                 375                 380 tac gcc gcc gac ctg aag agc acc cag aac gcc atc gac gag atc acc    1200
Tyr Ala Ala Asp Leu Lys Ser Thr Gln Asn Ala Ile Asp Glu Ile Thr
385                 390                 395                 400 aac aag gtg aac agc gtg atc gag aag atg aac acc cag ttc acc gcc    1248
Asn Lys Val Asn Ser Val Ile Glu Lys Met Asn Thr Gln Phe Thr Ala
                405                 410                 415 gtg ggc aag gag ttc aac cac ctg gag aag cgc atc gag aac ctg aac    1296
Val Gly Lys Glu Phe Asn His Leu Glu Lys Arg Ile Glu Asn Leu Asn
            420                 425                 430 aag aag gtg gac gac ggc ttc ctg gac atc tgg acc tac aac gcc gag    1344
Lys Lys Val Asp Asp Gly Phe Leu Asp Ile Trp Thr Tyr Asn Ala Glu
        435                 440                 445 ctg ctg gtg ctg ctg gag aac gag cgc acc ctg gac tac cac gac agc    1392
Leu Leu Val Leu Leu Glu Asn Glu Arg Thr Leu Asp Tyr His Asp Ser
    450                 455                 460 aac gtg aag aac ctg tac gag aag gtg cgc agc cag ctg aag aac aac    1440
Asn Val Lys Asn Leu Tyr Glu Lys Val Arg Ser Gln Leu Lys Asn Asn
465                 470                 475                 480 gcc aag gag atc ggc aac ggc tgc ttc gag ttc tac cac aag tgc gac    1488
Ala Lys Glu Ile Gly Asn Gly Cys Phe Glu Phe Tyr His Lys Cys Asp
                485                 490                 495 aac acc tgc atg gag agc gtg aag aac ggc acc tac gac tac ccc aag    1536
Asn Thr Cys Met Glu Ser Val Lys Asn Gly Thr Tyr Asp Tyr Pro Lys
            500                 505                 510 tac agc gag gag gcc aag ctg aac cgc gag gag atc gac ggc gtg aag    1584
Tyr Ser Glu Glu Ala Lys Leu Asn Arg Glu Glu Ile Asp Gly Val Lys
        515                 520                 525 ctc gag tta att aag cgc atg aag cag atc gag gac aag atc gaa gag    1632
Leu Glu Leu Ile Lys Arg Met Lys Gln Ile Glu Asp Lys Ile Glu Glu
    530                 535                 540 atc gag tcc aag cag aag aag atc gag aac gag atc gcc cgc atc aag    1680
Ile Glu Ser Lys Gln Lys Lys Ile Glu Asn Glu Ile Ala Arg Ile Lys
545                 550                 555                 560 aag att aag ctg gtg ccg cgc ggc agc ctc gag tgg agc cac ccg cag    1728
Lys Ile Lys Leu Val Pro Arg Gly Ser Leu Glu Trp Ser His Pro Gln
                565                 570                 575 ttc gag aag tga                                                     1740
Phe Glu Lys <210> SEQ ID NO 11
<211> LENGTH: 579
<212> TYPE: PRT
<213> ORGANISM: Artificial
<220> FEATURE:
<223> OTHER INFORMATION: Synthetic Construct

<400> SEQUENCE: 11

```
Met Pro Met Gly Ser Leu Gln Pro Leu Ala Thr Leu Tyr Leu Leu Gly
1               5                   10                  15

Met Leu Val Ala Ser Val Leu Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Thr Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
```

```
                    405                 410                 415
Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
            435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Leu Ile Lys Arg Met Lys Gln Ile Glu Asp Lys Ile Glu Glu
    530                 535                 540

Ile Glu Ser Lys Gln Lys Lys Ile Glu Asn Glu Ile Ala Arg Ile Lys
545                 550                 555                 560

Lys Ile Lys Leu Val Pro Arg Gly Ser Leu Glu Trp Ser His Pro Gln
                565                 570                 575

Phe Glu Lys

<210> SEQ ID NO 12
<211> LENGTH: 8
<212> TYPE: PRT
<213> ORGANISM: Artificial
<220> FEATURE:
<223> OTHER INFORMATION: combined FLAG/enterokinase cleavage site

<400> SEQUENCE: 12

Asp Tyr Lys Asp Asp Asp Asp Lys
1               5

<210> SEQ ID NO 13
<211> LENGTH: 8
<212> TYPE: PRT
<213> ORGANISM: Artificial
<220> FEATURE:
<223> OTHER INFORMATION: Strep tag

<400> SEQUENCE: 13

Trp Ser His Pro Gln Phe Glu Lys
1               5

<210> SEQ ID NO 14
<211> LENGTH: 12
<212> TYPE: PRT
<213> ORGANISM: Artificial
<220> FEATURE:
<223> OTHER INFORMATION: glycine linker

<400> SEQUENCE: 14

Gly Gly Gly Ser Gly Gly Gly Ser Gly Gly Gly Ser
1               5                   10

<210> SEQ ID NO 15
<211> LENGTH: 69
<212> TYPE: PRT
<213> ORGANISM: Artificial
<220> FEATURE:
```

-continued

<223> OTHER INFORMATION: part fusion protein

<400> SEQUENCE: 15

Tyr Gln Cys His Thr Asp Pro Thr Gly Asp Tyr Lys Asp Asp Asp Asp
1               5                   10                  15

Lys Ala Gly Pro Gly Trp Ser His Pro Gln Phe Glu Lys Gly Gly Gly
            20                  25                  30

Ser Gly Gly Gly Ser Gly Gly Gly Ser Trp Ser His Pro Gln Phe Glu
        35                  40                  45

Lys Gly Gly Gly Ser Gly Gly Gly Ser Gly Gly Gly Ser Trp Ser His
    50                  55                  60

Pro Gln Phe Glu Lys
65

<210> SEQ ID NO 16
<211> LENGTH: 67
<212> TYPE: DNA
<213> ORGANISM: Artificial
<220> FEATURE:
<223> OTHER INFORMATION: oligo CD5-3

<400> SEQUENCE: 16
catgcccatg ggtctctgc aaccgctggc caccttgtac ctgctgggga tgctggtcgc    60
ttccgtg                                                             67

<210> SEQ ID NO 17
<211> LENGTH: 67
<212> TYPE: DNA
<213> ORGANISM: Artificial
<220> FEATURE:
<223> OTHER INFORMATION: oligo CD5-4

<400> SEQUENCE: 17
ctagcacgga agcgaccagc atccccagca ggtacaaggt ggccagcggt tgcagagacc    60
ccatggg                                                             67

<210> SEQ ID NO 18
<211> LENGTH: 1449
<212> TYPE: DNA
<213> ORGANISM: Artificial
<220> FEATURE:
<223> OTHER INFORMATION: S-CD5-OS-GCN4-NA
<220> FEATURE:
<221> NAME/KEY: CDS
<222> LOCATION: (1)..(1449)

<400> SEQUENCE: 18 atg ccc atg ggg tct ctg caa ccg ctg gcc acc ttg tac ctg ctg ggg    48
Met Pro Met Gly Ser Leu Gln Pro Leu Ala Thr Leu Tyr Leu Leu Gly
1               5                   10                  15 atg ctg gtc gct tcc gtg cta gcg tgg agc cac ccg cag ttc gag aaa    96
Met Leu Val Ala Ser Val Leu Ala Trp Ser His Pro Gln Phe Glu Lys
            20                  25                  30 ggt gga ggt tcc gga ggt gga tcg gga ggt gga tcg tgg agc cac ccg    144
Gly Gly Gly Ser Gly Gly Gly Ser Gly Gly Gly Ser Trp Ser His Pro
        35                  40                  45 cag ttc gaa aaa aga tct atg aaa caa atc gaa gac aag ctg gaa gaa    192
Gln Phe Glu Lys Arg Ser Met Lys Gln Ile Glu Asp Lys Leu Glu Glu
    50                  55                  60 atc ctt tcg aaa ctg tac cac atc gaa aac gag ctg gcc agg atc aag    240
Ile Leu Ser Lys Leu Tyr His Ile Glu Asn Glu Leu Ala Arg Ile Lys
65                  70                  75                  80

```
aaa ctg ctg ggc gaa gga tcc gct gct gga cag tcc gtc gtg agc gtg    288
Lys Leu Leu Gly Glu Gly Ser Ala Ala Gly Gln Ser Val Val Ser Val
                85                  90                  95 aag ctg gcc gga aac agc agc ctg tgc cca gtg agc gga tgg gcc atc    336
Lys Leu Ala Gly Asn Ser Ser Leu Cys Pro Val Ser Gly Trp Ala Ile
            100                 105                 110 tac agc aag gac aac agc gtg cgc atc ggc agc aag ggc gac gtg ttc    384
Tyr Ser Lys Asp Asn Ser Val Arg Ile Gly Ser Lys Gly Asp Val Phe
        115                 120                 125 gtg atc cgc gag ccc ttc atc agc tgc agc ccc ctg gag tgc cgc acc    432
Val Ile Arg Glu Pro Phe Ile Ser Cys Ser Pro Leu Glu Cys Arg Thr
    130                 135                 140 ttc ttc ctg acc cag ggc gcc ctg ctg aac gac aag cac agc aac ggc    480
Phe Phe Leu Thr Gln Gly Ala Leu Leu Asn Asp Lys His Ser Asn Gly
145                 150                 155                 160 acc att aag gac cgc agc cca tac agg acc ctg atg agc tgc ccc att    528
Thr Ile Lys Asp Arg Ser Pro Tyr Arg Thr Leu Met Ser Cys Pro Ile
                165                 170                 175 gga gag gtg cca agc cca tac aac agc agg ttt gag agc gtg gct tgg    576
Gly Glu Val Pro Ser Pro Tyr Asn Ser Arg Phe Glu Ser Val Ala Trp
            180                 185                 190 tcc gcc agc gct tgc cac gat gga atc aac tgg ctg acc att gga atc    624
Ser Ala Ser Ala Cys His Asp Gly Ile Asn Trp Leu Thr Ile Gly Ile
        195                 200                 205 agc gga cca gac aac ggc gcc gtg gcc gtg ctg aag tac aac ggc atc    672
Ser Gly Pro Asp Asn Gly Ala Val Ala Val Leu Lys Tyr Asn Gly Ile
    210                 215                 220 atc acc gac acc atc aag agc tgg cgc aac aac atc ctg cgc acc cag    720
Ile Thr Asp Thr Ile Lys Ser Trp Arg Asn Asn Ile Leu Arg Thr Gln
225                 230                 235                 240 gag agc gag tgc gcc tgc gtg aac ggc agc tgc ttc acc gtg atg acc    768
Glu Ser Glu Cys Ala Cys Val Asn Gly Ser Cys Phe Thr Val Met Thr
                245                 250                 255 gac ggc ccc agc aac ggc cag gcc agc tac aag att ttc cgc atc gag    816
Asp Gly Pro Ser Asn Gly Gln Ala Ser Tyr Lys Ile Phe Arg Ile Glu
            260                 265                 270 aag ggc aag atc gtg aag agc gtg gag atg aac gcc ccc aac tac cac    864
Lys Gly Lys Ile Val Lys Ser Val Glu Met Asn Ala Pro Asn Tyr His
        275                 280                 285 tac gag gag tgc agc tgc tac ccc gac agc agc gag atc acc tgc gtg    912
Tyr Glu Glu Cys Ser Cys Tyr Pro Asp Ser Ser Glu Ile Thr Cys Val
    290                 295                 300 tgc cgc gac aac tgg cac ggc agc aac cgc ccc tgg gtc agc ttc aac    960
Cys Arg Asp Asn Trp His Gly Ser Asn Arg Pro Trp Val Ser Phe Asn
305                 310                 315                 320 cag aac ctg gag tac cag atc ggc tac atc tgc tcc gga atc ttt gga   1008
Gln Asn Leu Glu Tyr Gln Ile Gly Tyr Ile Cys Ser Gly Ile Phe Gly
                325                 330                 335 gac aat ccc agg cca aat gac aag acc ggc agc tgc gga cca gtg agc   1056
Asp Asn Pro Arg Pro Asn Asp Lys Thr Gly Ser Cys Gly Pro Val Ser
            340                 345                 350 agc aat gga gct aac ggc gtg aag ggc ttc agc ttc aag tac ggc aac   1104
Ser Asn Gly Ala Asn Gly Val Lys Gly Phe Ser Phe Lys Tyr Gly Asn
        355                 360                 365 ggc gtg tgg atc ggc cgc acc aag agc atc agc agc cgc aac ggc ttc   1152
Gly Val Trp Ile Gly Arg Thr Lys Ser Ile Ser Ser Arg Asn Gly Phe
    370                 375                 380 gag atg atc tgg gac ccc aac ggc tgg acc ggc acc gac aac aac ttc   1200
Glu Met Ile Trp Asp Pro Asn Gly Trp Thr Gly Thr Asp Asn Asn Phe
```

```
                    385                 390                 395                 400
agc atc aag cag gac atc gtg ggc atc aac gag tgg agc gga tac agc    1248
Ser Ile Lys Gln Asp Ile Val Gly Ile Asn Glu Trp Ser Gly Tyr Ser
            405                 410                 415 ggc agc ttt gtg cag cac cca gag ctg acc gga ctg gac tgc atc agg    1296
Gly Ser Phe Val Gln His Pro Glu Leu Thr Gly Leu Asp Cys Ile Arg
        420                 425                 430 ccc tgc ttc tgg gtg gag ctg atc agg gga aga ccc aag gag aac acc    1344
Pro Cys Phe Trp Val Glu Leu Ile Arg Gly Arg Pro Lys Glu Asn Thr
    435                 440                 445 atc tgg acc agc ggc agc agc att agc ttt tgc gga gtg aac agc gac    1392
Ile Trp Thr Ser Gly Ser Ser Ile Ser Phe Cys Gly Val Asn Ser Asp
450                 455                 460 acc gtg gga tgg agc tgg cca gat gga gct gag ctg ccc ttc acc atc    1440
Thr Val Gly Trp Ser Trp Pro Asp Gly Ala Glu Leu Pro Phe Thr Ile
465                 470                 475                 480 gac aag tga                                                        1449
Asp Lys

<210> SEQ ID NO 19
<211> LENGTH: 482
<212> TYPE: PRT
<213> ORGANISM: Artificial
<220> FEATURE:
<223> OTHER INFORMATION: Synthetic Construct

<400> SEQUENCE: 19

Met Pro Met Gly Ser Leu Gln Pro Leu Ala Thr Leu Tyr Leu Leu Gly
1               5                   10                  15

Met Leu Val Ala Ser Val Leu Ala Trp Ser His Pro Gln Phe Glu Lys
            20                  25                  30

Gly Gly Gly Ser Gly Gly Gly Ser Gly Gly Gly Ser Trp Ser His Pro
        35                  40                  45

Gln Phe Glu Lys Arg Ser Met Lys Gln Ile Glu Asp Lys Leu Glu Glu
    50                  55                  60

Ile Leu Ser Lys Leu Tyr His Ile Glu Asn Glu Leu Ala Arg Ile Lys
65                  70                  75                  80

Lys Leu Leu Gly Glu Gly Ser Ala Ala Gly Gln Ser Val Val Ser Val
                85                  90                  95

Lys Leu Ala Gly Asn Ser Ser Leu Cys Pro Val Ser Gly Trp Ala Ile
            100                 105                 110

Tyr Ser Lys Asp Asn Ser Val Arg Ile Gly Ser Lys Gly Asp Val Phe
        115                 120                 125

Val Ile Arg Glu Pro Phe Ile Ser Cys Ser Pro Leu Glu Cys Arg Thr
    130                 135                 140

Phe Phe Leu Thr Gln Gly Ala Leu Leu Asn Asp Lys His Ser Asn Gly
145                 150                 155                 160

Thr Ile Lys Asp Arg Ser Pro Tyr Arg Thr Leu Met Ser Cys Pro Ile
                165                 170                 175

Gly Glu Val Pro Ser Pro Tyr Asn Ser Arg Phe Glu Ser Val Ala Trp
            180                 185                 190

Ser Ala Ser Ala Cys His Asp Gly Ile Asn Trp Leu Thr Ile Gly Ile
        195                 200                 205

Ser Gly Pro Asp Asn Gly Ala Val Ala Val Leu Lys Tyr Asn Gly Ile
    210                 215                 220

Ile Thr Asp Thr Ile Lys Ser Trp Arg Asn Asn Ile Leu Arg Thr Gln
225                 230                 235                 240
```

Glu Ser Glu Cys Ala Cys Val Asn Gly Ser Cys Phe Thr Val Met Thr
                245                 250                 255

Asp Gly Pro Ser Asn Gly Gln Ala Ser Tyr Lys Ile Phe Arg Ile Glu
            260                 265                 270

Lys Gly Lys Ile Val Lys Ser Val Glu Met Asn Ala Pro Asn Tyr His
        275                 280                 285

Tyr Glu Glu Cys Ser Cys Tyr Pro Asp Ser Ser Glu Ile Thr Cys Val
    290                 295                 300

Cys Arg Asp Asn Trp His Gly Ser Asn Arg Pro Trp Val Ser Phe Asn
305                 310                 315                 320

Gln Asn Leu Glu Tyr Gln Ile Gly Tyr Ile Cys Ser Gly Ile Phe Gly
                325                 330                 335

Asp Asn Pro Arg Pro Asn Asp Lys Thr Gly Ser Cys Gly Pro Val Ser
            340                 345                 350

Ser Asn Gly Ala Asn Gly Val Lys Gly Phe Ser Phe Lys Tyr Gly Asn
        355                 360                 365

Gly Val Trp Ile Gly Arg Thr Lys Ser Ile Ser Ser Arg Asn Gly Phe
    370                 375                 380

Glu Met Ile Trp Asp Pro Asn Gly Trp Thr Gly Thr Asp Asn Asn Phe
385                 390                 395                 400

Ser Ile Lys Gln Asp Ile Val Gly Ile Asn Glu Trp Ser Gly Tyr Ser
                405                 410                 415

Gly Ser Phe Val Gln His Pro Glu Leu Thr Gly Leu Asp Cys Ile Arg
            420                 425                 430

Pro Cys Phe Trp Val Glu Leu Ile Arg Gly Arg Pro Lys Glu Asn Thr
        435                 440                 445

Ile Trp Thr Ser Gly Ser Ser Ile Ser Phe Cys Gly Val Asn Ser Asp
    450                 455                 460

Thr Val Gly Trp Ser Trp Pro Asp Gly Ala Glu Leu Pro Phe Thr Ile
465                 470                 475                 480

Asp Lys

<210> SEQ ID NO 20
<211> LENGTH: 6814
<212> TYPE: DNA
<213> ORGANISM: Artificial
<220> FEATURE:
<223> OTHER INFORMATION: Partial sequence pUS57-L

<400> SEQUENCE: 20
ttcgagctcg gtaccagcgg aagagcgccc aatacgcaaa ccgcctctcc ccgcgcgttg      60
gccgattcat taatgcaggg ggatctcgat cccgcgaaat taatacgact cactataqac     120 acaaaggcgc ccaatcatgg attctatatt atcaaaacag ctggttgaca agactggttt     180
tgttagagtg ccaatcaagc attatgactg tacaatgcta actctggcac tcccaacatt     240
tgatgtctcc aagatggtag atagaattac catgacttc aatttagacg acatacaagg      300
agcatctgaa ataggctcaa ctttgctacc ctctatgtcg atagatgtgg aagtatggc      360 caatttgtt cacgatttca cctttggcca cttagctgac aagactgaca gactcttaat      420
gcgtgagttt cccatgatga atgacgggtt tgatcatctg agccctgaca tgattatcaa     480
aactacatct ggcatgtata acatcgttga gttcaccacc tttagggggg atgaaagagg     540
tgcattccag gctgccatga ctaaactcgc taagtatgag gttccttgtg agaacagatc     600
tcagggcagg actgttgttc tttatgttgt tagcgcctac cggcatggtg tttggtctaa     660

```
tttggagcta gaggactctg aagcagagga gatggtatat aggtacagac ttgcccttag    720
tgtgatggat gagctaagga ccttgttccc agaactgtca tccacagatg aggaactagg    780
aaagactgag agagagttgc tagccatggt ctcctccatc caaataaatt ggtcagtcac    840
agaatctgtg tttcctccct ttagcagaga aatgtttgac aggttcagat cttctcctcc    900
cgattcagag tacatcacga ggatagtgag cagatgcctc ataaattctc aagagaaact    960
catcaataat tccttctttg ctgaagggaa tgataaagtt ttgagatttt caaaaaacgc   1020
tgaggagtgt tccttggcaa tagagagagc tttaaatcag tatagggcag aagacaacct   1080
tagggaccta aatgaccaca agtctactat tcagctgcct ccctggctgt cctatcacga   1140
tgccgatggc aaagatctgt gccctcttca gggattagat gtgagaggag accatcccat   1200
gtgcaacctg tggagagaag tggttacctc tgcaaatcta gaggagattg agaggatgca   1260
cgatgatgca gcggcagaac ttgagtttgc cctttcaggg gtgaaggaca ggccagatga   1320
aagaaacaga taccatagag tccatctgaa tatggactca gatgatagtg tctacatagc   1380
tgctttaggg gttaatggaa agaagcataa agcagacaca ttagtgcaac aaatgagaga   1440
caggagcaaa cagcccttct ctccagatca tgatgtggat cacatatctg aatttctctc   1500
tgcatgctct agtgacttgt gggcaacaga tgaggaccta caaccctc tctcttgtga   1560 taaagagctt agattggcag ctcagagaat tcatcagcca tccttatcag aaaggggctt   1620
caatgagatt ataacagagc actacagatt tatgggaagt aggataggat catggtgcca   1680
aatggtcagt ttaataggag ctgagctatc agcttctgta aagcaacatg ttaagcctaa   1740
ctattttgtg attaaacgac tactaggttc tgggattttc ttgctgatca agcctacttc   1800
cagcaaaagc catatattcg tgtcttttgc aattaagcgc tcttgctggg cctttgatct   1860
ctccacttcc agggttttca aaccctacat agatgccggg gatctgttag ttactgactt   1920
tgtttcttac aaactaagta agcttaccaa ccctctgcaag tgcgtttcgt taatggaatc   1980
ctccttctca ttttgggcag aggcatttgg gattccaagc tggaactttg ttagtgactt   2040
gttcaggtct tcagactctg cagcaatgga tgcctcatac atgggcaaac tctctttatt   2100
aacccttttg gaagacaaag caacaactga agagttacag actattgcaa gatatataat   2160
catggagggc tttgtctcgc ccccagaaat cccaaaacct cacaagatga cctctaagtt   2220
tcccaaggtt ctcaggtcag agctgcaggt ttacttatta aactgcttat gcagaactat   2280
ccagagaata gcaggtgagc ctttattct taagaagaag gatgggtcta tatcctgggg   2340
tggcatgttt aatccttttt cagggcgtcc actgcttgat atgcaaccac tcatcagctg   2400
ttgttacaat ggttacttta aaacaaaga agaagagact gagccttcct cccttctgg   2460 gatgtataag aaaattatag aacttgagca ccttagacca cagtcagatg ccttcttggg   2520
ttataaagat ccagaactac ctagaatgca tgagttcagt gtttcctact tgaaggaggc   2580
ttgcaatcat gctaagctgg tcttaaggag tctctatgga cagaatttca tggagcaaat   2640
agacaaccaa attattcgag agctcagtgg gttgactcta gaaagattag ccacacttaa   2700
ggccacaagc aactttaatg agaattggta tgtctataag gatgtggcag acaagaacta   2760
cacaagggat aaattattag tgaagatgtc aaaatatgct tctgagggaa agagcctagc   2820
tatccagaag tttgaggatt gcatgaggca gatagagtca caaggatgta tgcacatttg   2880
tttgtttaag aaacaacagc atggaggtct gagagagatc tatgtgatgg gtgcagagga   2940
aagaattgtt caatcggtgg tggagacaat agccaggtct ataggggaagt tctttgcttc   3000
```

```
tgatacccctc tgtaacccccc ccaataaggt gaaaattcct gagacacatg gcattagggc    3060
tcggaagcaa tgtaaggggc ctgtgtggac ttgtgcaaca tcagatgatg caaggaagtg    3120
gaaccaaggc cattttgtta caaagtttgc cctcatgcta tgtgagttca cctctcctaa    3180
gtggtggcca ttgatcatta ggggatgttc aatgtttacc aggaaaagga tgatgatgaa    3240
tttgaattat cttaagatcc tggatggtca tcgagagctt gatattagag atgactttgt    3300
gatggatctc ttcaaagctt atcatggtga ggcagaagtt ccatgggctt ttaagggtaa    3360
aacatatctg gaaaccacga cagggatgat gcagggata ttgcattata cttcctcatt    3420
attacacacc attcatcaag aatacatccg gtccttgtcc tttaaaatat tcaacctgaa    3480
ggttgctcct gagatgagca aaagcctggt ttgtgacatg atgcaaggat cagatgatag    3540
tagcatgcta atcagcttcc cagctgatga cgagaaggtt ctcaccagat gcaaagtggc    3600
cgcagccata tgcttccgaa tgaagaagga gctgggagtg taccttgcca tctacccctc    3660
agagaagtcc acagcaaaca cagattttgt gatggagtac aattctgaat tttatttcca    3720
cacccagcat gttagaccga cgatcaggtg gattgcagca tgttgcagcc tgccagaagt    3780
ggaaacacta gtagcccgcc aggaagaggc ctctaatcta atgacttcag ttactgaggg    3840
gggtgggtca ttctccttag ctgcaatgat tcagcaagct cagtgcactc tccattacat    3900
gctaatgggc atgggagtgt ctgagctatt cttagagtat aagaaggcag tgctgaagtg    3960 gaatgacccct ggtctgggtt tcttcctgct tgacaatcct tatgcgtgcg ggtttgggagg    4020 ttttagattt aatctcttca aagccatcac cagaactgat ttgcagaagc tatatgcttt    4080
cttcatgaag aaggttaagg gctcagctgc tagggactgg gcagatgagg atgttaccat    4140
cccagaaacg tgtagcgtga gcccaggtgg cgctctaatt cttagctcct ctctaaagtg    4200
gggatctagg aagaagtttc agaaactgag agaccgtttg aacataccag agaactggat    4260
tgagctaata aatgagaatc cagaggtgct ctatcgagct cccagaacag gcccagaaat    4320
attgttgcgc attgcagaga aagtccatag ccctggtgtt gtgtcatcat tgtcttctgg    4380
caatgcagtc tgtaaagtca tggcctcagc tgtatacttc ttatcagcaa caattttttga    4440 agacactgga cgccctgagt tcaacttctt agaggattcc aagtacagct tgctacaaaa    4500
gatggccgca tattctggct ttcatggttt caatgatatg gagccagaag atatattatt    4560
cctattcccg aacattgagg aattagaatc actggattct atagtttaca caagggaga    4620 aatagacatc atcccaagag ttaatatcag ggatgcaacc caaaccaggg tcactatctt    4680
taatgagcag aagaccctcc gaacatctcc agagaagttg gtgtcagaca gtggttcgg    4740 gactcagaag agtaggatag gcaaaacaac tttcctggct gaatgggaga agctaaagaa    4800
aattgtgaag tggttggaag acactccaga agcaactcta gctcacactc cactgaataa    4860
ccatattcag gttaggaatt ctttgctag aatggaaagc aagcctagaa cggttagaat    4920
aacaggagct cctgtaaaga gaggtcagg ggttagcaag atagctatgg ttatccgtga    4980
caatttctcc cggatggcc atcttagagg tgtagagac ctcgctggct tcactcgtag    5040
tgtgtcagct gaaatcctca agcactttct gttctgcata ctacagggtc catacagtga    5100
gagctataag ctacagctaa tctacagagt cctaagctca gtgtcaaacg ttgagataaa    5160
ggaatcggat ggtaagacaa aaaccaattt gattgggatc cttcagagat ttctagatgg    5220
tgatcacgtt gtccctataa ttgaagagat gggagccgga acagtgggtg gattcatcaa    5280
gagacaacag tctaaggttg tgcaaaataa agtggtctat tatggagttg ggatctggag    5340
aggcttcatg gatggatatc aggtccatct tgagatagaa aatgacatag gacagccccc    5400
```

| | |
|---|---|
| aaggcttagg aatgtcacaa ctaactgtca gagcagccca tgggatctga gtgtcccaat | 5460 |
| aaggcagtgg gcagaagaca tgggggtcac aaacaaccag gattattcct ctaaatctag | 5520 |
| cagaggagct agatattgga tgcattcatt taggatgcaa ggacccagca agccatttgg | 5580 |
| atgcccagtt tatattatta agggtgacat gtcagatgtt atcagactga aaaagagga | 5640 |
| ggtggagatg aaagtacggg gctctactct caacttgtac actaagcacc attctcatca | 5700 |
| agacttacac attttatctt acactgcatc agacaatgat ctcagtccag gcattttcaa | 5760 |
| gtcaatatca gatgagggag tagctcaagc cctgcagtta tttgagaggg agccaagcaa | 5820 |
| ctgctgggtg agatgtgagt ctgtagctcc aaaattcata tcagccatcc ttgagatatg | 5880 |
| tgagggaag agacagataa aaggaatcaa cagaaccaga ctctcagaga ttgtgagaat | 5940 |
| ttgttctgaa tcttccctaa gatcaaaggt cggatctatg ttctcatttg tcgccaatgt | 6000 |
| tgaggaggcc catgatgttg attatgatgc gttaatggat ctaatgatag aagatgctaa | 6060 |
| gaacaatgca ttcagtcatg ttgtcgattg catagagttg gatgttaatg gtccttacga | 6120 |
| gatggagtct tttgatacat ctgatgtcaa cctctttggg ccagcccatt acaaggacat | 6180 |
| cagttcatta tctatgattg ctcatcccct aatggataag tttgttgatt atgccatttc | 6240 |
| caagatgggg agagcctcag ttagaaaagt tctagagaca ggtcggtgct ctagcaaaga | 6300 |
| ctatgattta tcaaaggttc tcttcagaac tctacagaga ccagaagaga gcattaggat | 6360 |
| agatgatctg gagttatatg aggagacaga tgtggcggat gacatgctag gctaagacca | 6420 |
| ataagcaaag tcaggcttag atttagggat actacgctag tattggaatc catgtgggtt | 6480 |
| ctgatactag catagtgcta caatattggg cggtctttgt gtgggtcggc atggcatctc | 6540 |
| cacctcctcg cggtccgacc tgggcatccg aaggaggacg tcgtccactc ggatggctaa | 6600 |
| gggagagctc ggatccggct gctaacaaag cccgaaagga agctgagttg gctgctgcca | 6660 |
| ccgctgagca ataactagca taaccccttg gggcctctaa acgggtcttg aggggttttt | 6720 |
| tgctgaaagg aggaactata tccggatcga gatcctctag ccagatcctc tacgccggac | 6780 |
| gcatcgtggc cggcgtcgac aagcttggcg taat | 6814 |

<210> SEQ ID NO 21
<211> LENGTH: 4281
<212> TYPE: DNA
<213> ORGANISM: Artificial
<220> FEATURE:
<223> OTHER INFORMATION: Partial sequence pUC57-M

<400> SEQUENCE: 21

| | |
|---|---|
| gaattcagcg gaagagcgcc caatacgcaa accgcctctc cccgcgcgtt ggccgattca | 60 |
| ttaatgcagg gggatctcga tcccgcgaaa ttaatacgac tcactataga cacaaagacg | 120 |
| gtgcattaaa tgtatgtttt actaacaatt ctgatcacgg ttctggtgtg tgaggcggtt | 180 |
| attagagtgt ctctaagttc cacaagagaa gagacctgct tggtgactac caccaaccca | 240 |
| gagatgattg aaggagcttg ggattcactc agagaggagg agatgccaga ggagctctcc | 300 |
| tgttccatat caggcataag ggaggtcaaa acctcaagcc aggaattgta tagggcatta | 360 |
| aaagccatca ttgctgctga tggcttgaac aacatcacct gccatggtaa ggatcctgag | 420 |
| gataagattt ctctcgtaaa gggtcctcct cacaaaaagc gggtggggat agttcggtgt | 480 |
| gagagacgaa gagacgctaa gcaaatagga agagaaacca tggcagggat tgcaatgaca | 540 |
| gtccttccag ccttagcagt ttttgctttg gcacctgttg ttttttgctga agaccctcat | 600 |

```
ctcagaaaca gaccagggaa ggggcacaac tacattgacg ggatgactca ggaggacgcc      660
acatgcaaac ctgtgacata tgctggggct tgtagcagtt ttgatgtctt gctcgaaaag      720
ggaaaattcc ccctcttcca gtcgtatgcc catcacagaa ccctactaga agcagttcac      780
gacaccatca ttgcaaaggc tgatccacct agctgtgacc ttcagagtgc tcatgggaat      840
ccctgcatga aggagaaact cgtgatgaag acacactgtc caaatgacta ccagtcagct      900
cattacctca caatgacgg gaaaatggct tcagtcaagt gccctcctaa atatgagctc       960
actgaggact gcaattttg caggcagatg acaggtgcta gcttgaagaa ggggtcttat      1020
cctcttcagg acttatttg tcagtcaagt gaggatgatg gatcaaaatt aaaaacaaaa      1080
atgaaagggg tctgcgaagt gggggttcaa gcactcaaaa agtgtgatgg ccaactcagc      1140
actgcacatg aggttgtgcc ctttgcagta tttaagaact caagaaggt ttatcttgat       1200 aagcttgacc tcaagactga ggaaaatctg ttgccagact catttgtctg cttcgagcat      1260
aagggacagt ataaaggaac aatggactct ggtcagacca agaggagct caaaagcttt       1320 gatatctctc agtgccccaa gattggagga catggtagca agaagtgcac tggggacgca      1380 gcttttgct ctgcttatga gtgcactgct caatacgcca atgcttattg ttcacatgct       1440
aatgggtcag agttgtaca gatacaagta tccggggtct ggaagaagcc tttgtgtgtc       1500
gggtatgaga gggtggttgt gaagagagaa ctctctgcta agcccatcca gagagttgag      1560
ccttgcacaa cttgtataac caaatgtgag cctcacggat tggttgtccg atcaacaggt      1620
ttcaagatat catctgcagt tgcttgtgct agcggagttt gcgttacagg atcgcagagc      1680
ccttctaccg agattacact caagtatcca gggatatccc agtcctctgg gggggacata      1740
ggggttcaca tggcacatga tgatcagtca gttagctcca aaatagtagc tcactgccct      1800
ccccaggatc catgcctagt gcatggctgc atagtgtgtg ctcatggcct gataaattac      1860
cagtgtcaca ctgctctcag tgcctttgtt gttgtgttcg tatttagctc tgtcgcaata      1920
atttgtttgg ccattcttta taaagttctc aagtgcctaa agattgcccc aaggaaagtt      1980
ctggatccac taatgtggat tactgttttc atcagatggg tgtataagaa gatggttgcc      2040
agagtagcag acaatatcaa tcaggtgaac agggaaatag gatggatgga aggaggccag      2100
ctggctctag ggaaccctgc ccctattcct cgtcatgctc caattccacg ttatagcaca      2160
tacctaatgc tactattgat tgtctcatat gcatcagcat gttcagaact gattcaggca      2220
agctccagaa tcaccacttg ctccacagaa ggtgtcaaca ccaagtgtag gctgtctggc      2280
acagcattaa tcagggcagg gtcagttggg gcagaggctt gtttgatgtt aaaggggtc       2340 aaggaagacc aaaccaagtt tttgaagata aaaactgtct caagtgagct atcgtgcagg      2400
gagggccaga gctattggac tgggtccttt agccctaaat gtctgagctc aaggagatgc      2460
catcttgtcg gggaatgtca tgtgaatagg tgtctgtctt ggagagacaa tgaaacctca      2520
gcagaatttt catttgttgg ggaaagcacg accatgcggg agaacaagtg ttttgagcag      2580
tgtggaggat ggggatgtgg gtgtttcaat gtgaacccat cttgcttatt tgtgcacacg      2640
tatctgcagt cagtcagaaa agaggccctt agagttttca actgtatcga ttgggtgcat      2700
aaactcactc tagagattac tgactttgat ggctctgttt caacaataga cctgggagca      2760
tcatctagcc gtttcacaaa ctggggttca gttagcctct cactgacgc agagggcatt       2820 tcaggctcaa acagcttttc cttcattgag agcccaggca aagggtatgc aattgttgat      2880
gagccattct cagaaattcc tcggcaaggg ttcttggggg agatcaggtg caattcagaa      2940
tcttcagtcc tgagtgctca tgaatcatgc cttagggcac caaatcttat ttcatacaag      3000
```

```
cccatgatag atcagttgga gtgcacaaca aatctgattg atcccttttgt tgtctttgag    3060 aggggctctc tgccacagac aaggaatgac aaaacctttg cagcttcaaa aggaaatagg    3120
ggtgttcaag ctttctctaa gggctctgta caggctgatc taacactgat gtttgacaat    3180
tttgaggtgg actttgtggg agcagccgtg tcttgtgatg ccgccttctt aaatttgaca    3240
ggttgctatt cctgcaatgc aggggccaga gtctgcctgt ctatcacatc cacaggaact    3300
ggaactctct ctgcccacaa taaagatgga tctctgcata tagttcttcc atcagagaat    3360
ggaacaaaag atcagtgtca gatactacac ttcactgtac ctgaggtaga ggaggagttt    3420
atgtactctt gtgatggaga tgagcggcct ctgttggtga agggaaccct gatagctatt    3480
gatccatttg atgataggcg agaagcaggg ggggaatcaa cagttgtgaa tccaaaatct    3540
ggatcttgga atttctttga ctggttttct ggactcatga gttggtttgg agggcctctt    3600
aagactatac tcctcatttg cctgtatgta gcattatcaa ttgggctctt tttccttctt    3660
atatatcttg gaagaacagg cctctctaaa atgtggcttg ctgccaccaa gaaagcctca    3720
tagatcagta cgtgtagaag caatatatag aaataagtaa acataagcaa atctaattat    3780
gtaaatattg tacagatggg tcaaactatt gggatatcca agtttagaat cttgtacaat    3840
agtactttag atgtaagctt agttgtaatt tggggtggtg gggtgaggca gcagtagtct    3900
caagtacatg tggatattct agttaatgtg aatgtctttt gccagattag ctgggaatta    3960
aactaactct ttgaagttgc accggtcttt gtgtgggtcg gcatggcatc tccacctcct    4020
cgcggtccga cctgggcatc cgaaggagga cgtcgtccac tcggatggct aagggagagc    4080
tcggatccgg ctgctaacaa agcccgaaag gaagctgagt tggctgctgc caccgctgag    4140
caataactag cataacccct tggggcctct aaacgggtct tgaggggttt tttgctgaaa    4200
ggaggaacta tatccggatc gagatcctct agccagatcc tctacgccgg acgcatcgtg    4260
gccggcgtcg actgcagagg c                                              4281
```

<210> SEQ ID NO 22
<211> LENGTH: 2092
<212> TYPE: DNA
<213> ORGANISM: Artificial
<220> FEATURE:
<223> OTHER INFORMATION: Partial sequence pUC57-S(-)

<400> SEQUENCE: 22

```
ggatccgatc caatagcgga agagcgccca atacgcaaac cgcctctccc gcgcgttgg     60 ccgattcatt aatgcagggg gatctcgatc ccgcgaaatt aatacgactc actatagaca    120
caaagacccc ctagtgctta tcaagtatat catggattac tttcctgtga tatctgttga    180
tttgcagagt ggtcgtcgtg ttgtgtcagt ggagtacatt agaggtgatg gtcctcccag    240
gataccttat tctatggttg ggccctgttg tgtctttctc atgcaccatc gtcctagtca    300
cgaggttcgc ttgcgattct ctgatttcta caatgtcgga gaattcccat accgagtcgg    360
acttggagac tttgtatcaa acgttgcacc tccaccagca aagcctttc agagacttat    420 tgatctaata ggccatatga ctcttagtga tttcacaagg ttccccaatc tgaaagaagc    480
catatcctgg cctcttggag aaccctccct ggctttcttt gacctaagct ccaccagagt    540
gcataggtct gatgatatta gaagggacca gattgctact ctagcaatga ggagctgcaa    600
gattaccaat gatctggagg actcctttgt tggcttacac aggatgatag tgaccgaggc    660
tatcctcaga gggattgact tgtgcctgtt gccaggcttt gatctcatgt atgaggttgc    720
```

```
tcatgttcag tgtgttcggc tcctgcaggc agcaagagag gatatttcta atgctgtagt      780
tccaaactca gctctcattg ctcttatgga ggagagcttg atgctgcgct catcactccc      840
tagcatgatg gggagaaaca actgggttcc agttgttcct ccaatcccag atgttgagat      900
agaatcagag gaagagagtg atgacgatgg atttgttgag gttgattaga gattaaggct      960
gccccacccc ccaccccaa tcccgaccgt aaccccaacc accccctttt ccccaaaccc      1020
ctgggcagcc acttaggctg ctgtcttgta cgcctgagca gctgccatga cagctgctga     1080
cggcttccca ttggaatcca caagcccaaa agctttcaag aattctctcc tcttctcatg     1140
gcttataaag ttgctattca ctgctgcatt cattggctgc gtgaacgttg cggcaacctc     1200
ctcctttgtt ctacctcgga ggtttgggtt gatgacccgg gagaactgca gcagatacag     1260
agagtgagca tccaatattg cccttagata gtcttctggt agagaagggt ccaccatgcc     1320
agcaaagctg gggtgcatca tatgccttgg gtatgcaggg gataggccat ccatggtggt     1380
cccagtgaca ggaagccact cactcaagac gaccaaagcc tggcaagtcc agccagccag     1440
ggcagcagca actcgtgata gagtcaactc atcccgggaa ggattcccct cctttagctt     1500
atacttgttg atgagagcct ccacagttgc tttgccttct ttcgacattt tcatcatcat     1560
cctccggggc ttgttgccac gagtcagagc cagaacaatc attttcttgg catccttctc     1620
ccagtcagcc ccaccatact gctttaagag ttcgataacc ctacgggcat caaatccttg     1680
ataagcaaac tctcggaccc actgttcaat ctcattgcgg tccactgctt gagcagcaaa     1740
ctggatcgca agctcttgat agttgtccat tattgtaata gtgtttgtat ctctagggag     1800
ctttgtgtgg gtcggcatgg catctccacc tcctcgcggt ccgacctggg catccgaagg     1860
aggacgtcgt ccactcggat ggctaaggga gagctcggat ccggctgcta acaaagcccg     1920
aaaggaagct gagttggctg ctgccaccgc tgagcaataa ctagcataac cccttggggc     1980
ctctaaacgg gtcttgaggg gttttttgct gaaaggagga actatatccg gatcgagatc     2040
ctctagccag atcctctacg ccggacgcat cgtggccggc ccaatatcta ga            2092
```

<210> SEQ ID NO 23
<211> LENGTH: 1229
<212> TYPE: DNA
<213> ORGANISM: Artificial
<220> FEATURE:
<223> OTHER INFORMATION: Partial sequence pUC57-SdeltaNSs

<400> SEQUENCE: 23

```
tctagagaaa ttaatacgac tcactataga cacaaagctc cctagagata caaacactat      60
tacaataatg gacaactatc aagagcttgc gatccagttt gctgctcaag cagtggaccg     120
caatgagatt gaacagtggg tccgagagtt tgcttatcaa ggatttgatg cccgtagggt     180
tatcgaactc ttaaagcagt atggtggggc tgactgggag aaggatgcca agaaaatgat     240
tgttctggct ctgactcgtg caacaagcc ccggaggatg atgatgaaaa tgtcgaaaga     300
aggcaaagca actgtggagg ctctcatcaa caagtataag ctaaaggagg ggaatccttc     360
ccgggatgag ttgactctat cacgagttgc tgctgccctg gctggctgga cttgccaggc     420
tttggtcgtc ttgagtgagt ggcttcctgt cactgggacc accatggatg cctatcccc     480 tgcataccca aggcatatga tgcaccccag ctttgctggc atggtggacc cttctctacc     540
agaagactat ctaagggcaa tattggatgc tcactctctg tatctgctgc agttctcccg     600
ggtcatcaac ccaaacctcc gaggtagaac aaaggaggag gttgccgcaa cgttcacgca     660
gccaatgaat gcagcagtga atagcaactt tataagccat gagaagagga gagaattctt     720
```

```
gaaagctttt gggcttgtgg attccaatgg aagccgtca gcagctgtca tggcagctgc      780
tcaggcgtac aagacagcag cctaagtggc tgcccagggg tttggggaaa aggggggtggt   840 tggggttacg gtcgggattg ggggtggggg gtggggcagc cttaatcttc aacagatatc    900
acaggaaagt aatccatgat atacttgata agcactaggg ggtctttgtg tgggtcggca    960
tggcatctcc acctcctcgc ggtccgacct gggcatccga aggaggacgt cgtccactcg   1020
gatggctaag ggagagctcg gatccggctg ctaacaaagc ccgaaaggaa gctgagttgg   1080
ctgctgccac cgctgagcaa taactagcat aaccccttgg ggcctctaaa cgggtcttga   1140 ggggttttt gctgaaagga ggaactatat ccggatcgag atcctctagc agatcctct    1200 acgccggacg catcgtggcc ggcgggccc                                     1229
```

<210> SEQ ID NO 24
<211> LENGTH: 1909
<212> TYPE: DNA
<213> ORGANISM: Artificial
<220> FEATURE:
<223> OTHER INFORMATION: Partial sequence pUC57-S

<400> SEQUENCE: 24

```
taatacgact cactatagac acaaagctcc ctagagatac aaacactatt acaataatgg     60
acaactatca agagcttgcg atccagtttg ctgctcaagc agtggaccgc aatgagattg    120
aacagtgggt ccgagagttt gcttatcaag gatttgatgc ccgtagggtt atcgaactct   180
taaagcagta tggtggggct gactgggaga aggatgccaa gaaaatgatt gttctggctc   240
tgactcgtgg caacaagccc cggaggatga tgatgaaaat gtcgaaagaa ggcaaagcaa    300
ctgtggaggc tctcatcaac aagtataagc taaaggaggg gaatccttcc cgggatgagt    360
tgactctatc acgagttgct gctgccctgg ctggctggac ttgccaggct ttggtcgtct    420
tgagtgagtg gcttcctgtc actgggacca ccatgatgg cctatcccct gcataccaa    480 ggcatatgat gcaccccagc tttgctggca tggtggaccc ttctctacca gaagactatc    540
taagggcaat attggatgct cactctctgt atctgctgca gttctcccgg gtcatcaacc    600
caaacctccg aggtagaaca aaggaggagg ttgccgcaac gttcacgcag ccaatgaatg    660
cagcagtgaa tagcaacttt ataagccatg agaagaggag agaattcttg aaagcttttg    720
ggcttgtgga ttccaatggg aagccgtcag cagctgtcat ggcagctgct caggcgtaca    780
agacagcagc ctaagtggct gcccaggggt ttggggaaaa ggggtggtt ggggttacgg   840 tcgggattgg gggtggggg tggggcagcc ttaatctcta atcaacctca acaaatccat   900
cgtcatcact ctcttcctct gattctatct caacatctgg gattggagga caactggaa    960 cccagttgtt tctccccatc atgctaggga gtgatgagcg cagcatcaag ctctcctcca   1020
taagagcaat gagagctgag tttggaacta cagcattaga aatatcctct cttgctgcct   1080
gcaggagccg aacacactga acatgagcaa cctcatacat gagatcaaag cctggcaaca   1140
ggcacaagtc aatccctctg aggatagcct cggtcactat catcctgtgt aagccaacaa   1200
aggagtcctc cagatcattg gtaatcttgc agctcctcat tgctagagta gcaatctggt   1260
cccttctaat atcatcagac ctatgcactc tggtggagct taggtcaaag aaagccaggg   1320
agggttctcc aagaggccag gatatggctt ctttcagatt ggggaacctt gtgaaatcac   1380
taagagtcat atggcctatt agatcaataa gtctctgaaa aggctttgct ggtggaggtg   1440
caacgtttga tacaaagtct ccaagtccga ctcggtatgg gaattctccg acattgtaga   1500
```

| aatcagagaa tcgcaagcga acctcgtgac taggacgatg gtgcatgaga aagacacaac | 1560 |
| agggcccaac catagaataa ggtatcctgg gaggaccatc acctctaatg tactccactg | 1620 |
| acacaacacg acgaccactc tgcaaatcaa cagatatcac aggaaagtaa tccatgatat | 1680 |
| acttgataag cactaggggg tctttgtgtg ggtcggcatg gcatctccac ctcctcgcgg | 1740 |
| tccgacctgg gcatccgaag gaggacgtcg tccactcgga tggctaaggg agagctcgga | 1800 |
| tccggctgct aacaaagccc gaaaggaagc tgagttggct gctgccaccg ctgagcaata | 1860 |
| actagcataa ccccttgggg cctctaaacg ggtcttgagg ggttttttg | 1909 |

<210> SEQ ID NO 25
<211> LENGTH: 1879
<212> TYPE: DNA
<213> ORGANISM: Artificial
<220> FEATURE:
<223> OTHER INFORMATION: Partial sequence pUC57-S-eGFP

<400> SEQUENCE: 25

| ggtacctcgc gaatgcatta gagaaattaa tacgactcac tatagacaca aagctcccta | 60 |
| gagatacaaa cactattaca ataatggaca actatcaaga gcttgcgatc cagtttgctg | 120 |
| ctcaagcagt ggaccgcaat gagattgaac agtgggtccg agagtttgct tatcaaggat | 180 |
| ttgatgcccg tagggttatc gaactcttaa agcagtatgg tgggggctgac tgggagaagg | 240 |
| atgccaagaa aatgattgtt ctggctctga ctcgtggcaa caagcccgg aggatgatga | 300 |
| tgaaaatgtc gaaagaaggc aaagcaactg tggaggctct catcaacaag tataagctaa | 360 |
| aggaggggaa tccttcccgg gatgagttga ctctatcacg agttgctgct gccctggctg | 420 |
| gctggacttg ccaggctttg gtcgtcttga gtgagtggct tcctgtcact gggaccacta | 480 |
| tggatggcct atcccctgca tacccaaggc atatgatgca cccagctttt gctggcatgg | 540 |
| tggacccttc tctaccagaa gactatctaa gggcaatatt ggatgctcac tctctgtatc | 600 |
| tgctgcagtt ctcccgggtc atcaacccaa acctccgagg tagaacaaag gaggaggttg | 660 |
| ccgcaacgtt cacgcagcca atgaatgcag cagtgaatag caactttata agccatgaga | 720 |
| agaggagaga attcttgaaa gcttttgggc ttgtggattc aatgggaag ccgtcagcag | 780 |
| ctgtcatggc agctgctcag gcgtacaaga cagcagccta agtggctgcc caggggtttg | 840 |
| gggaaaaggg ggtggttggg gttacggtcg ggattggggg tggggggtgg ggcagcctta | 900 |
| atcttctaga ttacttgtac agctcgtcca tgccgtgagt gatcccggcg gcggtcacga | 960 |
| actccagcag gaccatgtga tcgcgcttct cgttggggtc tttgctcagg gcggactggg | 1020 |
| tgctcaggta gtggttgtcg ggcagcagca cggggccgtc gccgatgggg gtgttctgct | 1080 |
| ggtagtggtc ggcgagctgc acgctgccgt cctcgatgtt gtggcggatc ttgaagttca | 1140 |
| ccttgatgcc gttcttctgc ttgtcggcca tgatatagac gttgtggctg ttgtagttgt | 1200 |
| actccagctt gtgccccagg atgttgccgt cctccttgaa gtcgatgccc ttcagctcga | 1260 |
| tgcggttcac cagggtgtcg ccctcgaact tcacctcggc gcgggtcttg tagttgccgt | 1320 |
| cgtccttgaa gaagatggtg cgctcctgga cgtagccttc gggcatggcg gacttgaaga | 1380 |
| agtcgtgctg cttcatgtgg tcggggtagc ggctgaagca ctgcacgccg taggtcaggg | 1440 |
| tggtcacgag ggtgggccag ggcacgggca gcttgccggt ggtgcagatg aacttcaggg | 1500 |
| tcagcttgcc gtaggtggca tcgccctcgc cctcgccgga cacgctgaac ttgtggccgt | 1560 |
| tcacgtcgcc gtccagctcg accaggatgg gcaccacccc ggtgaacagc tcctcgccct | 1620 |
| tgctcaccat gggatatact tgataagcac taggggggtct ttgtgtgggt cggcatggca | 1680 |

-continued

```
tctccacctc ctcgcggtcc gacctgggca tccgaaggag gacgtcgtcc actcggatgg    1740
ctaagggaga gctcggatcc ggctgctaac aaagcccgaa aggaagctga gttggctgct    1800
gccaccgctg agcaataact agcataaccc cttggggcct ctaaacgggt cttgaggggt    1860
tttttgctga aaggtcgac                                                 1879
```

<210> SEQ ID NO 26
<211> LENGTH: 702
<212> TYPE: DNA
<213> ORGANISM: Artificial
<220> FEATURE:
<223> OTHER INFORMATION: Partial sequence pUC57-Mv

<400> SEQUENCE: 26

```
gaattcgaaa ttaatacgac tcactataga cacaaagacc ggtgcaactt caaagagtta      60
gtttaattcc cagctaatct ggcaaaagac attcacatta actagaatat ccacatgtac     120
ttgagactac tgctgcctca ccccaccacc caaattaca actaagctta catctaaagt      180
actattgtac aagattctaa acttggatat cccaatagtt tgacccatct gtacaatatt     240
tacataatta gatttgctta tgtttactta tttctatata ttgcttctac acgtactgat     300
tctagagccc gtggcacgtg actagtaagc ttgatatctc gaggcgcgcc agctgcggcc     360
gctgattcgg tacccgggat ccttgctcac catggttaat gcaccgtctt tgtgtgggtc     420
ggcatggcat ctccacctcc tcgcggtccg acctgggcat ccgaaggagg acgtcgtcca     480
ctcggatggc taagggagag ctcggatccg gctgctaaca aagcccgaaa ggaagctgag     540
ttggctgctg ccaccgctga gcaataacta gcataacccc ttggggcctc taaacgggtc     600 ttgagggggtt ttttgctgaa aggaggaact atatccggat cgagatcctc tagccagatc    660
ctctacgccg gacgcatcgt ggccggcgtc gactgcctgc ag                        702
```

<210> SEQ ID NO 27
<211> LENGTH: 1056
<212> TYPE: DNA
<213> ORGANISM: Artificial
<220> FEATURE:
<223> OTHER INFORMATION: Partial sequence pUC57-Mv-eGFP

<400> SEQUENCE: 27

```
taatacgact cactatagac acaaagaccg gtgcaacttc aaagagttag tttaattccc      60
agctaatctg gcaaaagaca ttcacattaa ctagaatatc cacatgtact tgagactact     120
gctgcctcac cccaccaccc caaattacaa ctaagcttac atctaaagta ctattgtaca     180
agattctaaa cttggatatc ccaatagttt gacccatctg tacaatattt acataattag     240
atttgcttat gtttacttat ttctatatat tgcttctaca cgtactgatt ctagattact     300
tgtacagctc gtccatgccg tgagtgatcc cggcggcggt cacgaactcc agcaggacca     360
tgtgatcgcg cttctcgttg gggtctttgc tcagggcgga ctgggtgctc aggtagtggt     420
tgtcgggcag cagcacgggg ccgtcgccga tggggtgtt ctgctggtag tggtcggcga     480
gctgcacgct gccgtcctcg atgttgtggc ggatcttgaa gttcaccttg atgccgttct     540
tctgcttgtc ggccatgata tagacgttgt ggctgttgta gttgtactcc agcttgtgcc     600
ccaggatgtt gccgtcctcc ttgaagtcga tgcccttcag ctcgatgcgg ttcaccaggg     660
tgtcgccctc gaacttcacc tcggcgcggg tcttgtagtt gccgtcgtcc ttgaagaaga     720
tggtgcgctc ctggacgtag ccttcgggca tggcggactt gaagaagtcg tgctgcttca     780
```

-continued

```
tgtggtcggg gtagcggctg aagcactgca cgccgtaggt cagggtggtc acgagggtgg    840
gccagggcac gggcagcttg ccggtggtgc agatgaactt cagggtcagc ttgccgtagg    900
tggcatcgcc ctcgccctcg ccggacacgc tgaacttgtg gccgttcacg tcgccgtcca    960
gctcgaccag gatgggcacc accccggtga acagctcctc gcccttgctc accatggtta   1020
atgcaccgtc tttgtgtggg tcggcatggc atctcc                             1056
```

<210> SEQ ID NO 28
<211> LENGTH: 3246
<212> TYPE: DNA
<213> ORGANISM: Artificial
<220> FEATURE:
<223> OTHER INFORMATION: Partial sequence pUC57-GnGc

<400> SEQUENCE: 28

```
gaattcgctc ttcaagcacc accatggccg gaatcgccat gacagtgttg cctgcactgg     60
ccgtgtttgc tttggctccc gtggtgtttg ctgaagaccc gcacctgcgc aaccgtcctg    120
gcaagggcca caactatatt gacggcatga cccaggaaga cgctacatgt aagccggtga    180
catatgctgg cgcctgctct agcttcgacg tgctcctgga aagggaaaaa ttcccactgt    240
ttcagtccta tgctcatcac cgcacccctgc tggaggccgt ccacgacaca attatcgcaa    300
aggccgatcc ccctagctgc gacctgcaga gcgcccatgg caacccgtgc atgaaagaga    360
aactggtgat gaaaacacat tgcccgaatg actaccagtc tgcacactat ctcaacaatg    420
acggcaagat ggcttccgtg aaatgcccac caaagtacga actgaccgag gattgtaact    480
tttgccgcca gatgacgggc gcaagtctta gaagggtag ttaccctctg caggacctgt    540
tttgtcagtc ctcagaggac gacggcagca agctcaaaac taaaatgaag ggcgtgtgcg    600
aggtgggtgt gcaagccctt aaaaagtgcg acggccagct ctccaccgcc cacgaagtgg    660 tccctttttgc tgtttttaag aatagcaaga aggtgtacct cgacaaactg gatctgaaaa    720
ctgaagaaaa cctgcttcct gatagtttcg tgtgcttcga gcacaaaggc cagtacaagg    780
gtaccatgga ctccggtcag accaaacgcg agctgaaatc cttcgacatt tcccagtgcc    840
ccaagatcgg aggacacgga agcaagaaat gcaccggcga cgccgccttc tgtagcgcct    900
acgaatgcac tgcccaatat gccaacgctt attgctctca cgccaacggt tctggcgtgg    960
tgcagattca ggtgtccggc gtctggaaga agccgttgtg tgtgggctat gaacgcgtgg   1020
tggtgaagcg ggagttgagc gctaagccca tccagcgtgt ggagccatgc accacctgca   1080
tcacaaagtg tgaaccacac ggtctggtgg tgaggtctac cggattaag attagctctg   1140 cagtcgcctg tgcaagtggc gtgtgtgtca ctggctcaca gagtccctca acggaaatca   1200
ctttgaagta tccggcatc agccaaagct ctggaggcga tatcggcgtc catatggccc   1260
acgacgacca gagcgtgagc tcaaagattg ttgcccactg ccccccgcag gacccttgcc   1320
ttgtgcacgg ctgcattgtg tgcgcccacg gattgattaa ctaccaatgc cacaccgcac   1380
tcagcgcctt tgtcgtggtt tttgtgtttt cttccgttgc aatcatttgc ctggccatcc   1440
tgtacaaagt cctcaaatgc ctgaaaattg ccccctagga ggtcctcgac ccgttgatgt   1500
ggattacggt gttcatccga tgggtgtata agaagatggt ggcaagggtg gcagataaca   1560
ttaaccaggt gaacagagag ataggatgga tggaaggtgg ccagttggca cttggtaacc   1620
ctgcccccat ccctcgacac gccccccattc cgagatatag cacctacctc atgctgcttc   1680
tgatcgtgag ctacgcatcc gcctgcagcg agctgattca ggccagcagt agaatcacga   1740
cgtgcagtac agaaggagtg aacaccaaat gccgcctgtc cggaaccgcc ctgattcgcg   1800
```

```
ccggctccgt cggcgccgag gcctgtctca tgctcaaggg cgtgaaggag gaccagacca    1860
aattcctgaa gatcaagact gtttcatctg aactctcatg tcgggaggga cagtcctact    1920
ggacaggtag cttcagtcca aagtgtcttt cctcccgtcg ctgtcacctg gtcggggaat    1980
gtcatgtgaa taggtgtctg tcatggcgcg acaacgagac ttccgccgaa ttttctttcg    2040
tgggtgaatc caccaccatg cgggaaaata aatgtttcga acagtgcggc ggctggggtt    2100
gtggctgctt caacgtgaac ccgtcttgcc tctttgttca tacctatctg caatctgtgc    2160
gcaaggaagc tctgcgcgtt tttaattgta tcgactgggt gcataagctc acattggaaa    2220
tcacagattt tgacggctcc gtcagcacca tcgacctggg agcttcttca tcacgattta    2280
caaactgggg tagcgtgagt ctctccctgg atgccgaagg tatttcaggc agcaacagtt    2340
ttagtttcat cgaatcccct ggcaagggt atgccatcgt ggacgaacct ttctccgaga    2400
tcccaaggca gggcttcctt ggagagatca ggtgcaactc agaaagctcc gtgttgagtg    2460
ctcatgagag ttgtctgagg gccccgaacc tgatctccta taagcccatg attgaccagc    2520
ttgagtgcac aacaaatctt atagatccct tcgtcgtgtt tgaaagaggc tccctccccc    2580
agacccgcaa cgacaagacg ttcgcagctt ctaagggcaa ccgtggagtc caggccttta    2640
gcaagggttc cgtgcaggcc gacctgacat tgatgttcga taacttcgag gtggatttcg    2700
tcggagccgc tgtctcctgc gatgcagcat ttctgaatct gactggctgc tatagttgca    2760
atgctggagc acgcgtgtgc ctgagcatta cctccactgg tacaggtacc ctgtccgccc    2820
acaataaaga tggaagtctt cacatcgtgc tgcctagcga aacggcaca aaggaccaat    2880 gtcagattct gcactttacc gtgcccgagg tggaggaaga gttcatgtac tcctgtgatg    2940
gcgatgagag gcctctgctg gtcaagggca ctctcatcgc cattgaccct tttgatgaca    3000
gacgcgaggc tggcggagag agcactgtcg ttaacccaaa gagcggctct ggaatttct    3060 ttgactggtt cagcggactc atgtcctggt ttggaggccc actcaagacg attctcctga    3120
tctgcctgta cgtggctctg agtatcggac tcttcttcct cctgatctat ctcggaagaa    3180
ccggcttgtc aaaaatgtgg ctggccgcta caagaaagc cagttaagct cttcctcagc    3240
ggccgc                                                              3246
```

<210> SEQ ID NO 29
<211> LENGTH: 3611
<212> TYPE: DNA
<213> ORGANISM: Artificial
<220> FEATURE:
<223> OTHER INFORMATION: partial sequence of pCIneo-NSmGnGc encoding the ORF of RVFV 35/74 M genome segment

<400> SEQUENCE: 29

```
gaattcacca tgtatgtttt actaacaatt ctgatcacgg ttctggtgtg tgaggcggtt     60
attagagtgt ctctaagttc cacaagagaa gagacctgct tggtgactta caccaaccca    120
gagatgattg aaggagcttg ggattcactc agagaggagg agatgccaga ggagctctcc    180
tgttccatat caggcataag ggaggtcaaa acctcaagcc aggaattgta tagggcatta    240
aaagccatca ttgctgctga tggcttgaac aacatcacct gccatggtaa ggatcctgag    300
gataagattt ctctcgtaaa gggtcctcct cacaaaaagc gggtggggat agttcggtgt    360
gagagacgaa gagacgctaa gcaaatagga agagaaacca tggcagggat tgcaatgaca    420
gtccttccag cctagcagt ttttgctttg gcacctgttg ttttgctga agaccctcat    480 ctcagaaaca gaccagggaa ggggcacaac tacattgacg ggatgactca ggaggacgcc    540
```

```
acatgcaaac ctgtgacata tgctggggct tgtagcagtt ttgatgtctt gctcgaaaag    600
ggaaaattcc ccctcttcca gtcgtatgcc catcacagaa ccctactaga agcagttcac    660
gacaccatca ttgcaaaggc tgatccacct agctgtgacc ttcagagtgc tcatgggaat    720
ccctgcatga aggagaaact cgtgatgaag acacactgtc caaatgacta ccagtcagct    780
cattacctca caatgacgg gaaaatggct tcagtcaagt gccctcctaa atatgagctc     840
actgaggact gcaattttg caggcagatg acaggtgcta gcttgaagaa ggggtcttat     900
cctcttcagg acttatttg tcagtcaagt gaggatgatg gatcaaaatt aaaaacaaaa    960
atgaaagggg tctgcgaagt gggggttcaa gcactcaaaa agtgtgatgg ccaactcagc   1020
actgcacatg aggttgtgcc ctttgcagta tttaagaact caaagaaggt ttatcttgat   1080
aagcttgacc tcaagactga ggaaaatctg ttgccagact catttgtctg cttcgagcat   1140
aagggacagt ataaaggaac aatggactct ggtcagacca gagggagct caaaagcttt    1200
gatatctctc agtgccccaa gattggagga catggtagca agaagtgcac tggggacgca   1260
gcttttgct ctgcttatga gtgcactgct caatacgcca atgcttattg ttcacatgct    1320
aatgggtcag gagttgtaca gatacaagta tccggggtct ggaagaagcc tttgtgtgtc   1380
gggtatgaga gggtggttgt gaagagagaa ctctctgcta agcccatcca gagagttgag   1440
ccttgcacaa cttgtataac caaatgtgag cctcacggat tggttgtccg atcaacaggt   1500
ttcaagatat catctgcagt tgcttgtgct agcggagttt gcgttacagg atcgcagagc   1560
ccttctaccg agattacact caagtatcca gggatatccc agtcctctgg gggggacata   1620
ggggttcaca tggcacatga tgatcagtca gttagctcca aaatagtagc tcactgccct   1680
ccccaggatc catgcctagt gcatggctgc atagtgtgtg ctcatggcct gataaattac   1740
cagtgtcaca ctgctctcag tgcctttgtt gttgtgttcg tatttagctc tgtcgcaata   1800
atttgtttgg ccattctta taaagttctc aagtgcctaa agattgcccc aaggaaagtt   1860
ctggatccac taatgtggat tactgttttc atcagatggg tgtataagaa gatggttgcc   1920
agagtagcag acaatatcaa tcaggtgaac agggaaatag gatggatgga aggaggccag   1980
ctggctctag ggaaccctgc ccctattcct cgtcatgctc caattccacg ttatagcaca   2040
tacctaatgc tactattgat tgtctcatat gcatcagcat gttcagaact gattcaggca   2100
agctccagaa tcaccacttg ctccacagaa ggtgtcaaca ccaagtgtag gctgtctggc   2160
acagcattaa tcagggcagg gtcagttggg gcagaggctt gtttgatgtt aaggggggtc   2220
aaggaagacc aaaccaagtt tttgaagata aaaactgtct caagtgagct atcgtgcagg   2280
gagggccaga gctattggac tgggtccttt agccctaaat gtctgagctc aaggagatgc   2340
catcttgtcg gggaatgtca tgtgaatagg tgtctgtctt ggagagacaa tgaaacctca   2400
gcagaatttt catttgttgg ggaaagcacg accatgcggg agaacaagtg ttttgagcag   2460
tgtggaggat gggatgtgg gtgtttcaat gtgaacccat cttgcttatt tgtgcacacg   2520
tatctgcagt cagtcagaaa agaggccctt agagttttca actgtatcga ttgggtgcat   2580
aaactcactc tagagattac tgactttgat ggctctgttt caacaataga cctgggagca   2640
tcatctagcc gtttcacaaa ctggggttca gttagcctct cactgacgc agagggcatt    2700
tcaggctcaa acagcttttc cttcattgag agcccaggca agggtatgc aattgttgat    2760
gagccattct cagaaattcc tcggcaaggg ttcttggggg agatcaggtg caattcagaa   2820
tcttcagtcc tgagtgctca tgaatcatgc cttagggcac caaatcttat ttcatacaag   2880
```

-continued

```
cccatgatag atcagttgga gtgcacaaca aatctgattg atcccttttgt tgtctttgag    2940 aggggctctc tgccacagac aaggaatgac aaaacctttg cagcttcaaa aggaaatagg    3000
ggtgttcaag ctttctctaa gggctctgta caggctgatc taacactgat gtttgacaat    3060
tttgaggtgg actttgtggg agcagccgtg tcttgtgatg ccgccttctt aaatttgaca    3120
ggttgctatt cctgcaatgc aggggccaga gtctgcctgt ctatcacatc cacaggaact    3180
ggaactctct ctgccacaa taaagatgga tctctgcata tagttcttcc atcagagaat    3240
ggaacaaaag atcagtgtca gatactacac ttcactgtac ctgaggtaga ggaggagttt    3300
atgtactctt gtgatggaga tgagcggcct ctgttggtga agggaaccct gatagctatt    3360
gatccatttg atgataggcg agaagcaggg ggggaatcaa cagttgtgaa tccaaaatct    3420
ggatcttgga atttctttga ctggtttttct ggactcatga gttggtttgg agggcctctt    3480
aagactatac tcctcatttg cctgtatgta gcattatcaa ttgggctctt tttccttctt    3540
atatatcttg gaagaacagg cctctctaaa atgtggcttg ctgccaccaa gaaagcctca    3600
taggcggccg c                                                         3611
```

<210> SEQ ID NO 30
<211> LENGTH: 768
<212> TYPE: DNA
<213> ORGANISM: Artificial
<220> FEATURE:
<223> OTHER INFORMATION: codon optimised N gene of RVFV 35/74

<400> SEQUENCE: 30

```
gaattctcta gacaccatgg ataactatca ggagctggcc atccagtttg ccgcccaggc    60
cgtggacaga aacgagatcg aacagtgggt gcgtgagttc gcttaccagg gtttcgacgc    120
ccgccgggtg attgaactgc tgaagcagta tggaggtgcc gactgggaga agacgccaa    180 gaaaatgatc gtgctggctc tgactagagg caacaagccc aggagaatga tgatgaagat    240
gagcaaggaa ggaaaggcta ctgtggaagc cctgatcaac aagtacaaac ttaaggaagg    300 aaaccctct cgcgatgaac tgactctcag cagagtggcc gcagcccttg ccggatggac    360
atgtcaggcc ctggtcgtgc tttccgagtg gttgcccgtg acaggaacca ccatggacgg    420
cctgtcccca gcatatccca gacatatgat gcatccctct ttcgccggca tggtcgaccc    480
aagtctgcct gaggattacc tcagagccat cctggatgcc acagtctttt acttgctgca    540
gttttctcgg gtgattaacc ccaacctccg cggaagaaca aggaggagg ttgcagccac    600 ctttacacag cccatgaacg cagctgtgaa tagtaacttc atttctcacg aaaaacgacg    660
cgagttcctc aaaagccttcg gcctggtgga cagcaacgga aagccttctg cagccgtcat    720
ggccgccgcc caggcataca agactgccgc ttaaaagctt gcggccgc                 768
```

<210> SEQ ID NO 31
<211> LENGTH: 6296
<212> TYPE: DNA
<213> ORGANISM: Artificial
<220> FEATURE:
<223> OTHER INFORMATION: Partial sequence of pCIneo-L with the ORF of
      the L gene of RVFV 35/75

<400> SEQUENCE: 31

```
ctcgagacca tggattctat attatcaaaa cagctggttg acaagactgg ttttgttaga    60
gtgccaatca gcattatga ctgtacaatg ctaactctgg cactcccaac atttgatgtc    120
tccaagatgg tagatagaat taccatagac ttcaatttag acgacataca aggagcatct    180
```

```
gaaataggct caactttgct accctctatg tcgatagatg tggaagatat ggccaatttt    240
gttcacgatt tcacctttgg ccacttagct gacaagactg acagactctt aatgcgtgag    300
tttcccatga tgaatgacgg gtttgatcat ctgagccctg acatgattat caaaactaca    360
tctggcatgt ataacatcgt tgagttcacc acctttaggg gggatgaaag aggtgcattc    420
caggctgcca tgactaaact cgctaagtat gaggttcctt gtgagaacag atctcagggc    480
aggactgttg ttctttatgt tgttagcgcc taccggcatg gtgtttggtc taatttggag    540
ctagaggact ctgaagcaga ggagatggta tataggtaca gacttgccct tagtgtgatg    600
gatgagctaa ggaccttgtt cccagaactg tcatccacag atgaggaact aggaaagact    660
gagagagagt tgctagccat ggtctcctcc atccaaataa attggtcagt cacagaatct    720
gtgtttcctc cctttagcag agaaatgttt gacaggttca gatcttctcc tcccgattca    780
gagtacatca cgaggatagt gagcagatgc ctcataaatt ctcaagagaa actcatcaat    840
aattccttct ttgctgaagg gaatgataaa gttttgagat tttcaaaaaa cgctgaggag    900
tgttccttgg caatagagag agctttaaat cagtataggg cagaagacaa ccttagggac    960
ctaaatgacc acaagtctac tattcagctg cctccctggc tgtcctatca cgatgccgat   1020
ggcaaagatc tgtgccctct tcagggatta gatgtgagag agaccatccc catgtgcaac   1080
ctgtggagag aagtggttac ctctgcaaat ctagaggaga ttgagaggat gcacgatgat   1140
gcagcggcag aacttgagtt tgcccttt ca ggggtgaagg acaggccaga tgaaagaaac   1200
agataccata gagtccatct gaatatggac tcagatgata gtgtctacat agctgcttta   1260
ggggttaatg gaaagaagca taagcagac acattagtgc aacaaatgag agacaggagc   1320
aaacagccct ctctctccaga tcatgatgtg gatcacatat ctgaatttct ctctgcatgc   1380
tctagtgact tgtgggcaac agatgaggac ctatacaacc ctctctcttg tgataaagag   1440
cttagattgg cagctcagag aattcatcag ccatccttat cagaaagggg cttcaatgag   1500
attataaacag agcactacag atttatggga agtaggatag gatcatggtg ccaaatggtc   1560
agtttaatag gagctgagct atcagcttct gtaaagcaac atgttaagcc taactatttt   1620
gtgattaaac gactactagg ttctgggatt ttcttgctga tcaagcctac ttccagcaaa   1680
agccatatat tcgtgtcttt tgcaattaag cgctcttgct gggcctttga tctctccact   1740
tccagggttt tcaaaccta catagatgcc ggggatctgt tagttactga cttt gtttct   1800
tacaaactaa gtaagcttac caacctctgc aagtgcgttt cgttaatgga atcctccttc   1860
tcatttggg cagaggcatt tgggattcca agctggaact ttgttagtga cttgttcagg   1920
tcttcagact ctgcagcaat ggatgcctca tacatgggca aactctcttt attaacccct   1980
ttggaagaca aagcaacaac tgaagagtta cagactattg caagatatat aatcatggag   2040
ggctttgtct cgcccccaga aatcccaaaa cctcacaaga tgacctctaa gtttcccaag   2100
gttctcaggt cagagctgca ggtttactta ttaaactgct tatgcagaac tatccagaga   2160
atagcaggtg agccctttat tcttaagaag aaggatgggc tatatcctg ggtggcatg    2220
tttaatcctt tttcagggcg tccactgctt gatatgcaac cactcatcag ctgttgttac   2280
aatggttact ttaaaaacaa agaagaagag actgagcctt cctcccttc tgggatgtat    2340
aagaaaatta tagaacttga gcaccttaga ccacagtcag atgccttctt gggttataaa   2400
gatccagaac tacctagaat gcatgagttc agtgtttcct acttgaagga ggcttgcaat   2460
catgctaagc tggtcttaag gagtctctat ggacagaatt tcatggagca aatagacaac   2520
caaattattc gagagctcag tgggttgact ctagaaagat tagccacact taaggccaca   2580
```

```
agcaacttta atgagaattg gtatgtctat aaggatgtgg cagacaagaa ctacacaagg    2640
gataaattat tagtgaagat gtcaaaatat gcttctgagg gaaagagcct agctatccag    2700
aagtttgagg attgcatgag gcagatagag tcacaaggat gtatgcacat ttgtttgttt    2760
aagaaacaac agcatggagg tctgagagag atctatgtga tgggtgcaga ggaagaatt     2820 gttcaatcgg tggtggagac aatagccagg tctataggga agttctttgc ttctgatacc    2880
ctctgtaacc cccccaataa ggtgaaaatt cctgagacac atggcattag ggctcggaag    2940
caatgtaagg ggcctgtgtg gacttgtgca acatcagatg atgcaaggaa gtggaaccaa    3000
ggccattttg ttacaaagtt tgccctcatg ctatgtgagt tcacctctcc taagtggtgg    3060
ccattgatca ttaggggatg ttcaatgttt accaggaaaa ggatgatgat gaatttgaat    3120
tatcttaaga tcctggatgg tcatcgagag cttgatatta gagatgactt tgtgatggat    3180
ctcttcaaag cttatcatgg tgaggcagaa gttccatggg ctttaaggg taaaacatat      3240 ctggaaacca cgacagggat gatgcagggg atattgcatt atacttcctc attattacac    3300
accattcatc aagaatacat ccggtccttg tcctttaaaa tattcaacct gaaggttgct    3360
cctgagatga gcaaaagcct ggtttgtgac atgatgcaag gatcagatga tagtagcatg    3420
ctaatcagct tcccagctga tgacgagaag gttctcacca gatgcaaagt ggccgcagcc    3480
atatgcttcc gaatgaagaa ggagctggga gtgtaccttg ccatctaccc ctcagagaag    3540
tccacagcaa acacagattt tgtgatggag tacaattctg aattttattt ccacacccag    3600
catgttagac cgacgatcag gtggattgca gcatgttgca gcctgccaga agtggaaaca    3660
ctagtagccc gccaggaaga ggcctctaat ctaatgactt cagttactga ggggggtggg    3720
tcattctcct tagctgcaat gattcagcaa gctcagtgca ctctccatta catgctaatg    3780
ggcatgggag tgtctgagct attcttagag tataagaagg cagtgctgaa gtggaatgac    3840
cctggtctgg gtttcttcct gcttgacaat ccttatgcgt gcgggttggg aggttttaga    3900
tttaatctct tcaaagccat caccagaact gatttgcaga agctatatgc tttcttcatg    3960
aagaaggtta agggctcagc tgctaggac tgggcagatg aggatgttac catcccagaa      4020
acgtgtagcg tgagcccagg tggcgctcta attcttagct cctctctaaa gtggggatct    4080
aggaagaagt ttcagaaaact gagagaccgt ttgaacatac cagagaactg gattgagcta    4140
ataaatgaga tccagaggt gctctatcga gctcccagaa caggcccaga atattgttg       4200 cgcattgcag agaaagtcca tagccctggt gttgtgtcat cattgtcttc tggcaatgca    4260
gtctgtaaag tcatggcctc agctgtatac ttcttatcag caacaatttt tgaagacact    4320
ggacgccctg agttcaactt cttagaggat tccaagtaca gcttgctaca aaagatggcc    4380
gcatattctg ctttcatgg tttcaatgat atggagccag aagatatatt attcctattc      4440
ccgaacattg aggaattaga atcactggat tctatagttt acaacaaggg agaaatagac    4500
atcatcccaa gagttaatat cagggatgca acccaaacca gggtcactat ctttaatgag    4560
cagaagaccc tccgaacatc tccagagaag ttggtgtcag acaagtggtt cgggactcag    4620
aagagtagga taggcaaaac aactttcctg gctgaatggg agaagctaaa gaaaattgtg    4680
aagtggttgg aagacactcc agaagcaact ctagctcaca ctccactgaa taaccatatt    4740
caggttagga attcctttgc tagaatggaa agcaagccta gaacggttag aataacagga    4800
gctcctgtaa agaagaggtc aggggttagc aagatagcta tggttatccg tgacaatttc    4860
tcccggatgg gccatcttag aggtgtagaa gacctcgctg gcttcactcg tagtgtgtca    4920
```

```
gctgaaatcc tcaagcactt tctgttctgc atactacagg gtccatacag tgagagctat    4980
aagctacagc taatctacag agtcctaagc tcagtgtcaa acgttgagat aaaggaatcg    5040
gatggtaaga caaaaaccaa tttgattggg atccttcaga gatttctaga tggtgatcac    5100
gttgtcccta taattgaaga gatgggagcc ggaacagtgg gtggattcat caagagacaa    5160
cagtctaagg ttgtgcaaaa taaagtggtc tattatggag ttgggatctg gagaggcttc    5220
atggatggat atcaggtcca tcttgagata gaaaatgaca taggacagcc cccaaggctt    5280
aggaatgtca caactaactg tcagagcagc ccatgggatc tgagtgtccc aataaggcag    5340
tgggcagaag acatgggggt cacaaacaac caggattatt cctctaaatc tagcagagga    5400
gctagatatt ggatgcattc atttaggatg caaggaccca gcaagccatt tggatgccca    5460
gtttatatta ttaagggtga catgtcagat gttatcagac tgagaaaaga ggaggtggag    5520
atgaaagtac ggggctctac tctcaacttg tacactaagc accattctca tcaagactta    5580
cacattttat cttacactgc atcagacaat gatctcagtc caggcatttt caagtcaata    5640
tcagatgagg gagtagctca agccctgcag ttatttgaga gggagccaag caactgctgg    5700
gtgagatgtg agtctgtagc tccaaaattc atatcagcca tccttgagat atgtgagggg    5760
aagagacaga taaaaggaat caacagaacc agactctcag agattgtgag aatttgttct    5820
gaatcttccc taagatcaaa ggtcggatct atgttctcat ttgtcgccaa tgttgaggag    5880
gcccatgatg ttgattatga tgcgttaatg gatctaatga cagaagatgc taagaacaat    5940
gcattcagtc atgttgtcga ttgcatagag ttggatgtta atggtcctta cgagatggag    6000
tcttttgata catctgatgt caacctcttt gggccagccc attacaagga catcagttca    6060
ttatctatga ttgctcatcc cttaatggat aagtttgttg attatgccat ttccaagatg    6120
gggagagcct cagttagaaa agttctagag acaggtcggt gctctagcaa agactatgat    6180
ttatcaaagg ttctcttcag aactctacag agaccagaag agagcattag gatagatgat    6240
ctggagttat atgaggagac agatgtggcg gatgacatgc taggctaagc ggccgc        6296
```